US007514546B2

(12) United States Patent
Kingsman et al.

(10) Patent No.: US 7,514,546 B2
(45) Date of Patent: *Apr. 7, 2009

(54) ANTIBODIES

(75) Inventors: Susan Mary Kingsman, Oxford (GB); Christopher R. Bebbington, San Mateo, CA (US); Miles W. Carroll, Oxford (GB); Fiona M. Ellard, Oxford (GB); Kevin A. Myers, Oxford (GB)

(73) Assignee: Oxford BioMedica (UK) Ltd., Oxford (GB)

( * ) Notice: Subject to any disclaimer, the term of this patent is extended or adjusted under 35 U.S.C. 154(b) by 65 days.

This patent is subject to a terminal disclaimer.

(21) Appl. No.: 11/333,859

(22) Filed: Apr. 26, 2006

(65) Prior Publication Data

US 2007/0259400 A1 Nov. 8, 2007

Related U.S. Application Data

(63) Continuation of application No. 10/016,686, filed on Nov. 2, 2001, now Pat. No. 7,074,909, which is a continuation-in-part of application No. PCT/GB00/04317, filed on Nov. 13, 2000.

(30) Foreign Application Priority Data

| Nov. 18, 1999 | (WO) | PCT/GB99/03859 |
| Feb. 15, 2000 | (GB) | 0003527.9 |
| Mar. 2, 2000 | (GB) | 0005071.6 |

(51) Int. Cl.
C07H 21/04 (2006.01)
C12N 15/00 (2006.01)

(52) U.S. Cl. .................... 536/23.53; 435/69.7
(58) Field of Classification Search ........................ None
See application file for complete search history.

(56) References Cited

U.S. PATENT DOCUMENTS

| 4,997,913 | A | 3/1991 | Hellstrom et al. |
| 5,559,099 | A | 9/1996 | Wickham et al. |
| 5,591,624 | A | 1/1997 | Barber et al. |
| 5,824,782 | A | 10/1998 | Holzer et al. |
| 5,856,140 | A | 1/1999 | Shimamura et al. |
| 5,876,691 | A | 3/1999 | Chester et al. |
| 6,348,584 | B1 | 2/2002 | Hodgson et al. |
| 6,514,498 | B1 | 2/2003 | Antonsson et al. |
| 6,852,703 | B1 | 2/2005 | Kingsman et al. |
| 7,074,909 | B2 * | 7/2006 | Kingsman et al. .......... 536/23.1 |
| 2007/0161080 | A1 * | 7/2007 | Kingsman et al. .......... 435/69.1 |

FOREIGN PATENT DOCUMENTS

| EP | 0336582 A1 | 10/1989 |
| EP | 0803574 A2 | 5/1990 |
| WO | WO89/07947 A1 | 9/1989 |
| WO | WO92/11383 A1 | 7/1992 |
| WO | WO92/22653 A1 | 12/1992 |
| WO | WO94/11513 A1 | 5/1994 |
| WO | WO96/15238 A1 | 5/1996 |
| WO | WO96/30504 A1 | 10/1996 |
| WO | WO96/30512 A1 | 10/1996 |
| WO | WO96/34969 A2 | 11/1996 |
| WO | WO97/17090 A1 | 5/1997 |
| WO | WO97/36932 A1 | 10/1997 |
| WO | WO98/55607 A2 | 12/1998 |
| WO | WO01/36486 A2 | 5/2001 |

OTHER PUBLICATIONS

Rudikoff et al (Proc Natl Acad Sci USA 1982 vol. 79 pp. 1979-1983).*
Mountain, Andrew "Gene therapy: the first decade", *TIBTECH* (2000) 18:119-127.
Myers, Kevin A., et al. "Isolation of a cDNA Encoding 5T4 Oncofetal Trophoblast Glycoprotein", *The Journal of Biological Chemistry* (1994) 269(12):9319-9324.
Verma, Inder M., et al. "Gene therapy promises, problems and prospects", *Nature* (1997) VI. 389:239-242.
Walther, Wolfgang, et al. Viral Vectors for Gene Transfer, *Drugs* (2000) 2:249-271.
Chamberlain, Ronald S., et al. "Costimulation Enhances the Active Immunotherapy Effect of Recombinant Anticancer Vaccines", *Cancer Research* (1996) 56:2832-2836.
Riddell, S.R., et al. "T-cell mediated rejection of gene-modified HIV-specific cytotoxic T lymphocytes in HIV-infected patients", *Nature Medicine* (1996) 2:216-221.
Richter, J., et al. "Clinical gene therapy in hematology: Past and future", *Int. Journal. Hematology* (2001) 73:162-169.
Greco, O., et al. "Cancer gene therapy: 'delivery, deliveyr, delivery'", *Frontiers in Bioscience* (2002) 7:d1516-1524.
Crystal, R.G. "Transfer of genes to humans: early lessons and obstacles to success", *Science* (1995) 270:404-410.
Gertsmayer, B. et al. "Costimulation of T Cell Proliferation by a Chimeric B7-2 Antibody Fusion protein Specifically Targeted to Cells Expressing the erbB2 Proto-Oncogene", *The Journal of Immunology* (1997) 158:4584-4590.
Naldini, Luigi, et al. "In Vivo Gene Delivery and Stable Transduction of Nondividing Cells by a Lentiviral Vector", *Science* (1996) 272:263-267.

(Continued)

*Primary Examiner*—Christopher H Yaen
(74) *Attorney, Agent, or Firm*—Marshall, Gerstein & Borun LLP

(57) ABSTRACT

The use of an ScFv Ab (ScFv Ab) capable of recognizing a disease associated molecule (DAM) in the manufacture of a medicament for the prevention and/or treatment of a disease condition associated with a DAM is described. The ScFv Ab has therapeutic, diagnostic and prognostic applications.

25 Claims, 24 Drawing Sheets

OTHER PUBLICATIONS

Anderson, W. French "Human Gene Therapy", *Nature* (1998) 392:25-30.

Osaki, et al. "Gene Therapy for Carcinoembryonic Antigen-producing Human Lung Cancer Cells by Cell Type-specific Expression of Herpes Simplex Virus Thymidine Kinase Gene", *Cancer Research* (1994) 54:5258-5261.

Alvarez, R.D., et al. "A phase I study of recombinant adenovirus vector-mediated delivery of an anti-erbB-2 single-chain (sFv) antibody gene for previously treated ovarian and extraovarian cancer patients", *Human Gene Therapy* (1997) 8(2):229-242.

Deshane, Jessy et, al. "Targeted tumor killing via an intracellular antibody against erbB-2", *Journal of Clinical Investigation* (1995) 96(6):2980-2989.

Wels, W., et al. "Biotechnological and gene therapeutic strategies in cancer treatment", *Gene* (1995) 159(1):73-80.

Whittington, H.A., et al. "Recombinant adenoviral delivery for in vivo expression of scFv antibody fusion proteins", *Gene Therapy* (1998) 5:770-777.

Jannot, C.B., et al. "Intracellular Expression of a Single-Chain Antibody Directed to the EGFR Leads to Growth Inhibition of Tumor Cells", *Oncogene* (1996) 13(2):275-282.

Lamikanra, A., et al. "In vivo evaluation of an EIAV vector for the systemic genetic delivery of therapeutic antibodies", *Gene Therapy* (2005) 12(12):988-998.

Arafat, W.O., et al. "Effective single chain antibody (scFv) concentrations in vivo via adenoviral vector mediated expression of secretory scFv", *Gene Therapy* (2002) 9(4):256-262.

Myers, K. A., et al. "Targeting Immune Effector Molecules to Human Tumor Cells Through Genetic Delivery of 5T4-Specific scFv Fusion Proteins", *Cancer Gene Therapy* (2002) 9(11):884-896.

Reiger, et al., *Glossary of Genetics and Cytogenetics, Classical and Molecular*. 4th Ed., Springer-Verlag, Berlin, 1976.

Rudikoff, et al., "Single amino acid substitution altering antigen-binding specificity", *Proc. Natl Acad Sci USA* (1982) 79:1979-1983.

Overbeek, Paul A., "Factors affecting transgenic animal production", *Transgenic Animal Technology* (1994) 96-98.

Wall, R.J. "Transgenic Livestock: Progress and Prospects For The Future", *Theriogenology* (1996) 45:57-68.

Houdebine, Louis-Marie, "Production of pharmaceutical proteins from transgenic animals", *J. Biotech* (1994) 34:269-287.

Kappel, Catherine A., et al. "Regulating gene expression in transgenic animals", *Current Opinions in Biotechnology* (1992) 3:548-553.

Cameron, Ewan R., "Recent Advances in Transgenic Technology", *Molecular Biology* (1997) 7:253-265.

Niemann, H. "Transgenic farm animals get off the ground", *Transgenic Research*. (1998) 7:73-75.

Mullins, John H., et al. "Transgenesis in Nonmurine Species", *Hypertension* (1993) 22:630-633.

Mullins, J.J., et al. "Fulminant hypertension in transgenic rats harbouring the mouse *Ren-2* gene", *Nature* (1990) 344:541-544.

Hammer, Robert E., et al. "Spontaneous Inflammatory Disease in Transgenic Rats Expressing HLA-B27 and Human $\beta_2$m: An Animal Model of HLA-B27-Associated Human Disorders", *Cell* (1990) 63:1099-1112.

Mullins, J.J., et al. "Expression of the DBA/2J *Ren-2* gene in the adrenal gland of transgenic mice", *EMBO Journal* (1989) 8(13):4065-4072.

Taurog, Joel D., et al. "HLA-B27 in Inbred and Non-Inbred Transgenic Mice", *Journal of Immunology* (1988) 141(11):4020-4023.

Mullins, Linda J., et al. "Transgenesis in the Rat and Larger Mammals", *J. Clin. Invest*. (1996) 98:S37-S40.

Chaudhary, et al. "A rapid method of cloning functional variable-region antibody genes in *Escherichia coli* as single-chain Immunotoxins", *PNAS* (1990) 87:1066-1070.

Promega, *Catalog of Nucleic Acids* (1993/94) p. 215-216.

Forsberg, Göran, et al. Identification of Framework Residues in a Secreted Recombinant Antibody Fragment That Control Production Level and Localization in *Escherichia coli*, *The Journal of Biological Chemistry* (1997) 272(19):12430-12436.

* cited by examiner

FIG. 1

```
  1  GAGGTCCAGC TTCAGCAGTC TGGACCTGAC CTGGTGAAGC CTGGGGCTTC
      E   V   Q   L   Q   Q   S   G   P   D   L   V   K   P   G   A   S

51  AGTGAAGATA TCCTGCAAGG CTTCTGGTTA CTCATTCACT GGCTACTACA
      V   K   I   S   C   K   A   S   G   Y   S   F   T   G   Y   Y

101  TGCACTGGGT GAAGCAGAGC CATGGAAAGA GCCTTGAGTG GATTGGACGT
      M   H   W   V   K   Q   S   H   G   K   S   L   E   W   I   G   R

151  ATTAATCCTA ACAATGGTGT TACTCTCTAC AACCAGAAAT TCAAGGACAA
      I   N   P   N   N   G   V   T   L   Y   N   Q   K   F   K   D   K

201  GGCCATATTA ACTGTAGACA AGTCATCCAC CACAGCCTAC ATGGAGCTCC
      A   I   L   T   V   D   K   S   S   T   T   A   Y   M   E   L

251  GCAGCCTGAC ATCTGAGGAC TCTGCGGTCT ATTACTGTGC AAGATCTACT
      R   S   L   T   S   E   D   S   A   V   Y   Y   C   A   R   S   T

301  ATGATTACGA ACTATGTTAT GGACTACTGG GGTCAAGTAA CCTCAGTCAC
      M   I   T   N   Y   V   M   D   Y   W   G   Q   V   T   S   V   T

351  CGTCTCCTCA GGTGGTGGTG GGAGCGGTGG TGGCGGCACT GGCGGCGGCG
      V   S   S   G   G   G   G   S   G   G   G   G   T   G   G   G

401  GATCTAGTAT TGTGATGACC CAGACTCCCA CATTCCTGCT TGTTTCAGCA
      G   S   S   I   V   M   T   Q   T   P   T   F   L   L   V   S   A

451  GGAGACAGGG TTACCATAAC CTGCAAGGCC AGTCAGAGTG TGAGTAATGA
      G   D   R   V   T   I   T   C   K   A   S   Q   S   V   S   N   D

501  TGTAGDTTGG TACCAACAGA AGCCAGGGCA GTCTCCTACA CTGCTCATAT
      V   A   W   Y   Q   Q   K   P   G   Q   S   P   T   L   L   I

551  CCTATACATC CAGTCGCTAC GCTGGAGTCC CTGATCGCTT CATTGGCAGT
      S   Y   T   S   S   R   Y   A   G   V   P   D   R   F   I   G   S

601  GGATATGGGA CGGATTTCAC TTTCACCATC AGCACTTTGC AGGCTGAAGA
      G   Y   G   T   D   F   T   F   T   I   S   T   L   Q   A   E   D

651  CCTGGCAGTT TATTTCTGTC AGCAAGATTA TAATTCTCCT CCGACGTTCG
      L   A   V   Y   F   C   Q   Q   D   Y   N   S   P   P   T   F

701  GTGGAGGCAC CAAGCTGGAA ATCAAACGG
      G   G   G   T   K   L   E   I   K   R
```

FIG. 2

| | | | | | |
|---|---|---|---|---|---|
| ATGGGCCACA | CACGGAGGCA | GGGAACATCA | CCATCCAAGT | GTCCATACCT | 50 |
| M G H | T R R Q | G T S | P S K | C P Y L | |
| CAATTTCTTT | CAGCTCTTGG | TGCTGGCTGG | TCTTTCTCAC | TTCTGTTCAG | 100 |
| N F F | Q L L | V L A G | L S H | F C S | |
| GTGTTATCCA | CGTGACCAAG | GAAGTGAAAG | AAGTGGCAAC | GCTGTCCTGT | 150 |
| G V I H | V T K | E V K | E V A T | L S C | |
| GGTCACAATG | TTTCTGTTGA | AGAGCTGGCA | CAAACTCGCA | TCTACTGGCA | 200 |
| G H N | V S V E | E L A | Q T R | I Y W Q | |
| AAAGGAGAAG | AAAATGGTGC | TGACTATGAT | GTCTGGGGAC | ATGAATATAT | 250 |
| K E K | K M V | L T M M | S G D | M N I | |
| GGCCCGAGTA | CAAGAACCGG | ACCATCTTTG | ATATCACTAA | TAACCTCTCC | 300 |
| W P E Y | K N R | T I F | D I T N | N L S | |
| ATTGTGATCC | TGGCTCTGCG | CCCATCTGAC | GAGGGCACAT | ACGAGTGTGT | 350 |
| I V I | L A L R | P S D | E G T | Y E C V | |
| TGTTCTGAAG | TATGAAAAAG | ACGCTTTCAA | GCGGGAACAC | CTGGCTGAAG | 400 |
| V L K | Y E K | D A F K | R E H | L A E | |
| TGACGTTATC | AGTCAAAGCT | GACTTCCCTA | CACCTAGTAT | ATCTGACTTT | 450 |
| V T L S | V K A | D F P | T P S I | S D F | |
| GAAATTCCAA | CTTCTAATAT | TAGAAGGATA | ATTTGCTCAA | CCTCTGGAGG | 500 |
| E I P | T S N I | R R I | I C S | T S G G | |
| TTTTCCAGAG | CCTCACCTCT | CCTGGTTGGA | AAATGGAGAA | GAATTAAATG | 550 |
| F P E | P H L | S W L E | N G E | E L N | |
| CCATCAACAC | AACAGTTTCC | CAAGATCCTG | AAACTGAGCT | CTATGCTGTT | 600 |
| A I N T | T V S | Q D P | E T E L | Y A V | |
| AGCAGCAAAC | TGGATTTCAA | TATGACAACC | AACCACAGCT | TCATGTGTCT | 650 |
| S S K | L D F N | M T T | N H S | F M C L | |
| CATCAAGTAT | GGACATTTAA | GAGTGAATCA | GACCTTCAAC | TGGAATACAA | 700 |
| I K Y | G H L | R V N Q | T F N | W N T | |
| CCAAGCAAGA | GCATTTTCCT | GATGGAGGCG | GGGGATCCGA | GGTCCAGCTT | 750 |
| T K Q E | H F P | D G G | G G S E | V Q L | |

```
CAGCAGTCTG GACCTGACCT GGTGAAGCCT GGGGCTTCAG TGAAGATATC    800
 Q  Q  S    G  P  D  L    V  K  P    G  A  S    V  K  I  S

CTGCAAGGCT TCTGGTTACT CATTCACTGG CTACTACATG CACTGGGTGA    850
 C  K  A    S  G  Y    S  F  T    G  Y  Y  M    H  W  V

AGCAGAGCCA TGGAAAGAGC CTTGAGTGGA TTGGACGTAT TAATCCTAAC    900
 K  Q  S  H    G  K  S    L  E  W    I  G  R    I  N  P  N

AATGGTGTTA CTCTCTACAA CCAGAAATTC AAGGACAAGG CCATATTAAC    950
 N  G  V    T  L  Y  N    Q  K  F    K  D  K    A  I  L  T

TGTAGACAAG TCATCCACCA CAGCCTACAT GGAGCTCCGC AGCCTGACAT    1000
 V  D  K    S  S  T    T  A  Y  M    E  L  R    S  L  T

CTGACGACTC TGCGGTCTAT TACTGTGCAA GATCTACTAT GATTACGAAC    1050
 S  E  D  S    A  V  Y    Y  C  A    R  S  T  M    I  T  N

TATGTTATGG ACTACTGGGG TCAAGTAACC TCAGTCACCG TCTCCTCAGG    1100
 Y  V  M    D  Y  W  G    Q  V  T    S  V  T    V  S  S  G

TGGTGGTGGG AGCGGTGGTG GCGGCACTGG CGGCGGCGGA TCTAGTATTG    1150
 G  G  G    S  G  G    G  G  T    G  G  G    S  S  I

TGATGACCCA GACTCCCACA TTCCTGCTTG TTTCAGCAGG AGACAGGGTT    1200
 V  M  T  Q    T  P  T    F  L  L    V  S  A  G    D  R  V

ACCATAACCT GCAAGGCCAG TCAGAGTGTG AGTAATGATG TAGCTTGGTA    1250
 T  I  T    C  K  A  S    Q  S  V    S  N  D    V  A  W  Y

CCAACAGAAG CCAGGGCAGT CTCCTACACT GCTCATATCC TATACATCCA    1300
 Q  Q  K    P  G  Q    S  P  T  L    L  I  S    Y  T  S

GTCGCTACGC TGGAGTCCCT GATCGCTTCA TTGGCAGTGG ATATGGGACG    1350
 S  R  Y  A    G  V  P    D  R  F    I  G  S  G    Y  G  T

GATTTCACTT TCACCATCAG CACTTTGCAG GCTGAAGACC TGGCAGTTTA    1400
 D  F  T    F  T  I  S    T  L  Q    A  E  D    L  A  V  Y

TTTCTGTCAG CAAGATTATA ATTCTCCTCC GACGTTCGGT GGAGGCACCA    1450
 F  C  Q    Q  D  Y    N  S  P  P    T  F  G  G    G  T

AGCTGGAAAT CAAATAA
 K  L  E  I  K
```

FIG. 2 CONT'D

```
1    ATGGGACTGA GTAACATTCT CTTTGTGATG GCCTTCCTGC TCTCTGGTGC
      M  G  L   S  N  I  L   F  V  M    A  F  L    L  S  G  A

51   TGCTCCTCTG AAGATTCAAG CTTATTTCAA TGAGACTGCA GACCTGCCAT
      A  P  L   K  I  Q    A  Y  F  N  E  T  A    D  L  P

101  GCCAATTTGC AAACTCTCAA AACCAAAGCC TGAGTGAGCT AGTAGTATTT
      C  Q  F   A  N  S  Q  N  Q  S    L  S  E  L   V  V  F

151  TGGCAGGACC AGGAAAACTT GGTTCTGAAT GAGGTATACT TAGGCAAAGA
      W  Q  D    Q  E  N  L   V  L  N   E  V  Y    L  G  K  E

201  GAAATTTGAC AGTGTTCATT CCAAGTATAT GGGCCGCACA AGTTTTGATT
      K  F  D   S  V  H    S  K  Y  M   G  R  T    S  F  D

251  CGGACAGTTG GACCCTGAGA CTTCACAATC TTCAGATCAA GGACAAGGGC
      S  D  S  W   T  L  R    L  H  N   L  Q  I  K   D  K  G

301  TTGTATCAAT GTATCATCCA TCACAAAAAG CCCACAGGAA TGATTCGCAT
      L  Y  Q   C  I  I  H   H  K  K   P  T  G   M  I  R  I

351  CCACCAGATG AATTCTGAAC TGTCAGTGCT TGCTAACTTC AGTCAACCTG
      H  Q  M    N  S  E   L  S  V  L   A  N  F    S  Q  P

401  AAATAGTACC AATTTCTAAT ATAACAGAAA ATGTGTACAT AAATTTGACC
      E  I  V  P   I  S  N    I  T  E   N  V  Y  I   N  L  T

451  TGCTCATCTA TACACGGTTA CCCAGAACCT AAGAAGATGA GTGTTTTGCT
      C  S  S    I  H  G  Y   P  E  P    K  K  M   S  V  L  L

501  AAGAACCAAG AATTCAACTA TCGAGTATGA TGGTATTATG CAGAAATCTC
      R  T  K   N  S  T    I  E  Y  D   G  I  M   Q  K  S

551  AAGATAATGT CACAGAACTG TACGACGTTT CCATCAGCTT GTCTGTTTCA
      Q  D  N  V   T  E  L   Y  D  V    S  I  S  L   S  V  S

601  TTCCCTGATG TTACGAGCAA TATGACCATC TTCTGTATTC TGGAAACTGA
      F  P  D   V  T  S  N   M  T  I    F  C  I    L  E  T  D

651  CAAGACGCGG CTTTTATCTT CACCTTTCTC TATAGAGCTT GAGGACCCTC
      K  T  R   L  L  S    S  P  F  S   I  E  L    E  D  P

701  AGCCTCCCCC AGACCACATT CCTGGAGGCG GGGATCC
      Q  P  P  P   D  H  I   P  G  G   G  G  S
```

```
atggcttgca attgtcagtt gatgcaggat acaccactcc tcaagtttcc atgtccaagg 60
ctcattcttc tctttgtgct gctgattcgt ctttcacaag tgtcttcaga tgttgatgaa 120
caactctcca agtcagtgaa agataaggta ttgctgcctt gccgttacaa ctctccgcat 180
gaagatgagt ctgaagaccg aatctactgg caaaaacatg acaaagtggt gctgtctgtc 240
attgctggga aactaaaagt gtggcccgag tataagaacc ggactttata tgacaacact 300
acctactctc ttatcatcct gggcctggtc ctttcagacc ggggcacata cagctgtgtc 360
gttcaaaaga aggaaagagg aacgtatgaa gttaaacact tggctttagt aaagttgtcc 420
atcaaagctg acttctctac ccccaacata actgagtctg aaacccatc tgcagacact 480
aaaaggatta cctgctttgc ttccgggggt ttcccaaagc ctcgcttctc ttggttggaa 540
aatggaagag aattacctgg catcaatacg acaatttccc aggatcctga atctgaattg 600
tacaccatta gtagccaact agatttcaat acgactcgca accacaccat taagtgtctc 660
attaaatatg gagatgctca cgtgtcagag gacttcacct gggaaaaacc cccagaagac 720
cctcctgata gcaagcccgg gggtggtggg agcggtggtg gcggcagtgg cggcggcgga 780
actagtgagg tccagcttca gcagtctgga cctgacctgg tgaagcctgg ggcttcagtg 840
aagatatcct gcaaggcttc tggttactca ttcactggct actacatgca ctgggtgaag 900
cagagccatg gaaagagcct tgagtggatt ggacgtatta atcctaacaa tggtgttact 960
ctctacaacc agaaattcaa ggacaaggcc atattaactg tagacaagtc atccaccaca 1020
gcctacatgg agctccgcag cctgacatct gaggactctg cggtctatta ctgtgcaaga 1080
tctactatga ttacgaacta tgttatggac tactggggtc aagtaacttc agtcaccgtc 1140
tcttcaggtg gtggtgggag cggtggtggc ggcactggcg gcggcggatc tagtattgtg 1200
atgacccaga ctcccacatt cctgcttgtt tcagcaggag acagggttac cataacctgc 1260
aaggccagtc agagtgtgag taatgatgta gcttggtacc aacagaagcc agggcagtct 1320
cctacactgc tcatatccta tacatccagt cgctacgctg gagtccctga tcgcttcatt 1380
ggcagtggat atgggacgga tttcactttc accatcagca tttgcaggc tgaagacctg 1440
gcagtttatt tctgtcagca agattataat tctcctccga cgttcggtgg aggcaccaag 1500
ctggaaatca aacggtaa                                              1518
```

FIG. 6

Leader / 5T4 scFv / HIgG DNA and deduced protein sequence

```
CTCGAGCCACCATGGGATGGAGCTGTATCATCCTCTTCTTGGTAGCAACAGCTACAGGTGTCCACTCCGAGGTCCAGCTG
            M  G  W  S  C  I  I  L  F  L  V  A  T  A  T  G  V  H  S  E  V  Q  L

CAGCAGTCTGGACCTGACCTGGTGAAGCCTGGGGCTTCAGTGAAGATATCCTGCAAGGCTTCTGGTTACTCATTCACTGG
 Q  Q  S  G  P  D  L  V  K  P  G  A  S  V  K  I  S  C  K  A  S  G  Y  S  F  T

CTACTACATGCACTGGGTGAAGCAGAGCCATGGAAAGAGCCTTGAGTGGATTGGACGTATTAATCCTAACAATGGTGTTA
 G  Y  Y  M  H  W  V  K  Q  S  H  G  K  S  L  E  W  I  G  R  I  N  P  N  N  G  V

CTCTCTACAACCAGAAATTCAAGGACAAGGCCATATTAACTGTAGACAAGTCATCCACCACAGCCTACATGGAGCTCCGC
 T  L  Y  N  Q  K  F  K  D  K  A  I  L  T  V  D  K  S  S  T  T  A  Y  M  E  L  R

AGCCTGACATCTGAGGACTCTGCGGTCTATTACTGTGCAAGATCTACTATGATTACGAACTATGTTATGGACTACTGGGG
 S  L  T  S  E  D  S  A  V  Y  Y  C  A  R  S  T  M  I  T  N  Y  V  M  D  Y  W

TCAAGTAACTTCAGTCACCGTCTCTTCAGGTGGTGGTGGGAGCGGTGGTGGCGGCACTGGCGGCGGCGGATCTAGTATTG
 G  Q  V  T  S  V  T  V  S  S  G  G  G  G  S  G  G  G  G  T  G  G  G  G  S  S  I

TGATGACCCAGACTCCCACATTCCTGCTTGTTTCAGCAGGAGACAGGGTTACCATAACCTGCAAGGCCAGTCAGAGTGTG
 V  M  T  Q  T  P  T  F  L  L  V  S  A  G  D  R  V  T  I  T  C  K  A  S  Q  S  V

AGTAATGATGTAGCTTGGTACCAACAGAAGCCAGGGCAGTCTCCTACACTGCTCATATCCTATACATCCAGTCGCTACGC
 S  N  D  V  A  W  Y  Q  Q  K  P  G  Q  S  P  T  L  L  I  S  Y  T  S  S  R  Y

TGGAGTCCCTGATCGCTTCATTGGCAGTGGATATGGGACGGATTTCACTTTCACCATCAGCACTTTGCAGGCTGAAGACC
 A  G  V  P  D  R  F  I  G  S  G  Y  G  T  D  F  T  F  T  I  S  T  L  Q  A  E  D

TGGCAGTTTATTTCTGTCAGCAAGATTATAATTCTCCTCCGACGTTCGGTGGAGGCACCAAGCTTGAAATCAAACGGGCC
 L  A  V  Y  F  C  Q  Q  D  Y  N  S  P  P  T  F  G  G  G  T  K  L  E  I  K  R  A

TCCACCAAGGGCCCATCGGTCTTCCCCCTGGCACCCTCCTCCAAGAGCACCTCTGGGGGCACAGCGGCCCTGGGCTGCCT
 S  T  K  G  P  S  V  F  P  L  A  P  S  S  K  S  T  S  G  G  T  A  A  L  G  C

GGTCAAGGACTACTTCCCCGAACCGGTGACGGTGTCGTGGAACTCAGGCGCCCTGACCAGCGGCGTGCACACCTTCCCCG
 L  V  K  D  Y  F  P  E  P  V  T  V  S  W  N  S  G  A  L  T  S  G  V  H  T  F  P

CTGTCCTACAGTCCTCAGGACTCTACTCCCTCAGCAGCGTGGTGACCGTGCCCTCCAGCAGCTTGGGCACCCAGACCTAC
 A  V  L  Q  S  S  G  L  Y  S  L  S  S  V  V  T  V  P  S  S  S  L  G  T  Q  T  Y

ATCTGCAACGTGAATCACAAGCCCAGCAACACCAAGGTGGACAAGAAAGTTGAGCCCAAATCTTGTGACAAAACTCACAC
 I  C  N  V  N  H  K  P  S  N  T  K  V  D  K  K  V  E  P  K  S  C  D  K  T  H

ATGCCCACCGTGCCCAGCACCTGAACTCCTGGGGGGACCGTCAGTCTTCCTCTTCCCCCCAAAACCCAAGGACACCCTCA
 T  C  P  P  C  P  A  P  E  L  L  G  G  P  S  V  F  L  F  P  P  K  P  K  D  T  L

TGATCTCCCGGACCCCTGAGGTCACATGCGTGGTGGTGGACGTGAGCCACGAAGACCCTGAGGTCAAGTTCAACTGGTAC
 M  I  S  R  T  P  E  V  T  C  V  V  V  D  V  S  H  E  D  P  E  V  K  F  N  W  Y

GTGGACGGCGTGGAGGTGCATAATGCCAAGACAAAGCCGCGGGAGGAGCAGTACAACAGCACGTACCGTGTGGTCAGCGT
 V  D  G  V  E  V  H  N  A  K  T  K  P  R  E  E  Q  Y  N  S  T  Y  R  V  V  S

CCTCACCGTCCTGCACCAGGACTGGCTGAATGGCAAGGAGTACAAGTGCAAGGTCTCCAACAAAGCCCTCCCAGCCCCCA
 V  L  T  V  L  H  Q  D  W  L  N  G  K  E  Y  K  C  K  V  S  N  K  A  L  P  A  P

TCGAGAAAACCATCTCCAAAGCCAAAGGGCAGCCCCGAGAACCACAGGTGTACACCCTGCCCCCATCCCGGGATGAGCTG
 I  E  K  T  I  S  K  A  K  G  Q  P  R  E  P  Q  V  Y  T  L  P  P  S  R  D  E  M

ACCAAGAACCAGGTCAGCCTGACCTGCCTGGTCAAAGGCTTCTATCCCAGCGACATCGCCGTGGAGTGGGAGAGCAATGG
 T  K  N  Q  V  S  L  T  C  L  V  K  G  F  Y  P  S  D  I  A  V  E  W  E  S  N

GCAGCCGGAGAACAACTACAAGACCACGCCTCCCGTGCTGGACTCCGACGGCTCCTTCTTCCTCTATAGCAAGCTCACCG
 G  Q  P  E  N  N  Y  K  T  T  P  P  V  L  D  S  D  G  S  F  F  L  Y  S  K  L  T

TGGACAAGAGCAGGTGGCAGCAGGGGAACGTCTTCTCATGCTCCGTGATGCATGAGGCTCTGCACAACCACTACACGCAG
 V  D  K  S  R  W  Q  Q  G  N  V  F  S  C  S  V  M  H  E  A  L  H  N  H  Y  T  Q

AAGAGCCTCTCCCTGTCCCCGGGTAAATGACTCGAG
 K  S  L  S  L  S  P  G  K
```

FIG. 7

```
ctcgagccac catgggatgg agctgtatca tcctcttctt ggtagcaaca gctacaggtg  60
tccactccga ggtccagctg cagcagtctg gacctgacct ggtgaagcct ggggcttcag 120
tgaagatatc ctgcaaggct tctggttact cattcactgg ctactacatg cactgggtga 180
agcagagcca tggaaagagc cttgagtgga ttggacgtat taatcctaac aatggtgtta 240
ctctctacaa ccagaaattc aaggacaagg ccatattaac tgtagacaag tcatccacca 300
cagcctacat ggagctccgc agcctgacat ctgaggactc tgcggtctat tactgtgcaa 360
gatctactat gattacgaac tatgttatgg actactgggg tcaagtaact tcagtcaccg 420
tctcttcagg tggtggtggg agcggtggtg gcggcactgg cggcggcgga tctagtattg 480
tgatgaccca gactcccaca ttcctgcttg tttcagcagg agacagggtt accataacct 540
gcaaggccag tcagagtgtg agtaatgatg tagcttggta ccaacagaag ccagggcagt 600
ctcctacact gctcatatcc tatacatcca gtcgctacgc tggagtccct gatcgcttca 660
ttggcagtgg atatgggacg gatttcactt tcaccatcag cactttgcag gctgaagacc 720
tggcagttta tttctgtcag caagattata attctcctcc gacgttcggt ggaggcacca 780
agcttgaaat caaacgggcc tccacacaga gcccatccgt cttcccttg acccgctgct 840
gcaaaaacat tcctccaat gccacctccg tgactctggg ctgcctggcc acgggctact 900
tcccggagcc ggtgatggtg acctgggaca caggctccct caacgggaca actatgacct 960
taccagccac caccctcacg ctctctggtc actatgccac catcagcttg ctgaccgtct 1020
cgggtgcgtg gccaagcag atgttcacct gccgtgtggc acacactcca tcgtccacag 1080
actgggtcga caacaaaacc ttcagcgtct gctccaggga cttcaccccg ccaccgtga 1140
agatcttaca gtcgtcctgc gacggcggcg ggcacttccc ccgaccatc cagctcctgt 1200
gcctcgtctc tgggtacacc ccaggactat caacatcac ctggctggag gacgggcagg 1260
tcatggacgt ggacttgtcc accgcctcta ccacgcagga gggtgagctg gcctccacac 1320
aaagcgagct caccctcagc cagaagcact ggctgtcaga ccgcacctac acctgccagg 1380
tcacctatca aggtcacacc tttgaggaca gcaccaagaa gtgtgcagat tccaacccga 1440
gagggtgag cgcctaccta agccggccca gcccgttcga cctgttcatc cgcaagtcgc 1500
ccacgatcac ctgtctggtg gtggacctgg cacccagcaa gggggacgtg aacctgacct 1560
ggtcccgggc cagtgggaag cctgtgaacc actccaccag aaaggaggag aagcagcgca 1620
atggcacgtt aaccgtcacg tccaccctgc cggtgggcac ccgagactgg atcgagcggg 1680
agacctacca gtgcagggtg acccaccccc acctgccagg gcctcatg cggtccacga 1740
ccaagaccag cggcccgcgt gctgcccgg aagtctatgc gtttgcgacg ccggagtggc 1800
cggggagccg ggacaagcgc accctcgcct gctgatcca gaacttcatg cctgaggaca 1860
tctcggtgca gtggctgcac aacgaggtgc agctcccgga cgcccggcac agcacgacgc 1920
agccccgcaa gaccaagggc tccggcttct tcgtcttcag ccgcctggag gtgaccaggg 1980
ccgaatggga gcagaaagat gagttcatct gccgtgcagt ccatgaggca gcgagccct 2040
cacagaccgt ccagcgagcg gtgtctgtaa atcccggtaa atgagagctc           2090
```

FIG. 8

```
atggcttgca attgtcagtt gatgcaggat acaccactcc tcaagtttcc atgtccaagg  60
ctcattcttc tctttgtgct gctgattcgt ctttcacaag tgtcttcaga tgttgatgaa 120
caactgtcca agtcagtgaa agataaggta ttgctgcctt gccgttacaa ctctccgcat 180
gaagatgagt ctgaagaccg aatctactgg caaaaacatg acaaagtggt gctgtctgtc 240
attgctggga actaaaagt gtggcccgag tataagaacc ggactttata tgacaacact 300
acctactctc ttatcatcct gggcctggtc ctttcagacc ggggcacata cagctgtgtc 360
gttcaaaaga aggaagagg aacgtatgaa gttaaacact ggctttagt aaagttgtcc 420
atcaaagctg acttctctac ccccaacata actgagtctg aaacccatc tgcagacact 480
aaaaggatta cctgctttgc ttccggggt ttcccaaagc ctcgcttctc ttggttggaa 540
aatggaagag aattacctgg catcaatacg acaatttccc aggatcctga atctgaattg 600
tacaccatta gtagccaact agatttcaat acgactcgca accaccat taagtgtctc 660
attaaatatg gagatgctca cgtgtcagag acttcacct ggaaaaaacc cccagaagac 720
cctcctgata gcaagcccgg gggtggtggg agcggtggtg gcggcagtgg cggcggcgga 780
actagtaata gtgactctga atgtcccctg tccacgatg ggtactgcct ccatgatggt 840
gtgtgcatgt atattgaagc attggacaag tatgcatgca actgtgttgt ggctacatc 900
ggggagcgat gtcagtaccg agacctgaag tggtgggaac tgcgc           945
```

B16-neoTumour Growth pONY8.1SM

FIG. 19
FUSION PROTEIN CONSTRUCTS IN pONY 8.1SM
A. B7-5T4scFv
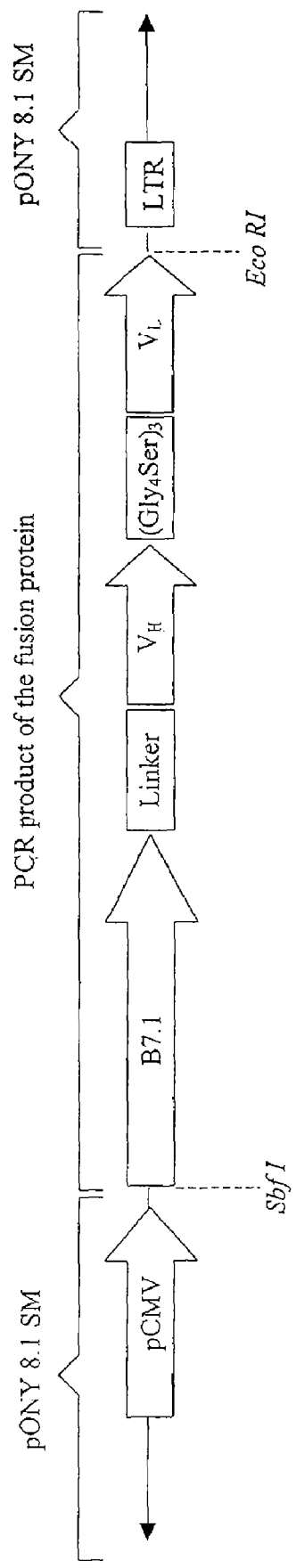
B. L-5T4scFv
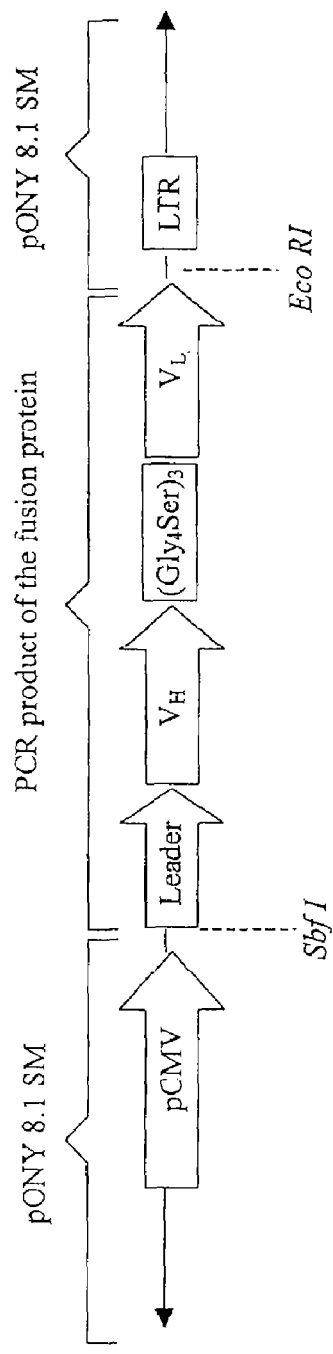

FIG. 20 pKLink – the (Gly$_4$Ser)$_3$ linker in pBluescript II SK (pBS II)

```
        Spe I  Age I                                              Bam HI
Not I   Xba I  CTAGTACCGGTGGTGGTGGGAGCGGTGGTGGTGGGCAGTGGTGGGGGCG            Sma I       Sal I
pBS II         ATGGCCACCACCACCCTCGCCACCACCACCCGTCACCGCCGCCGCCGCCGCCTAG              pBS II
                G  G  G  G  S  G  G  G  G  S  G  G  G  G  S
```

FIG. 21

An scFv and leader sequence in pBSII

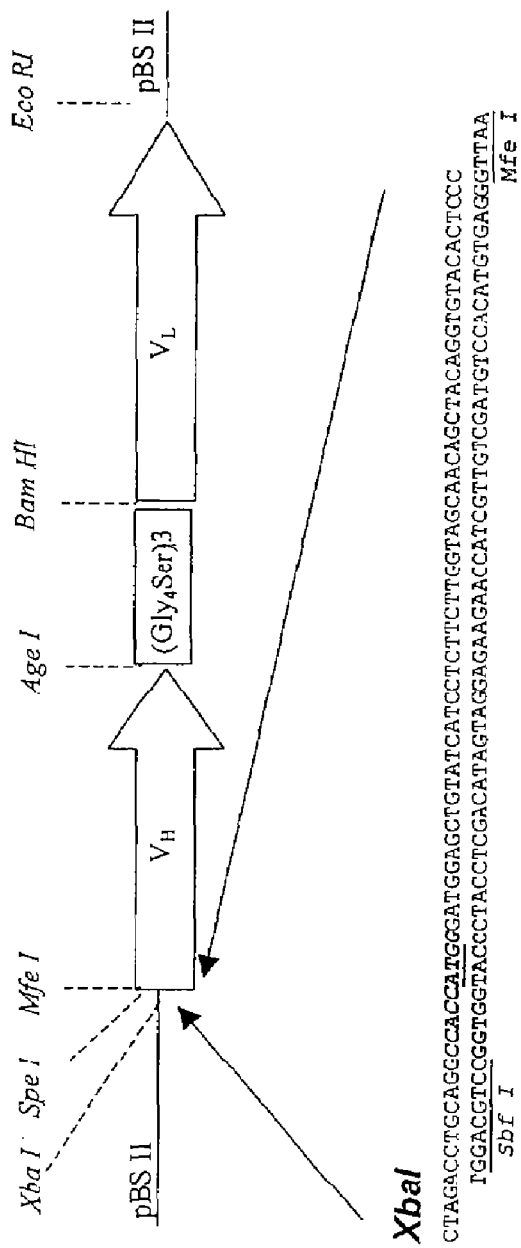

Xbal

CTAGACCTGCAGGCCACCATGGGATGGAGCTGTATCATCCTCTTCTTGGTAGCAACAGCTACAGGTGTACACTCCC
TGGACGTCCGGTGGTACCCTACCTCGACATAGTAGGAGAAGAACCATCGTTGTCGATGTCCACATGTGAGGGTTAA
Sbf I                                                                    Mfe I

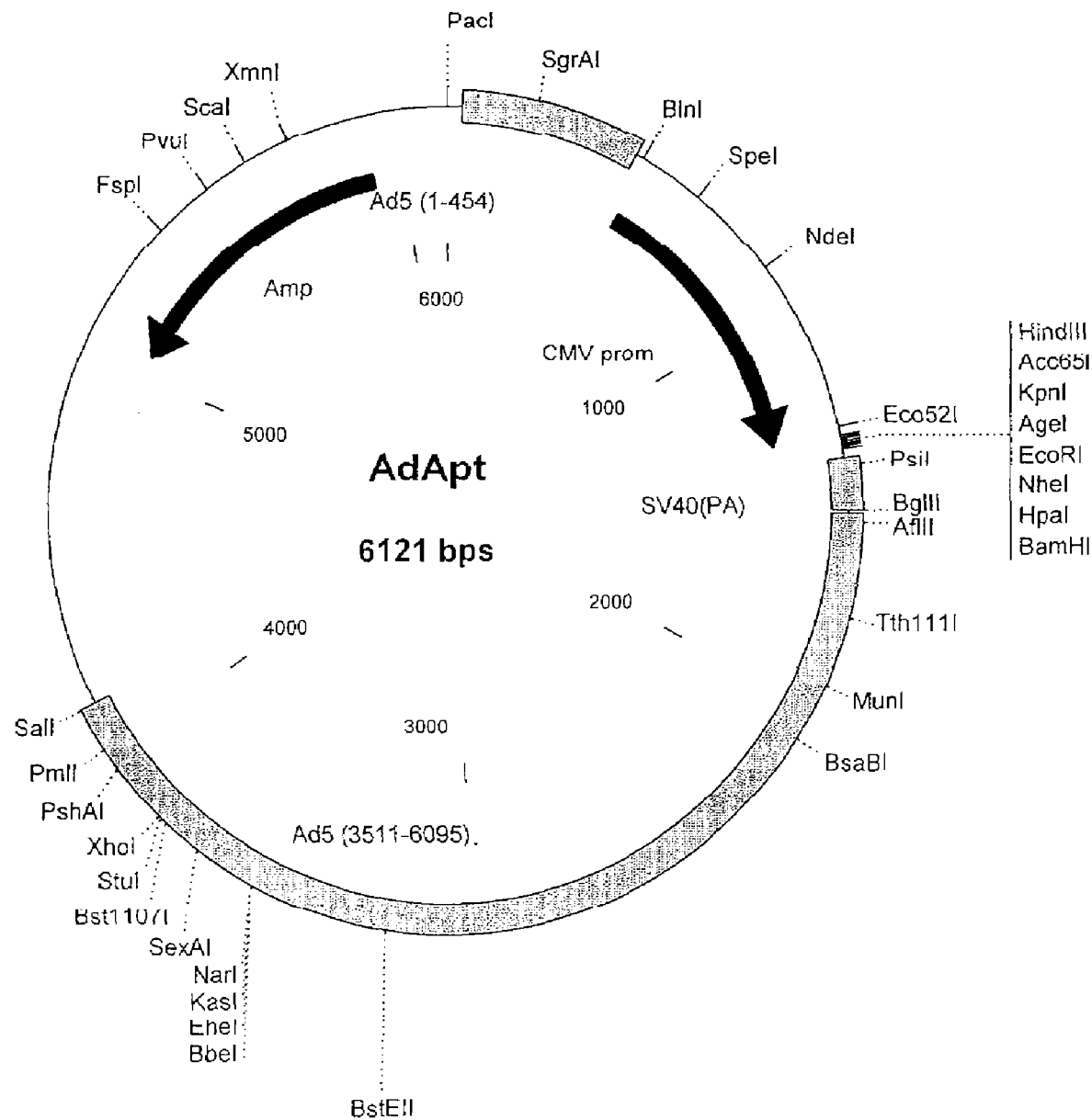

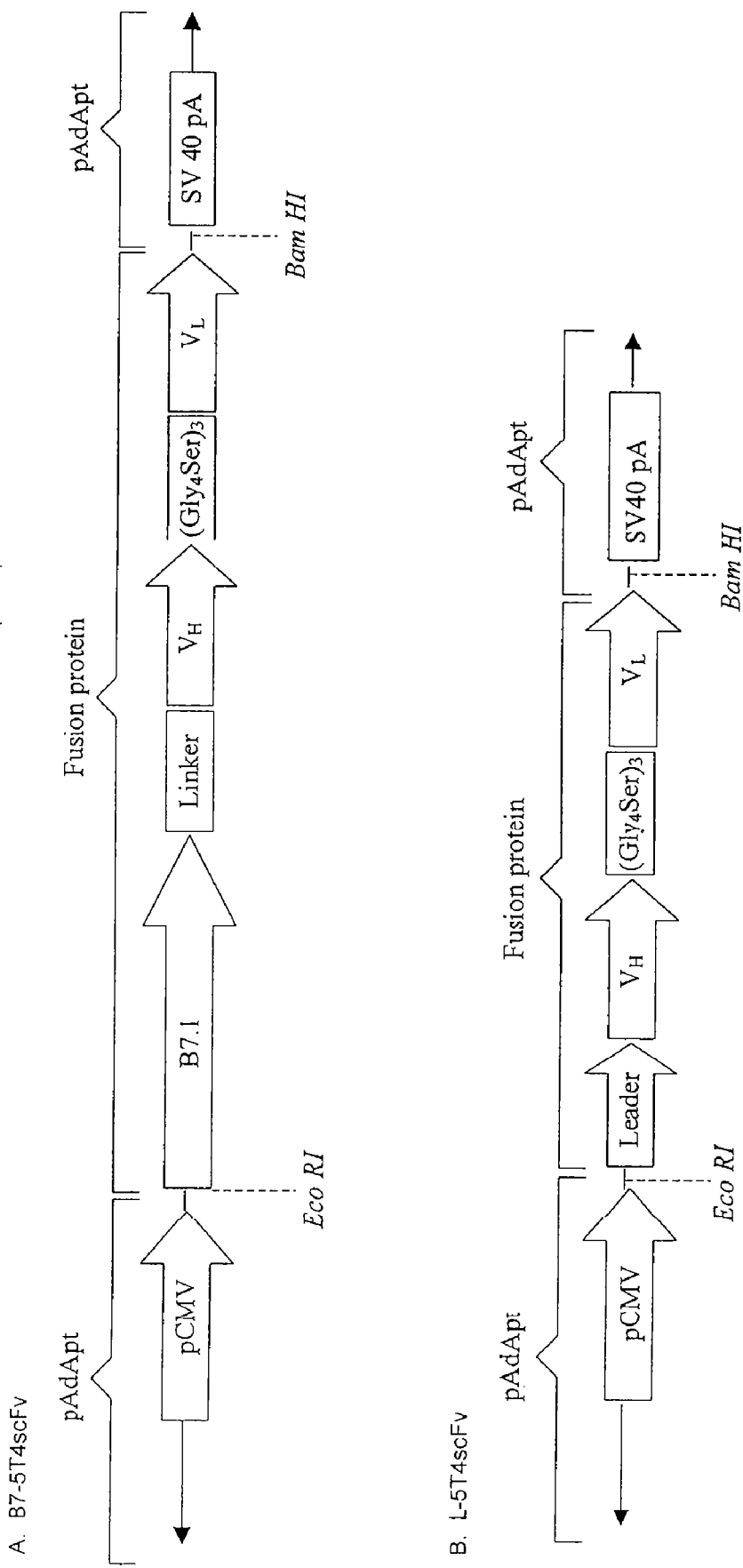

FIG. 26
Canine 5T4 Coding Sequence

```
ATGCCTGGGGGGTGCTCCCGGGGCCCCGCCGCCGGGGACGGGCGGTTGCGGCTGGCGCGGCTGGCGCTGGTGCTCCTGGG   80
 M  P  G  G  C  S  R  G  P  A  A  G  D  G  R  L  R  L  A  R  L  A  L  V  L  L

CTGGGTCTCCTCGTCCTCGCTCACCTCCTGGGCGCCCTCCGCCGCCGCCTCCACGTCGCCGCCGGCCTCCGCGGCGTCCG  160
 G  W  V  S  S  S  L  T  S  W  A  P  S  A  A  A  S  T  S  P  P  A  S  A  A  S

CCCCGCCCCGCTGCCGGGCCAGTGCCCCCAGCCTTGCGAGTGCTCGGAGGCGGCGCGCACGGTCAAGTGCGTTAACCGC   240
 A  P  P  P  L  P  G  Q  C  P  Q  P  C  E  C  S  E  A  A  R  T  V  K  C  V  N  R

AACCTGACCGAGGTGCCCGCGGACCTGCCCCCCTACGTGCGCAACCTCTTCCTCACGGGCAACCAGCTGGCGGTGCTGCC   320
 N  L  T  E  V  P  A  D  L  P  P  Y  V  R  N  L  F  L  T  G  N  Q  L  A  V  L

CCCCGGCGCCTTCGCCCGCCGGCCGCCGCTGGCCGAGCTGGCCGCGCTCAACCTGAGCGGCAGCAGCCTGCGGGAGGTGT   400
 P  P  G  A  F  A  R  R  P  P  L  A  E  L  A  A  L  N  L  S  G  S  S  L  R  E  V

GCGCCGGCGCCTTCGAGCACCTGCCCAGCCTGCGCCAGCTCGACCTCAGCCACAACCCGCTGGGCAACCTCAGCGCCTTC   480
 C  A  G  A  F  E  H  L  P  S  L  R  Q  L  D  L  S  H  N  P  L  G  N  L  S  A  F

GCCTTCGCGGGCAGCGACGCCAGCCGCTCGGGCCCCAGCCCCCTGGTGGAGCTGATGCTGAACCACATCGTGCCCCCCGA   560
 A  F  A  G  S  D  A  S  R  S  G  P  S  P  L  V  E  L  M  L  N  H  I  V  P  P

CGACCGGCGGCAGAACCGGAGCTTCGAGGGCATGGTGGCGGCTGCCCTCCGAGCGGGCCGCGCGCTTCGCGGGCTGCAGT   640
 D  D  R  R  Q  N  R  S  F  E  G  M  V  A  A  A  L  R  A  G  R  A  L  R  G  L  Q

GCCTGGAGCTGGCCGGCAACCGCTTCCTCTACTTGCCTCGCGACGTCCTGGCCCAGCTACCCGGCCTCCGGCACCTGGAC   720
 C  L  E  L  A  G  N  R  F  L  Y  L  P  R  D  V  L  A  Q  L  P  G  L  R  H  L  D

CTGCGCAACAACTCCCTGGTGAGCCTCACCTACGTGTCCTTCCGCAACCTGACGCACTTGGAGAGCCTCCACCTGGAGGA   800
 L  R  N  N  S  L  V  S  L  T  Y  V  S  F  R  N  L  T  H  L  E  S  L  H  L  E

CAACGCCCTCAAGGTCCTTCACAACGCCACCCTGGCGGAGCTGCAGAGCCTGCCCCACGTCCGGGTCTTCCTGGACAACA   880
 D  N  A  L  K  V  L  H  N  A  T  L  A  E  L  Q  S  L  P  H  V  R  V  F  L  D  N

ACCCCTGGGTCTGCGATTGTCACATGGCAGACATGGTGGCCTGGCTCAAGGAGACAGAGGTGGTGCCGGGCAAAGCCGGG   960
 N  P  W  V  C  D  C  H  M  A  D  M  V  A  W  L  K  E  T  E  V  V  P  G  K  A  G

CTCACCTGTGCATTCCCGGAGAAAATGAGGAATCGGGCCCTCTTGGAACTCAACAGCTCCCACCTGGACTGTGACCCTAT  1040
 L  T  C  A  F  P  E  K  M  R  N  R  A  L  L  E  L  N  S  S  H  L  D  C  D  P

CCTCCCTCCATCCCTGCAGACTTCTTATGTCTTCCTAGGTATTGTCTTAGCCCTGATAGGCGCCATCTTCCTACTGGTTT  1120
 I  L  P  P  S  L  Q  T  S  Y  V  F  L  G  I  V  L  A  L  I  G  A  I  F  L  L  V

TGTATTTGAACCGCAAGGGGATAAAGAAGTGGATGCATAACATCAGAGATGCCTGCAGGGATCACATGGAAGGGTATCAC  1200
 L  Y  L  N  R  K  G  I  K  K  W  M  H  N  I  R  D  A  C  R  D  H  M  E  G  Y  H

TACAGATACGAAATCAATGCAGACCCCAGGTTAACAAACCTCAGTTCCAATTCGGATGTCTGA                  1263
 Y  R  Y  E  I  N  A  D  P  R  L  T  N  L  S  S  N  S  D  V
```

ANTIBODIES

REFERENCE TO RELATED APPLICATIONS/INCORPORATION BY REFERENCE

This application is a continuation-in-part of international application PCT/GB00/04317, filed Nov. 13, 2000, designating the U.S., and published on May 25, 2001 as WO 01/36486, which claims priority from PCT/GB99/03859, filed Nov. 18, 1999, Great Britian Application No. 0003527.9, filed Feb. 15, 2000, and Great Britian Application No. 0005071.6, filed Mar. 2, 2000. All of the above-mentioned applications, as well as all documents cited herein and documents referenced or cited in documents cited herein, are hereby incorporated herein by reference.

FIELD OF THE INVENTION

The present invention relates to antibodies.

In particular, the present invention relates to antibodies that recognise a disease associated molecule (DAM).

More particularly, the present invention relates in vitro and in vivo/ex vivo applications of these antibodies in the diagnosis and treatment of diseases associated with a DAM.

BACKGROUND TO THE INVENTION

In certain disease states, a derangement of cellular metabolism can affect the level of expression of one or more DAMs. In some circumstances, this cellular derangement may lead to a change in the levels of expression of the DAM. Thus, each disease causing agent or disease state may have associated with it a DAM which may be crucial in the immune recognition and/or the elimination and/or control of a disease causing agent or disease state in a host organism. In this way, the DAM may be capable of acting as a marker not only for the diagnosis of disease states but also for the accurate staging of the disease profile so that the appropriate therapy may be designed.

A particular example of DAMs which have been well characterised include the tumour-associated antigens (TAAs). A number of oncofoetal or tumour-associated antigens (TAAs) have been identified and characterised in human and animal tumours.

These TAAs include carcinoembryonic antigen (CEA), TAG72, c-erB2, (underglycosylated) MUC-1 and p53, epithelial glycoprotein-2 antigen (EGP-2; also known as EGP40, Ep-CAM, KSA, C017-1A or GA733-2) and the 5T4 antigen. In general, TAAs are antigens which are expressed during foetal development but which are downregulated in adult cells, and are thus normally absent or present only at very low levels in adults. However, during tumourigenesis, tumour cells have been observed to resume expression of TAAs. Thus, it is thought that malignant cells may be distinguished from their non-malignant counterparts by resumption of expression of TAAs. Consequently, application of TAAs for (i) in vitro and/or in vivo/ex vivo diagnosis of tumour disorders; (ii) for imaging and/or immunotherapy of cancer has been suggested and (iii) as indicators of progression of tumour associated disease;

In order to mount a humoral and/or cellular immune response against a particular disease, the host immune system must come in contact with a DAM. In addition to recognising foreign antigens, T cells often need additional stimulation to become fully activated. It is now becoming apparent that two signals are required for activation of naive T-cells by antigen bearing target cells. One signal is an antigen specific signal, delivered through the T-cell receptor and the second signal is an antigen independent or co-stimulatory signal leading to lymphokine products. These additional signals are delivered through other receptors (such as CD28 and CD40L) on the T cell that interact with ligands (such as B7 and CD40) which are present on professional antigen presenting cells (APCs), such as dendritic cells and macrophages, but which are absent from other cells. These co-stimulatory ligands are often referred to as co-stimulatory molecules.

By way of example, the B7 family (namely B7.1, B7.2, and possibly B7.3) represent a recently discovered, but important group of co-stimulatory molecules. B7.1 and B7.2 are both member of the Ig gene superfamily. If a T lymphocyte encounters an antigen alone, without co-stimulation by B7, it will respond with either anergy, or apoptosis (programmed cell death). If the co-stimulatory signal is provided it will respond with clonal expansion against the target antigen. No significant amplification of the immune response against a given antigen is thought to occur without co-stimulation (June et al (Immunology Today 15:321-331, 1994); Chen et al(Immunology Today 14:483-486); Townsend et al (Science 259:368-370)). Freeman et al(J. Immunol. 143:2714-2722, 1989). Azuma et al(Nature 366:76-79, 1993). Thus, it has been postulated that one method for stimulating immune recognition of diseased cells which are poorly immunogenic would be to enhance antigen presentation and co-stimulation of lymphocytes in the presence of the DAM.

By way of example, it has been shown that disease states such as cancer, established tumours may be poorly immunogenic despite the fact that they commonly express DAMs. Transfection of the genes encoding B7-1 and B7-2, either alone or in combination with cytokines, have been shown to enhance the development of immunity to experimental tumours in animal models (e.g. Leong et al. 1997 Int. J. Cancer 71: 476-482; Zitvogel et al. 1996 Eur. J. Immunol. 26:1335-1341; Cayeux et al. 1997 J. Immunol 158:2834-2841). However, in translating these results into a practical treatment for human cancer, there are a number of significant problems to be overcome. A major problem in such studies has been the need to deliver B7 genes in vivo to a large number of cells of the tumour to achieve efficacy. A second problem has been the selective target expression of B7 to the tumour cells to avoid inappropriate immune cell activation directed against other cell types. Some solutions to these problems have been addressed in WO 98/55607 where a tumour interacting protein (TIP) such as a tumour binding protein (TBP) has been used to selectively target a co-stimulatory molecule to tumour cells.

Recombinant DNA technologies have been applied to develop antibodies that recognise DAMs (Hoogenboom et al 1998 Immunotechnology 4: 1-20; and Winter 1998 FEBS Lett 458: 92-94. Recently, there has been considerable interest in using antibody gene libraries to generating antibodies, such as a single chain antibody (ScFv Abs). It is well known that in certain circumstances, there are advantages of using ScFv Abs, rather than whole antibodies. The smaller size of the fragments allows for rapid clearance, and may lead to improved tumour to non-tumour ratios. However, many efforts have failed to produce ScFv Abs of high specificity. Moreover, whole IgGs are regarded as a better format for therapeutic Mabs than ScFc Abs as they are regarded as having an extended serum half life (see Vaughan et al 1998, Nature Biotech 16: 535-539).

The present invention seeks to provide an ScFv Ab raised against a DAM which is useful in the treatment of disease conditions associated with a DAM."

SUMMARY ASPECTS OF THE PRESENT INVENTION

The present invention provides an ScFv Ab (ScFv Ab), capable of recognising a DAM and having a therapeutic effect in diseases associated with a DAM. This ScFv Ab can be directly administered either as a peptide (synthetically or genetically expressed) or as "naked DNA" (for example, in a plasmid) or via a delivery vehicle such as a viral vector comprising the nucleotide sequence encoding the ScFv Ab. For some cases, this ScFv Ab may be more efficacious than a ScFv Ab fused to an secreted co-stimulatory molecule (SCM) such as B7 or IgG. Using an ScFv Ab was not an obvious choice as a therapeutic agent, for the treatment of diseases such as cancer, especially as one would expect that a fusion protein comprising a SCM fused to an ScFv would perform better than an ScFv alone.

The present invention is advantageous for the following reasons:

(i) it provides an ScFv Ab capable of recognising a DAM. For some cases, it has a greater therapeutic effect than an ScFv Ab which is fused to a SCM such as B7 or an immunoglobulin such as IgG;

(ii) it provides a high affinity ScFv Ab which has applications in:

(a) in vitro and in vivo/ex vivo diagnosis and therapy;

(b) imaging and the treatment of cells expressing the a DAM;

(c) prevention and/or treatment of different human diseases such as carcinomas when the ScFv Ab is used either alone or in combination with suitable diagnostic and/or therapeutically useful agents;

(d) studies relating to the isolation and/or purification of a DAM to which the ScFv Abs specifically binds; and (e) providing building blocks for further rational therapeutic ScFv Ab design and screens for ScFv Abs capable of binding to target DAMs and/or screens for DAMs capable of binding to target ScFv Abs.

DETAILED ASPECTS OF THE INVENTION

Other aspects of the present invention are presented in the accompanying claims and in the following description and drawings. These aspects are presented under separate section headings. However, it is to be understood that the teachings under each section are not necessarily limited to that particular section heading.

ScFv Antibody

In one aspect, the present invention provides a recombinant ScFv Ab that recognises a DAM.

As used herein, the term "ScFv Ab" means an antibody capable of recognising a DAM antigen which has a light chain variable region (VL) and a heavy chain variable (VH) region. The VH and VL partner domains are typically linked/joined via a flexible oligopeptide/peptide linker. The VH and VL partner domains may be connected in the order of VH followed by VL or VL followed by VH. Typically, the sequences may be connected via a linker sequence in the order VH-linker-VL or VL-linker-VH. As used herein, the term includes fragments of proteolytically-cleaved or recombinantly-prepared portions of an ScFv Ab molecule that are capable of selectively reacting with or recognising a DAM. Non limiting examples of such proteolytic and/or recombinant fragments include chimeric ScFv antibodies which, for the purposes of this invention, may refer to an ScFv Ab having either a or both heavy and light chain variable regions (VH and VL) encoded by a nucleotide sequence derivable from a mammalian immunoglobulin gene other than a human immunoglobulin gene and either a or both heavy and light chain encoded by a nucleotide sequence derivable from a human immunoglobulin gene. The ScFv Ab may be covalently or non-covalently linked to another entity (such as another ScFv Ab) to form antibodies having two or more binding sites. For example, one ScFv Ab could bind to to a DAM, such as 5T4, and the second ScFv Ab could bind to an immune enhancer molecule.

In accordance with the present invention, reference to the term "ScFv Ab" includes but is not limited to reference to the peptide per se also as well the peptide as part of a fusion protein as well as the nucleotide sequence encoding the peptide and/or the nucleotide sequence encoding the fusion protein. The peptide per se and/or fusion protein may be a synthetic peptide. Alternatively, the peptide and/or fusion protein may be a genetically expressed/recombinant peptide/fusion protein. For some applications, the term "ScFv Ab means peptide per se. The term "ScFv Ab" also includes an ScFv Ab with a secretion leader (L) sequence which is designated herein as LScFv.

As used herein, the term "variable region" refers to the variable region, or domain, of the light chain (VL) and heavy chain (VH) which contain the determinants for binding recognition specificity and for the overall affinity of the ScFv Ab for a DAM. The variable domains of each pair of light (VL) and heavy chains (VH) are involved in antigen recognition and form the antigen binding site. The domains of the light and heavy chains have the same general structure and each domain has four framework (FR) regions, whose sequences are relatively conserved, connected by three complementarity determining regions (CDRs). The FR regions maintain the structural integrity of the variable domain. The CDRs are the polypeptide segments within the variable domain that mediate binding of an antigen such as a DAM.

Preferably the affinity ($K_D$) of the ScFv Ab of the present invention for the 5T4 antigen is from about $5\times10^{-10}$ to about $10\times10^{-10}$.

Preferably the affinity ($K_D$) of the ScFv Ab of the present invention for the 5T4 antigen is from about $6\times10^{-10}$ to about $9\times10^{-10}$.

Preferably the affinity ($K_D$) of the ScFv Ab of the present invention for the 5T4 antigen is from about $7\times10^{-10}$ to about $8\times10^{-10}$.

Preferably the affinity ($K_D$) of the ScFv Ab of the present invention for the 5T4 antigen is about $7.9\times10^{-10}$. The $K_D$ of the ScFvAb is measured using BIAevaluation software (Pharmacia).

As used herein, the term "off-rate" means the dissociation rate ($k_{off}$) of a ScFv Ab from an antigen. In the context of the present invention, it is measured using BIAevaluation software (Pharmacia). A low off rate is desirable as it reflects the affinity of an Fab fragment for an antigen such as a DAM.

As used herein, the term "affinity" is defined in terms of the dissociation rate or off-rate ($k_{off}$) of a ScFv Ab from a DAM antigen. The lower the off-rate the higher the affinity that a ScFv Ab has for an antigen such as a DAM.

DAM

As used herein, the term "DAM" can include but is not limited to biological response modifiers which include but are not limited to immunomodulators, cytokines, growth factors, cell surface receptors, hormones, circulatory molecule, inflammatory cytokines, and pathogenic agents such a viruses, bacteria, parasites or yeast. Examples of these biological response modifiers include but are not limited to ApoE, Apo-SAA, BDNF, Cardiotrophin-1, EGF, ENA-78, Eotaxin, Eotaxin-2, Exodus-2, FGF-acidic, FGF-basic, fibroblast growth factor-10 (Marshall 1998 Nature Biotechnology 16: 129), FLT3 ligand (Kimura et al. (1997), Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein (Marshall 1998 ibid), M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-i (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNIL-1, TPO, VEGF, GCP-2, GRO/MGSA, GRO-β, and GRO-γ.

Examples of pathogenic agents can include but are not limited to viruses, bacteria and parasites and yeasts. By way of example, pathogenic viruses include but are not limited to human immunodeficiency virus (HIV), influenza, herpes simplex, human papilloma virus, equine encephalitis virus, hepatitis, feline leukaemia virus, canine distemper and rabies virus, influenza, poxviruses, fowl pox virus (FPV), canarypox virus, entomopox virus, vaccinia virus deficient in a DNA replication enzyme, Alphavirus, adenovirus, herpesvirus, Venezuelan equine encephalitis virus (VEE). Examples of pathogenic bacteria can include but are not limited to *Chlamydia, Mycobacteria, Plasmodium Falciparum, Legioniella, Pseudomonas aeruginosa, Salmonella typhimurium, Streptococcus pyogenes, Neisseria gonorrheae, Corynebacterium diphtheriae, Clostridium tetani, Vibrio cholerae, Listeria monocytogenes, Clostridium perfringens, Escherichia coli, Yersinia pestis, Streptococcus pneumoniae* and *S. Typhimurium* Examples of pathogenic parasites include but are not limited to *Trypanosoma, Trypanosoma cruzi, Leishmania, Leishmania donovani, L. tropica, L. mexicana, L. Braziliensis, Giardia, Giardia lamblia, Trichomonas, Entamoeba, Naegleria, Acanthamoeba, Acanthamoeba castellanii, A. culbertsoni* and other species, *Plasmodium, Toxoplasma, Toxoplasma gondii, Cryptosporidium, Cryptosporidium parvum, Isospora, Isospora belli, Naegleria, Naegleria fowleri, Balantidium, Balantidium coli, Babesia, Schistosoma, Toxiplasma* and *Toxocara canis*. Examples of pathogenic yeasts include *Aspergillus* and invasive *Candida*. In a preferred embodiment the pathogenic microorganism is an intracellular organism.

Preferably the DAM is an intracellular pathogenic agent.

Preferably the DAM is a disease associated cell surface molecule (DACSM).

In accordance with the present invention the DACSM can include but is not limited to a receptor for adhesive proteins such as growth factor receptors. Examples of growth factor receptors include but are not limited to ApoE, Apo-SAA, BDNF, Cardiotrophin-1, EGF, ENA-78, Eotaxin, Eotaxin-2, Exodus-2, FGF-acidic, FGF-basic, fibroblast growth factor-10 (Marshall 1998 Nature Biotechnology 16: 129) FLT3 ligand (Kimura et al (1997), Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein (Marshall 1998 ibid), M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNIL-1, TPO, VEGF, GCP-2, GRO/MGSA, GRO-β, GRO-γ, HCC1, 1-309. A non-exhaustive list of growth factor receptors can be found on pages 392-297 Molecular Biology and Biotechnology (Ed R A Meyers 1995 VCH Publishers Inc).; a plasminogen activator; a metalloproteinase (such as colllagenase), a mucin; a glycoprotein; an antigen restricted in its tissue distribution; and/or a cell surface molecule which plays a role in tumour cell growth, migration or metastasis, (such as a 5T4 antigen, a tumour specific carbohydrate moiety or an oncofetal antigen). The term DACSM may also includes antigenic determinants.

Antigenic Determinant

As used herein, the term "antigenic determinant" refers to any antigen which is associated with a disease or a disorder. By way of example, the antigenic determinant may also be derived from pathogenic agents associated with diseased cells, such as tumour cells, which multiply unrestrictedly in an organism and may thus lead to pathological growths. Examples of such pathogenic agents are described in Davis, B. D. et al(Microbiology, 3rd ed., Harper International Edition). The antigenic determinant may be an antigen and/or an immunodominant epitope on an antigen. By way of example, the antigenic determinant may include tumour associated antigens (TAA) which may serve as targets for the host immune system and elicit responses which result in tumour destruction.

TAA

The term "tumour associated antigen (TAA)" is used herein to refer to any TAA or antigenic peptide thereof. The antigen being one that is expressed by the tumour itself or cells associated with the tumour such as parenchymal cells or those of the associated vasculature. The term "tumour associated antigen (TAA)" includes antigens that distinguish the tumour cells from their normal cellular counterparts where they may be present in trace amounts.

Examples of TAAs include but are not limited to MART-1 (Melanoma Antigen Recognised by T cells-1) MAGE-1, MAGE-3, 5T4, gp100, Carcinoembryonic antigen (CEA), prostate-specific antigen (PSA), MUCIN (MUC-1), tyrosinase. Particularly preferred TAAs are cell surface molecules as these are positioned for recognition by elements of the immune system and are excellent targets for therapy such as therapy and/or immunotherapy. The present invention is in no way limited to antigenic determinants encoding the above listed TAAs. Other TAAs may be identified, isolated and cloned by methods known in the art such as those disclosed in U.S. Pat. No. 4,514,506.

5T4 TAA

The TAA 5T4 (see WO 89/07947) has been extensively characterised. It is a 72 kDa glycoprotein expressed widely in carcinomas, but having a highly restricted expression pattern in normal adult tissues. It appears to be strongly correlated to metastasis in colorectal and gastric cancer. The full nucleic acid sequence of human 5T4 is known (Myers et al., 1994 J Biol Chem 169: 9319-24).

Co-Stimulatory Molecules

In order to respond to a DAM, lymphocytes require at least two distinct signals to activate their effector functions (Bretscher and Cohn 1970 Science 169: 1042-1049; Crabtree 1989 Science 243: 355-361). The primary signal is specific for antigen. Stimulation of the primary signal in isolation normally leads to apoptosis (programmed cell death) of the lymphocyte or leads to the establishment of a state of sustained unresponsiveness or anergy (Weiss et al. supra). In order to achieve activation of the lymphocyte, accessory signals are required which may be delivered by cytokines or by cell-surface co-stimulatory ligands present on antigen-presenting cells (APC).

There are a number of such co-stimulatory molecules now identified including adhesion molecules, LFA-3, ICAM-1, ICAM-2. Major co-stimulatory molecules present on APC are the members of the B7 family including B7-1 (CD80), B7-2 (CD86) and B7-3. These molecules are ligands of co-stimulatory receptors on lymphocytes including CD28 (W092/00092), probably the most significant co-stimulatory receptor for resting T-cells. Different members of the B7 family of glycoproteins may deliver subtly different signals to T-cells (Nunes et al. 1996 J. Biol. Chem. 271: 1591-1598).

In one embodiment of the present invention, an ScFv Ab is used which comprises a secreted co-stimulatory molecule ("SCM") with binding affinity for a DAM, such as a tumour antigen.

ScFv Ab Source

The ScFv Ab of the present invention is obtainable from or produced by any suitable source, whether natural or not, or it may be a synthetic ScFv Ab, a semi-synthetic ScFv Ab, a mimetic, a derivatised ScFv Ab, a recombinant ScFv Ab, a fermentation optimised ScFv Ab, a fusion protein or equivalents, mutants and derivatives thereof as long as it retains the required DAM binding specificity of the ScFv Ab of the present invention. These include a ScFv Ab with DAM binding specificity which may have amino acid substitutions or may have sugars or other molecules attached to amino acid functional groups.

The term "mimetic" relates to any chemical which may be a peptide, polypeptide, antibody or other organic chemical which has the same binding specificity as the ScFv Ab of the present invention.

The term "derivative" or "derivatised" as used herein includes chemical modification of an ScFv Ab. Illustrative of such modifications would be replacement of hydrogen by an alkyl, acyl, or amino group. Preferably, the ScFv Ab includes at least a portion of which has been prepared by recombinant DNA techniques or produced by chemical synthesis techniques or combinations thereof.

Preferably, the ScFv Ab is prepared by the use of chemical synthesis techniques.

Chemical Synthesis Methods

The ScFv Ab of the present invention or variants, homologues, derivatives, fragments or mimetics thereof may be produced using chemical methods to synthesize the ScFv Ab amino acid sequence, in whole or in part. For example, peptides can be synthesized by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic peptides may be confirmed by amino acid analysis or sequencing (e.g., the Edman degradation procedure; Creighton, supra).

Direct synthesis of the ScFv Ab or variants, homologues, derivatives, fragments or mimetics thereof can be performed using various solid-phase techniques (Roberge JY et al(1995) Science 269: 202-204) and automated synthesis may be achieved, for example, using the ABI 43 1 A Peptide Synthesizer (Perkin Elmer) in accordance with the instructions provided by the manufacturer. Additionally, the amino acid sequences obtainable from the ScFv Ab, or any part thereof, may be altered during direct synthesis and/or combined using chemical methods with a sequence from other subunits, or any part thereof, to produce a variant ScFv Ab.

In an alternative embodiment of the invention, the coding sequence of the ScFv Ab or variants, homologues, derivatives, fragments or mimetics thereof may be synthesized, in whole or in part, using chemical methods well known in the art (see Caruthers M H et al(1980) Nuc Acids Res Symp Ser 215-23, Horn T et al(1980) Nuc Acids Res Symp Ser 225-232).

Preferably the ScFv Ab of the present invention comprises the amino acid sequence set out in SEQ ID No 1 (see FIG. 1).

Preferably the ScFv Ab of the present invention comprises the amino acid sequence set out in SEQ ID No 3 (see FIG. 2).

Preferably the ScFv Ab of the present invention comprises the amino acid sequence set out in SEQ ID No 4 (see FIG. 6).

Amino Acid Sequences

As used herein, the term "amino acid sequence" refers to peptide, polypeptide sequences, protein sequences or portions thereof.

Preferably, the ScFv Ab is an isolated ScFv Ab and/or purified and/or non-native ScFv Ab.

The ScFv Ab of the present invention may be in a substantially isolated form. It will be understood that the protein may be mixed with carriers or diluents which will not interfere with the intended purpose of the ScFv Ab and still be regarded as substantially isolated. The ScFv Ab of the present invention may also be in a substantially purified form, in which case it will generally comprise the ScFv Ab in a preparation in which more than 90%, e.g. 95%, 98% or 99% of the ScFv Ab in the preparation is a peptide comprising SEQ ID No 1 or SEQ ID No 3 or SEQ ID No 4 or variants, homologues, derivatives or fragments thereof.

Variants/Homologues/Derivatives of Amino Acid Sequences

Preferred amino acid sequences of the present invention are set out in SEQ ID No 1 or SEQ ID No 3 or SEQ ID No 4 are sequences obtainable from the ScFv Ab of the present invention but also include homologous sequences obtained from any source, for example related viral/bacterial proteins, cellular homologues and synthetic peptides, as well as variants or derivatives thereof.

The present invention also provides, for the first time, the full canine 5T4 amino acid and nucleic acid sequences (FIG. 26 and SEQ ID Nos 14 and 15). Thus the present invention also provides i) a canine 5T4 polypeptide having the amino acid sequence shown in SEQ ID No 14 or a variant, homologue, fragment or derivative thereof; and ii) a nucleotide sequence capable of encoding a such canine 5T4 polypeptide. Preferably the nucleotide sequence has the sequence shown as SED ID NO 15 or a variant homologue, fragment or derivative thereof.

Thus, the present invention covers variants, homologues or derivatives of the amino acid sequences presented herein, as well as variants, homologues or derivatives of the nucleotide sequence coding for those amino acid sequences.

In the context of the present invention, a homologous sequence is taken to include an amino acid sequence which is at least 75, 85 or 90% identical, preferably at least 95 or 98% identical at the amino acid level over at least, for example, the amino acid sequence as set out in SEQ ID No 1 or SEQ ID No 3 or SEQ ID No 4 or SEQ ID No 14 of the sequence listing herein. In particular, homology should typically be considered with respect to those regions of the sequence known to be essential for binding specificity (such as amino acids at positions) rather than non-essential neighbouring sequences. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The terms "variant" or "derivative" in relation to the amino acid sequences of the present invention includes any substitution of, variation of, modification of, replacement of, deletion of or addition of one (or more) amino acids from or to the sequence providing the resultant amino acid sequence has a binding specificity, preferably having at least the same binding specificity as the amino acid sequence set out in SEQ ID No 1 or SEQ ID No 3 or SEQ ID No 4 or SEQ ID NO 14 of the sequence listing herein.

SEQ ID No 1 or SEQ ID No 3 or SEQ ID No 4 or SEQ ID No 14 of the sequence listing herein may be modified for use in the present invention. Typically, modifications are made that maintain the binding specificity of the sequence. Amino acid substitutions may be made, for example from 1, 2 or 3 to 10 or 20 substitutions provided that the modified sequence retains the required binding specificity. Amino acid substitutions may include the use of non-naturally occurring analogues.

The ScFv Ab of the present invention may also have deletions, insertions or substitutions of amino acid residues which produce a silent change and result in a functionally equivalent ScFv Ab. Deliberate amino acid substitutions may be made on the basis of similarity in polarity, charge, solubility, hydrophobicity, hydrophilicity, and/or the amphipathic nature of the residues as long as the binding specificity of the ScFv Ab is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. The same also applies to the canine 5T4 sequence.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Preferably, the isolated ScFv Ab and/or purified ScFv Ab and/or non-native ScFv Ab and/or 5T4 sequence is prepared by use of recombinant techniques.

With regard to a fragment of the canine 5T4 sequence, preferably the fragment comprises at least one, preferably some, most preferably all of the amino acids 1-182 and/or 297-420 shown in SEQ ID No 14.

Nucleotide Sequences

It will be understood by a skilled person that numerous different nucleotide sequences can encode the same ScFv Ab of the present invention as a result of the degeneracy of the genetic code. In addition, it is to be understood that skilled persons may, using routine techniques, make nucleotide substitutions that do not affect the ScFv Ab encoded by the nucleotide sequence of the present invention to reflect the codon usage of any particular host organism in which the ScFv Ab of the present invention is to be expressed.

The terms "variant", "homologue" or "derivative" in relation to the nucleotide sequence set out in SEQ ID No 5 (see FIG. 1) or SEQ ID No 7 (see FIG. 2) or SEQ ID No 8 (see FIG. 6) of the present invention includes any substitution of, variation of, modification of, replacement of, deletion of or addition of one (or more) nucleic acid from or to the sequence providing the resultant nucleotide sequence codes for a ScFv Ab having a binding specificity, preferably having at least the same binding specificity as the nucleotide sequence set out in SEQ ID No 5 or SEQ ID No 7 or SEQ ID No 8 of the sequence listings of the present invention.

The terms "variant", "homologue" or "derivative" in relation to the nucleotide sequence set out in SEQ ID No 15 (see FIG. 26) of the present invention includes any substitution of, variation of, modification of, replacement of, deletion of or addition of one (or more) nucleic acid from or to the sequence providing the resultant nucleotide sequence codes for a canine 5T4 polypeptide, preferably a polypeptide as set out in SEQ ID No 14 of the sequence listing of the present invention.

As indicated above, with respect to sequence homology, preferably there is at least 75%, more preferably at least 85%, more preferably at least 90% homology to the sequences shown in the sequence listing herein. More preferably there is at least 95%, more preferably at least 98%, homology. Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

The present invention also encompasses nucleotide sequences that are capable of hybridising selectively to the sequences presented herein, or any variant, fragment or derivative thereof, or to the complement of any of the above. Nucleotide sequences are preferably at least 15 nucleotides in length, more preferably at least 20, 30, 40 or 50 nucleotides in length.

With regard to a fragment of the canine 5T4 sequence, preferably the fragment conprises at least one, preferably some, most preferably all of the nucleic acids 1-546 and/or 890-1263 shown in SEQ ID No 15.

Hybridisation

The term "hybridization" as used herein shall include "the process by which a strand of nucleic acid joins with a complementary strand through base pairing" as well as the process of amplification as carried out in polymerase chain reaction (PCR) technologies.

Nucleotide sequences of the invention capable of selectively hybridising to the nucleotide sequences presented herein, or to their complement, will be generally at least 75%, preferably at least 85 or 90% and more preferably at least 95% or 98% homologous to the corresponding nucleotide sequences presented herein over a region of at least 20, preferably at least 25 or 30, for instance at least 40, 60 or 100 or more contiguous nucleotides. Preferred nucleotide sequences of the invention will comprise regions homologous to the nucleotide sequence set out in SEQ ID No 5 or SEQ ID No 7 or SEQ ID No 8 or Seq ID No 15 of the sequence listings of the present invention preferably at least 80 or 90% and more preferably at least 95% homologous to the nucleotide sequence set out in SEQ ID No 5 or SEQ ID No 7 or SEQ ID No 8 of the sequence listings of the present invention.

The term "selectively hybridizable" means that the nucleotide sequence used as a probe is used under conditions where a target nucleotide sequence of the invention is found to hybridize to the probe at a level significantly above background. The background hybridization may occur because of other nucleotide sequences present, for example, in the cDNA or genomic DNA library being screened. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}P$.

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical nucleotide sequences while an intermediate (or low) stringency hybridization can be used to identify or detect similar or related polynucleotide sequences.

In a preferred aspect, the present invention covers nucleotide sequences that can hybridise to the nucleotide sequence of the present invention under stringent conditions (e.g. 65° C. and 0.1×SSC {1×SSC=0.15 M NaCl, 0.015 M $Na_3$ Citrate pH 7.0). Where the nucleotide sequence of the invention is double-stranded, both strands of the duplex, either individually or in combination, are encompassed by the present invention. Where the nucleotide sequence is single-stranded, it is to be understood that the complementary sequence of that nucleotide sequence is also included within the scope of the present invention.

Nucleotide sequences which are not 100% homologous to the sequences of the present invention but fall within the scope of the invention can be obtained in a number of ways. Other variants of the sequences described herein may be obtained for example by probing DNA libraries made from a range of sources. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the nucleotide sequence set out in SEQ ID No 5 or SEQ ID No 7 or SEQ ID No 8 or SEQ ID No 15 of the sequence listings of the present invention under conditions of medium to high stringency. Similar considerations apply to obtaining species homologues and allelic variants of the amino acid and/or nucleotide sequences of the present invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used. The primers used in degenerate PCR will contain one or more degenerate positions and will be used at stringency conditions lower than those used for cloning sequences with single sequence primers against known sequences.

Alternatively, such nucleotide sequences may be obtained by site directed mutagenesis of characterised sequences, such as the nucleotide sequence set out in SEQ ID No 5 or SEQ ID No 7 or SEQ ID No 8 or SEQ ID NO 15 of the sequence listings of the present invention. This may be useful where for example silent codon changes are required to sequences to optimise codon preferences for a particular host cell in which the nucleotide sequences are being expressed. Other sequence changes may be desired in order to introduce restriction enzyme recognition sites, or to alter the binding specificity of the ScFv Ab encoded by the nucleotide sequences.

The nucleotide sequences of the present invention may be used to produce a primer, e.g. a PCR primer, a primer for an alternative amplification reaction, a probe e.g. labelled with a revealing label by conventional means using radioactive or non-radioactive labels, or the nucleotide sequences may be cloned into vectors. Such primers, probes and other fragments will be at least 15, preferably at least 20, for example at least 25, 30 or 40 nucleotides in length, and are also encompassed by the term nucleotide sequence of the invention as used herein.

The nucleotide sequences such as a DNA polynucleotides and probes according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer nucleotide sequences will generally be produced using recombinant means, for example using a PCR (polymerase chain reaction) cloning techniques. This will involve making a pair of primers (e.g. of about 15 to 30 nucleotides) flanking a region of the targeting sequence which it is desired to clone, bringing the primers into contact with mRNA or cDNA obtained from an animal or human cell, performing a polymerase chain reaction (PCR) under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Due to the inherent degeneracy of the genetic code, other DNA sequences which encode substantially the same or a functionally equivalent amino acid sequence, may be used to clone and express the ScFv Ab. As will be understood by those of skill in the art, it may be advantageous to produce the ScFv Ab—encoding nucleotide sequences possessing non-naturally occurring codons. Codons preferred by a particular prokaryotic or eukaryotic host (Murray E et al(1989) Nuc Acids Res 17:477-508) can be selected, for example, to increase the rate of the ScFv Ab expression or to produce recombinant RNA transcripts having desirable properties, such as a longer half-life, than transcripts produced from naturally occurring sequence.

In one embodiment of the present invention, the ScFv Ab is a recombinant ScFv Ab.

Preferably the recombinant ScFv Ab is prepared using a genetic vector.

Vector

As it is well known in the art, a vector is a tool that allows or faciliates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host and/or a target cell for the purpose of replicating the vectors comprising the nucleotide sequences of the present invention and/or expressing the proteins of the invention encoded by the nucleotide sequences of the present invention. Examples of vectors used in recombinant DNA techniques include but are not limited to plasmids, chromosomes, artificial chromosomes or viruses.

The term "vector" includes expression vectors and/or transformation vectors.

The term "expression vector" means a construct capable of in vivo or in vitro/ex vivo expression.

The term "transformation vector" means a construct capable of being transferred from one species to another.

"Naked DNA"

The vectors comprising nucleotide sequences encoding ScFv Abs of the present invention for use in affecting viral infections may be administered directly as "a naked nucleic acid construct", preferably further comprising flanking sequences homologous to the host cell genome.

As used herein, the term "naked DNA" refers to a plasmid comprising a nucleotide sequences encoding a ScFv Ab of the present invention together with a short promoter region to control its production. It is called "naked" DNA because the plasmids are not carried in any delivery vehicle. When such a DNA plasmid enters a host cell, such as a eukaryotic cell, the proteins it encodes (such as the ScFv Ab) are transcribed and translated within the cell.

Non-Viral Delivery

Alternatively, the vectors comprising nucleotide sequences of the present invention may be introduced into suitable host cells using a variety of non-viral techniques known in the art, such as transfection, transformation, electroporation and biolistic transformation.

As used herein, the term "transfection" refers to a process using a non-viral vector to deliver a gene to a target mammalian cell.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), multivalent cations such as spermine, cationic lipids or polylysine, 1,2,-bis (oleoyloxy)-3-(trimethylammonio) propane (DOTAP)-cholesterol complexes (Wolff and Trubetskoy 1998 Nature Biotechnology 16: 421) and combinations thereof.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example lipofectam™ and transfectam™). Typically, nucleic acid constructs are mixed with the transfection agent to produce a composition.

Viral Vectors

Alternatively, the vectors comprising nucleotide sequences of the present invention may be introduced into suitable host cells using a variety of viral techniques which are known in the art, such as for example infection with recombinant viral vectors such as retroviruses, herpes simplex viruses and adenoviruses.

Preferably the vector is a recombinant viral vectors. Suitable recombinant viral vectors include but are not limited to adenovirus vectors, adeno-associated viral (AAV) vectors, herpes-virus vectors, a retroviral vector, lentiviral vectors, baculoviral vectors, pox viral vectors or parvovirus vectors (see Kestler et al 1999 Human Gene Ther 10(10):1619-32). In the case of viral vectors, gene delivery is mediated by viral infection of a target cell.

Retroviral Vectors

Examples of retroviruses include but are not limited to: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV).

Preferred vectors for use in accordance with the present invention are recombinant viral vectors, in particular recombinant retroviral vectors (RRV) such as lentiviral vectors.

The term "recombinant retroviral vector" (RRV) refers to a vector with sufficient retroviral genetic information to allow packaging of an RNA genome, in the presence of packaging components, into a viral particle capable of infecting a target cell. Infection of the target cell includes reverse transcription and integration into the target cell genome. The RRV carries non-viral coding sequences which are to be delivered by the vector to the target cell. An RRV is incapable of independent replication to produce infectious retroviral particles within the final target cell. Usually the RRV lacks a functional gag-pol and/or env gene and/or other genes essential for replication. The vector of the present invention may be configured as a split-intron vector. A split intron vector is described in PCT patent application WO 99/15683.

A detailed list of retroviruses may be found in Coffin et al("Retroviruses" 1997 Cold Spring Harbour Laboratory Press Eds: J M Coffin, S M Hughes, H E Varmus pp 758-763).

Lentiviral Vectors

Lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells (Lewis et al 1992 EMBO. J 11: 3053-3058; Lewis and Emerman 1994 J. Virol. 68: 510-516). In contrast, other retroviruses—such as MLV—are unable to infect non-dividing cells such as those that make up, for example, muscle, brain, lung and liver tissue.

Adenoviruses

In one embodiment of the present invention, the features of adenoviruses may be combined with the genetic stability of retroviruses/lentiviruses which can be used to transduce target cells to become transient retroviral producer cells capable of stably infect neighbouring cells. Such retroviral producer cells which are engineered to express a ScFv Ab of the present invention can be implanted in organisms such as animals or humans for use in the treatment of disease such as cancer.

Pox Viruses

Preferred vectors for use in accordance with the present invention are recombinant pox viral vectors such as fowl pox virus (FPV), entomopox virus, vaccinia virus such as NYVAC, canarypox virus, MVA or other non-replicating viral vector systems such as those described for example in WO 95/30018.

Hybrid Viral Vectors

In a further broad aspect, the present invention provides a hybrid viral vector system for in vivo delivery of a nucleotide sequence encoding a ScFc Ab of the present invention, which system comprises one or more primary viral vectors which encode a secondary viral vector, the primary vector or vectors capable of infecting a first target cell and of expressing therein the secondary viral vector, which secondary vector is capable of transducing a secondary target cell.

Preferably the primary vector is obtainable from or is based on an adenoviral vector and/or the secondary viral vector is obtainable from or is based on a retroviral vector preferably a lentiviral vector.

Targeted Vector

The term "targeted vector" refers to a vector whose ability to infect/transfect/transduce a cell or to be expressed in a host and/or target cell is restricted to certain cell types within the host organism, usually cells having a common or similar phenotype.

Replication Vectors

The nucleotide sequences encoding the ScFv Ab of the present invention may be incorporated into a recombinant replicable vector. The vector may be used to replicate the nucleotide sequence in a compatible host cell. Thus in one embodiment of the present invention, the invention provides a method of making the ScFv Ab of the present invention by introducing a nucleotide sequence of the present invention into a replicable vector, introducing the vector into a compatible host cell, and growing the host cell under conditions which bring about replication of the vector. The vector may be recovered from the host cell.

Expression Vector

Preferably, a nucleotide sequence of present invention which is inserted into a vector is operably linked to a control sequence that is capable of providing for the expression of the coding sequence, such as the coding sequence of the ScFv Ab of the present invention by the host cell, i.e. the vector is an expression vector. The ScFv Ab produced by a host recombinant cell may be secreted or may be contained intracellularly depending on the sequence and/or the vector used. As will be understood by those of skill in the art, expression vectors containing the ScFv Ab coding sequences can be designed with signal sequences which direct secretion of the ScFv Ab coding sequences through a particular prokaryotic or eukaryotic cell membrane.

Expression in Vitro

The vectors of the present invention may be transformed or transfected into a suitable host cell and/or a target cell as described below to provide for expression of an ScFv Ab of the present invention. This process may comprise culturing a host cell and/or target cell transformed with an expression vector under conditions to provide for expression by the vector of a coding sequence encoding the ScFv Ab and optionally recovering the expressed ScFv Ab. The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. The expression of the ScFv Abs of the invention may be constitutive such that they are continually produced, or inducible, requiring a stimulus to initiate expression. In the case of inducible expression, ScFv Ab production can be initiated when required by, for example, addition of an inducer substance to the culture medium, for example dexamethasone or IPTG.

ScFv Ab Constructs

Fusion Proteins

The ScFv Ab of the invention may also be produced as fusion proteins, for example to aid in extraction and purification. Examples of fusion protein partners include glutathione-S-transferase (GST), 6xHis, GALA (DNA binding and/or transcriptional activation domains) and β-galactosidase. Other examples of fusion protein partners include but are not limited to a fused recombinant ScFv Ab protein comprising an antigenic co-protein such as GST, β-galactosidase or the lipoprotein D from *Haemophilus influenzae* which are relatively large co-proteins, which solubilise and facilitate production and purification thereof. Alternatively, the fused protein may comprise a carrier protein such as bovine serum albumin (BSA) or keyhole limpet haemocyanin (KLH). In certain embodiments of the present invention, the marker sequence is a hexa-histidine peptide, as provided in the pQE vector (Qiagen Inc) and described in Gentz et al(1989 PNAS 86: 821-824). Such fusion proteins are readily expressable in yeast culture (as described in Mitchell et al 1993 Yeast 5: 715-723) and are easily purified by affinity chromatography.

Other recombinant constructions may join the ScFv Ab coding sequence to nucleotide sequence encoding a polypeptide domain which will facilitate purification of soluble proteins (Kroll D J et al(1993) DNA Cell Biol 12:441-53). Such purification facilitating domains include, but are not limited to, metal chelating peptides such as histidine-tryptophan modules that allow purification on immobilized metals (Porath J (1992) Protein Expr Purif 3-0.26328 1), protein A domains that allow purification on immobilized immunoglobulin, and the domain utilized in the FLAGS extension/affinity purification system (Immunex Corp, Seattle, Wash.).

It may also be convenient to include a proteolytic cleavage site between the fusion protein partner and the protein sequence of interest to allow removal of fusion protein sequences. By way of example, a fusion protein may also be engineered to contain a cleavage site located between the nucleotide sequence encoding the ScFv Ab and the heterologous protein sequence, so that the ScFv Ab may be cleaved and purified away from the heterologous moiety. The inclusion of a cleavable linker sequence such as Factor XA or enterokinase (Invitrogen, San Diego, Calif.) between the purification domain and the ScFv Ab may also be useful to facilitate purification. Preferably the fusion protein will not hinder the binding specificity of the ScFv Ab comprising the amino acid sequence of the present invention.

In one preferred embodiment, the fusion protein comprises or encodes a secreted co-co-stimulatory molecule (SCM).

SCM Fusion Proteins

The secreted co-stimulatory molecule (SCM) of the invention may be an engineered fusion protein comprising a signal peptide for secretion from mammalian cells and at least one further domain which acts as a co-stimulatory signal to a cell of the immune system. The use of combinations of SCMs containing different co-stimulatory domains may also envisaged. The ScFv Abs comprising the SCMs may be produced by expression of SCM-encoding genes in the autologous cells of the individual to be treated and hence any post-translational modifications added to the protein by the host cell are authentic and provide fully functional protein and appropriate pharmacokinetics.

WO-A-92/00092 describes truncated forms of B7-1, derived by placing a translation stop codon before the transmembrane domain, secreted from mammalian cells. In that particular case, a heterologous signal peptide from the Oncostatin M gene was used. WO-A92/00092 also describes fusion proteins which contain the extracellular domain of B7-1 fused to the Fc region of an immunoglobulin. Such molecules can bind to CD28 on T-cells and serve to stimulate T-cell proliferation. However such stimulation occurs only to a moderate extent unless the B7 or B7-derivative is immobilised on a solid surface.

Gerstmayer et al. (1997 J. Immol. 158: 4584-4590) describes a fusion of B7-2 to an ScFv specific for ErbB2 followed by a myc epitope tag and polyhistidine tag which is secreted when expressed in the yeast *Pichia pastoris*. This molecule retained binding for antigen and co-stimulated proliferation of T-cells prestimulated with PMA and IL-2. However, glycosylation of such a molecule is of the yeast type, which is likely to lead to inappropriate pharmacokinetics in humans.

In accordance with the present invention, any suitable co-stimulatory domain(s) may be used. By way of example, co-stimulatory domains can be chosen from extracellular portions of the B7 family of cell-surface glycoproteins, including B7-1, B7-2 and B7-3 or other co-stimulatory cell surface glycoproteins such as but not limited to co-stimulatory receptor-ligand molecules including CD2/LFA-3, LFA-1/ICAM-1 and ICAM-3. Studies have demonstrated that T cell co-stimulation by monocytes is dependent on each of two receptor ligand pathways CD2/LFA-3 and LFA-1/ICAM-1 (Van Seventer et al 1991 Eur J Immunol 21: 1711-1718). In addition, it has been shown that ICAM-3, the third LFA-1 counterreceptor, is a co-stimulatory molecule for resting and activated T lymphocytes (Hernandez-Caselles et al 1993 Eur J Immunol 23: 2799-2806).

Other possible co-stimulatory molecules may include a novel glycoprotein receptor designated SLAM, has been identified which, when engaged, potentiates T-cell expansion in a CD28-independent manner and induces a Th0/Th1 cytokine production profile (Cocks et al 1995 Nature 376: 260-263).

CD6, a cell surface glycoprotein, has also been shown to function as a co-stimulatory and adhesion receptor on T cells.

Four CD6 isoforms (CD6a, b, c, d) have been described (Kobarg et al 1997 Eur J Immunol 27:.2971-2980). A role for the very late antigen (VLA-4) integrin in the activation of human memory B cells has also been suggested (Silvy et al 1997 Eur J Immunol 27: 2757-2764). Endothelial cells also provide unique co-stimulatory signals that affect the phenotype of activated CD4+ T cells (Karmann et al 1996 Eur J Immunol 26: 610-617). A B3 protein, present on the surface of lipopolysaccharide-activated B cells, which can provide co-stimulation to resting T cells leading to a predominant release of interleukin-4 (IL-4) and IL-5 and negligible amounts of IL-2 and interferon gamma has been described (Vinay et al 1995 J Biol Chem 270: 23429-23436). The coexpression of a novel co-stimulatory T cell antigen (A6H) on T cells and tumour cells has suggested a possible function related to common properties of these cells (Labuda et al 1995 Int Immunol 7: 1425-1432).

In one preferred embodiment of the invention, the co-stimulatory domain is a portion of B7-1 or B7-2, more preferably the complete extracellular portion of B7-1 or B7-2.

In one preferred embodiment the ScFv Ab of the present invention is formed by expression of a novel gene encoding a fusion protein containing the DAM binding domain or domains and the co-stimulatory domain or domains. In the context of the present invention, the co-stimulatory domain is fused to the ScFv. The domains can be placed in the order (N-terminus to C-terminus): antigen-binding domain followed by co-stimulatory domain; or co-stimulatory domain followed by antigen-binding domain. Preferably, the co-stimulatory domain is placed at the N-terminus followed by the antigen-binding domain. A signal peptide is included at the N-terminus, and may be for example the natural signal peptide of the co-stimulatory extracellular domain. The different domains may be separated by additional sequences, which may result from the inclusion of convenient restriction-enzyme cleavage sites in the novel gene to facilitate its construction, or serve as a peptide spacer between the domains, or serve as a flexible peptide linker or provide another function. Preferably the domains are separated by a flexible linker.

Two or more different genes encoding different SCMs may be used to achieve improved co-stimulation, or both co-stimulation of naive T-cells and induction of memory responses. For example a gene encoding an SCM containing the B7-1 extracellular domain may be administered with a gene encoding an SCM containing the B7-2 extracellular domain.

Quantitation of SCFV Antibody Production

Although the presence/absence of marker gene expression may suggest that the nucleotide sequence and/or its ScFv Ab is also present, its presence and expression may be confirmed by routine means. For example, if the ScFv Ab encoding nucleotide sequence is inserted within a marker gene sequence, recombinant cells containing the ScFv Ab coding regions may be identified by the absence of the marker gene function. Alternatively, a marker gene may be placed in tandem with a ScFv Ab encoding nucleotide sequence under the control of a single promoter. Expression of the marker gene in response to induction or selection usually indicates expression of the ScFv Ab as well.

Additional methods to quantitate the expression of a particular molecule include radiolabeling (Melby PC et al 1993 J Immunol Methods 159:235-44) or biotinylating (Duplaa C et al 1993 Anal Biochem 229-36) nucleotides, coamplification of a control nucleic acid, and standard curves onto which the experimental results are interpolated. Quantitation of multiple samples may be speeded up by running the assay in an ELISA format where the ScFv Ab of interest is presented in various dilutions and a spectrophotometric or calorimetric response gives rapid quantitation.

Host/Target Cells

Host and/or target cells comprising nucleotide sequences of the present invention may be used to express the ScFv Abs of the present invention under in vitro, in vivo and ex vivo conditions.

The term "host cell and/or target cell" includes any cell derivable from a suitable organism which a vector is capable of transfecting or transducing. Examples of host and/or target cells can include but are not limited to cells capable of expressing the ScFv Ab of the present invention under in vitro, in vivo and ex vivo conditions. Examples of such cells include but are not limited to macrophages, endothelial cells or combinations thereof. Further examples include respiratory airway epithelial cells, hepatocytes, muscle cells, cardiac myocytes, synoviocytes, primary mammary epithelial cess and post-mitotically terminally differentiated non-replicating cells such as macrophages and/or neurons.

In a preferred embodiment, the cell is a mammalian cell.

In a highly preferred embodiment, the cell is a human cell.

The term "organism" includes any suitable organism. In a preferred embodiment, the organism is a mammal. In a highly preferred embodiment, the organism is a human.

Although the ScFv Ab of the invention may be produced using prokaryotic cells as host cells, it is preferred to use eukaryotic cells, for example yeast, insect or mammalian cells, in particular mammalian cells. Suitable host cells include bacteria such as E. Coli, yeast, mammalian cell lines and other eukaryotic cell lines, for example insect Sf9 cells.

The present invention also provides a method comprising transforming a host and/or target cell with a or the nucleotide sequence(s) of the present invention.

The term "transformed cell" means a host cell and/or a target cell having a modified genetic structure. With the present invention, a cell has a modified genetic structure when a vector according to the present invention has been introduced into the cell.

Host cells and/or a target cells may be cultured under suitable conditions which allow expression of the ScFv Ab of the invention.

The present invention also provides a method comprising culturing a transformed host cell—which cell has been transformed with a or the nucleotide sequence(s) according to the present invention under conditions suitable for the expression of the ScFv Ab encoded by said nucleotide sequence(s).

The present invention also provides a method comprising culturing a transformed host cell—which cell has been transformed with a or the nucleotide sequence(s) according to the present invention or a derivative, homologue, variant or fragment thereof—under conditions suitable for the expression of the ScFv Ab encoded by said nucleotide sequence(s); and then recovering said ScFv Ab from the transformed host cell culture.

The ScFv Ab of the present invention can be extracted from host cells by a variety of techniques known in the art, including enzymatic, chemical and/or osmotic lysis and physical disruption. The ScFv Ab may be purified and isolated in a manner known per se.

Regulation of Expression In Vitro/Vivo/Ex Vivo

The present invention also encompasses gene therapy whereby the ScFv Ab encoding nucleotide sequence(s) of the present invention is regulated in vitro/in vivo/ex vivo. For example, expression regulation may be accomplished by administering compounds that bind to the ScFv Ab encoding nucleotide sequence(s) of the present invention, or control regions associated with the ScFv Ab encoding nucleotide sequence of the present invention, or its corresponding RNA transcript to modify the rate of transcription or translation.

Control Sequences

Control sequences operably linked to sequences encoding the ScFv Ab of the present invention include promoters/enhancers and other expression regulation signals. These control sequences may be selected to be compatible with the host cell and/or target cell in which the expression vector is designed to be used. The control sequences may be modified, for example by the addition of further transcriptional regulatory elements to make the level of transcription directed by the control sequences more responsive to transcriptional modulators.

Operably Linked

The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Preferably the nucleotide sequence of the present invention is operably linked to a transcription unit.

The term "transcription unit(s)" as described herein are regions of nucleic acid containing coding sequences and the signals for achieving expression of those coding sequences independently of any other coding sequences. Thus, each transcription unit generally comprises at least a promoter, an optional enhancer and a polyadenylation signal.

Promoters

The term promoter is well-known in the art and is used in the normal sense of the art, e.g. as an RNA polymerase binding site. The term encompasses nucleic acid regions ranging in size and complexity from minimal promoters to promoters including upstream elements and enhancers.

The promoter is typically selected from promoters which are functional in mammalian, cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of α-actin, β-actin, tubulin) or, alternatively, a tissue-specific manner (such as promoters of the genes for pyruvate kinase).

Hypoxic Promoters/Enhancers

The enhancer and/or promoter may be preferentially active in a hypoxic or ischaemic or low glucose environment, such that the ScFv Ab encoding nucleotide sequence(s) is preferentially expressed in the particular tissues of interest, such as in the environment of a tumour, arthritic joint or other sites of ischaemia. Thus, any significant biological effect or deleterious effect of the ScFv Ab encoding nucleotide sequence(s) on the individual being treated may be reduced or eliminated. The enhancer element or other elements conferring regulated expression may be present in multiple copies. Likewise, or in addition, the enhancer and/or promoter may be preferentially active in one or more specific cell types—such as any one or more of macrophages, endothelial cells or combinations thereof. Further examples may include but are not limited to respiratory airway epithelial cells, hepatocytes, muscle cells, cardiac myocytes, synoviocytes, primary mammary epithelial cells and post-mitotically terminally differentiated non-replicating cells such as macrophages and/or neurons.

Tissue-Specific Promoters

The promoters of the present invention may be tissue-specific promoters. Examples of suitable tissue restricted promoters/enhancers are those which are highly active in tumour cells such as a promoter/enhancer from a MUC1 gene, a CEA gene or a 5T4 antigen gene. Examples of temporally restricted promoters/enhancers are those which are responsive to ischaemia and/or hypoxia, such as hypoxia response elements or the promoter/enhancer of a grp78 or a grp94 gene. The alpha fetoprotein (AFP) promoter is also a tumour-specific promoter. One preferred promoter-enhancer combination is a human cytomegalovirus (hCMV) major immediate early (MIE) promoter/enhancer combination.

Preferably the promoters of the present invention are tissue specific. That is, they are capable of driving transcription of a ScFv Ab encoding nucleotide sequence(s) in one tissue while remaining largely "silent" in other tissue types.

The term "tissue specific" means a promoter which is not restricted in activity to a single tissue type but which nevertheless shows selectivity in that they may be active in one group of tissues and less active or silent in another group. A desirable characteristic of the promoters of the present invention is that they posess a relatively low activity in the absence of activated hypoxia-regulated enhancer elements, even in the target tissue. One means of achieving this is to use "silencer" elements which suppress the activity of a selected promoter in the absence of hypoxia.

The term "hypoxia" means a condition under which a particular organ or tissue receives an inadequate supply of oxygen.

The level of expression of a or the ScFv Ab encoding nucleotide sequence(s) under the control of a particular promoter may be modulated by manipulating the promoter region. For example, different domains within a promoter region may possess different gene regulatory activities. The roles of these different regions are typically assessed using vector constructs having different variants of the promoter with specific regions deleted (that is, deletion analysis). This approach may be used to identify, for example, the smallest region capable of conferring tissue specificity or the smallest region conferring hypoxia sensitivity.

A number of tissue specific promoters, described above, may be particularly advantageous in practising the present invention. In most instances, these promoters may be isolated as convenient restriction digestion fragments suitable for cloning in a selected vector. Alternatively, promoter fragments may be isolated using the polymerase chain reaction. Cloning of the amplified fragments may be facilitated by incorporating restriction sites at the 5' end of the primers.

Inducible Promoters

The promoters of the present invention may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell.

Inducible means that the levels of expression obtained using the promoter can be regulated.

Enhancer

In addition, any of these promoters may be modified by the addition of further regulatory sequences, for example enhancer sequences. Chimeric promoters may also be used comprising sequence elements from two or more different promoters described above.

The term "enhancer" includes a DNA sequence which binds to other protein components of the transcription initiation complex and thus facilitates the initiation of transcription directed by its associated promoter.

The in vitro/in vivo/ex vivo expression of the ScFv Ab of the present invention may be used in combination with a protein of interest (POI) or a nucleotide sequence of interest (NOI) encoding same.

Combination With POIs/NOIs

The ScFv Ab of the present invention or nucleotide sequence encoding same may be used in combination with a POI, such as a pro-drug activating enzyme either directly or by vector delivery to, for example, a target cell or target tissue. Instead of or as well as being selectively expressed in target tissues, the ScFv Ab of the present invention or nucleotide sequence encoding same may be used in combination with another POI such as a pro-drug activation enzyme or enzymes or with a nucleotide sequences of interest (NOI) or NOIs which encode a pro-drug activation enzyme or enzymes. These pro-drug activation enzyme or enzymes may have no significant effect or no deleterious effect until the individual is treated with one or more pro-drugs upon which the appropriate pro-drug enzyme or enzymes act. In the presence of the active POI or NOI encoding same, treatment of an individual with the appropriate pro-drug may lead to enhanced reduction in the disease condition such as a reduction in tumour growth or survival.

PRO-Drug POIs

A POI, such as a pro-drug activating enzyme, may be delivered to a disease site, such as a tumour site for the treatment of a cancer. In each case, a suitable pro-drug is used in the treatment of the patient in combination with the appropriate pro-drug activating enzyme. An appropriate pro-drug may be administered in conjunction with the ScFv Ab or vector comprising the nucleotide sequence encoding same. Examples of pro-drugs include: etoposide phosphate (with alkaline phosphatase, Senter et al 1988 Proc Natl Acad Sci 85: 4842-4846); 5-fluorocytosine (with cytosine deaminase, Mullen et al 1994 Cancer Res 54: 1503-1506); Doxorubicin-N-p-hydroxyphenoxyacetamide (with Penicillin-V-Amidase, Kerr et al 1990 Cancer Immunol Immunother 31: 202-206); Para-N-bis(2-chloroethyl)aminobenzoyl glutamate (with carboxypeptidase G2); Cephalosporin nitrogen mustard carbamates (with βb-lactamase); SR4233 (with P450 Reductase); Ganciclovir (with HSV thymidine kinase, Borrelli et al 1988 Proc Natl Acad Sci 85: 7572-7576); mustard pro-drugs with nitroreductase (Friedlos et al 1997 J Med Chem 40: 1270-1275) and Cyclophosphamide (with P450 Chen et al 1996 Cancer Res 56: 1331-1340).

Examples of suitable pro-drug activation enzymes for use in the invention include a thymidine phosphorylase which activates the 5-fluoro-uracil pro-drugs capcetabine and furtulon; thymidine kinase from Herpes Simplex Virus which activates ganciclovir; a cytochrome P450 which activates a prodrug such as cyclophosphamide to a DNA damaging agent; and cytosine deaminase which activates 5-fluorocytosine. Preferably, a pro-drug activating enzyme of human origin is used.

POIs and NOIs

Other suitable proteins of interest (POIs) or NOIs encoding same for use in the present invention include those that are of therapeutic and/or diagnostic application such as, but are not limited to: sequences encoding cytokines, chemokines, hormones, antibodies, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumour suppressor protein and growth factors, membrane proteins, vasoactive proteins and peptides, anti-viral proteins and ribozymes, and derivatives therof (such as with an associated reporter group). When included, the POIs or NOIs encoding same may be typically operatively linked to a suitable promoter, which may be a promoter driving expression of a ribozyme(s), or a different promoter or promoters, such as in one or more specific cell types.

Bystander Effect

The POI and/or NOI encoding same may be proteins which are secreted from a cell. Alternatively the POI expression products are not secreted and are active within the cell. In either event, it is preferred for the POI expression product to demonstrate a bystander effector or a distant bystander effect; that is the production of the expression product in one cell leading to the killing of additional, related cells, either neighbouring or distant (e.g. metastatic), which possess a common phenotype.

Suitable POIs or NOIs encoding same for use in the present invention in the treatment or prophylaxis of cancer include proteins which: destroy the target cell (for example a ribosomal toxin), act as: tumour suppressors (such as wild-type p53); activators of anti-tumour immune mechanisms (such as cytokines, co-stimulatory molecules and immunoglobulins); inhibitors of angiogenesis; or which provide enhanced drug sensitivity (such as pro-drug activation enzymes); indirectly stimulate destruction of target cell by natural effector cells (for example, strong antigen to stimulate the immune system or convert a precursor substance to a toxic substance which destroys the target cell (for example a prodrug activating enzyme). Encoded proteins could also destroy bystander tumour cells (for example with secreted antitumour antibody-ribosomal toxin fusion protein), indirectly stimulate destruction of bystander tumour cells (for example cytokines to stimulate the immune system or procoagulant proteins causing local vascular occlusion) or convert a precursor substance to a toxic substance which destroys bystander tumour cells (eg an enzyme which activates a prodrug to a diffusible drug).

Also, the delivery of NOI(s) encoding antisense transcripts or ribozymes which interfere with expression of cellular genes for tumour persistence (for example against aberrant myc transcripts in Burkitts lymphoma or against bcr-abl transcripts in chronic myeloid leukemia. The use of combinations of such POIs and/or NOIs encoding same is also envisaged.

Examples of hypoxia regulatable therapeutic NOIs can be found in PCT/GB95/00322 (WO-A-952 1927).

ScFv Ab Coupling

The ScFv Ab of the present invention can be coupled to other molecules using standard methods. The amino and carboxyl termini of ScFv Ab may be isotopically and nonisotopically labeled with many techniques, for example radiolabeling using conventional techniques (tyrosine residues-chloramine T, iodogen, lactoperoxidase; lysine residues-Bolton-Hunter reagent). These coupling techniques are well known to those skilled in the art. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

Chemical Coupling

The ScFv Ab of the present invention may be chemically coupled to isotopes, enzymes, carrier proteins, cytotoxic agents, fluorescent molecules, radioactive nucleotides and other compounds for a variety of applications including but not limited to imaging/prognosis, diagnosis and/or therapy. The efficiency of the coupling reaction is determined using different techniques appropriate for the specific reaction. For example, radiolabeling of an ScFv Ab peptide with $^{125}$I is accomplished using chloramine T and Na$^{125}$I of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, the unreacted Na$^{125}$I is separated from the labeled ScFv Ab. The peptide fractions with the highest specific radioactivity are stored for subsequent use such as analysis of the ability to bind to a ScFv Ab.

Imaging

The use of labelled ScFv Abs of the present invention with short lived isotopes enables visualization quantitation of DAM binding sites in vivo using autoradiographic, or modern radiographic or other membrane binding techniques such as positron emission tomography in order to locate tumours with ScFv Ab binding. sites. This application provides important diagnostic and/or prognostic research tools.

Conjugates

In other embodiments, the ScFv Ab of the invention is coupled to a scintigraphic radiolabel, a cytotoxic compound or radioisotope, an enzyme for converting a non-toxic prodrug into a cytotoxic drug, a compound for activating the immune system in order to target the resulting conjugate to a disease site such as a colon tumour, or a cell-stimulating compound. Such conjugates have a "binding portion", which consists of the ScFv Ab of the invention, and a "functional portion", which consists of the radiolabel, toxin or enzyme. Different ScFv Abs can be synthesized for use in several applications including but not limited to the linkage of a ScFv Ab to cytotoxic agents for targeted killing of cells that bind the ScFv Ab.

The ScFv Ab may alternatively be used alone in order simply to block the activity of the DAM, particularly by physically interfering with its binding of another compound.

The binding portion and the functional portion of the conjugate (if also a peptide or poypeptide) may be linked together by any of the conventional ways of cross linking polypeptides, such as those generally described in O'Sullivan et al(Anal. Biochem 1979: 100, 100-108). For example, one portion may be enriched with thiol groups and the other portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Alternatively, if the binding portion contains carbohydrates, such as would be the case for an antibody or some antibody fragments, the functional portion may be linked via the carbohydrate portion using the linking technology in EP 0 088 695.

The functional portion of the conjugate may be an enzyme for converting a non-toxic prodrug into a toxic drug, for example the conjugates of Bagshawe and his colleagues (Bagshawe (1987) Br. J. Cancer 56, 531; Bagshawe et al(Br. J. Cancer 1988: 58, 700); WO 88/07378) or cyanide-releasing systems (WO 91/11201).

It may not be necessary for the whole enzyme to be present in the conjugate but, of course, the catalytic portion must be present. So-called "abzymes" may be used, where a ScFv Ab is raised to a compound involved in the reaction one wishes to catalyse, usually the reactive intermediate state. The resulting antibody can then function as an enzyme for the reaction.

The conjugate may be purified by size exclusion or affinity chromatography, and tested for dual biological activities. The antigen immunoreactivity may be measured using an enzyme-linked immunosorbent assay (ELISA) with immobilised antigen and in a live cell radio-immunoassay. An enzyme assay may be used for β-glucosidase using a substrate which changes in absorbance when the glucose residues are hydrolysed, such as oNPG (o-nitrophenyl-β-D-glucopyranoside), liberating 2-nitrophenol which is measured spectrophotometrically at 405 nm.

The stability of the conjugate may be tested in vitro initially by incubating at 37° C. in serum, followed by size exclusion FPLC analysis. Stability in vivo can be tested in the same way in mice by analysing the serum at various times after injection of the conjugate. In addition, it is possible to radiolabel the ScFv Ab with $^{125}$I, and the enzyme with $^{131}$I before conjugation, and to determine the biodistribution of the conjugate, free ScFv Ab and free enzyme in mice.

Alternatively, the conjugate may be produced as a fusion compound by recombinant DNA techniques whereby a length of DNA comprises respective regions encoding the two portions of the conjugate either adjacent to one another or separated by a region encoding a linker peptide which does not destroy the desired properties of the conjugate.

Conceivably, two of the functional portions of the compound may overlap wholly or partly. The DNA is then expressed in a suitable host in known ways.

Diagnostic Kits

The present invention also includes diagnostic methods and kits for detection and measurement of DAM in biological fluids and tissues, and for localization of a DAM in tissues. The ScFv Ab of the present invention that possess high binding specificity can be used to establish easy to use kits for rapid, reliable, sensitive, and specific measurement and localization of a DAM in extracts of plasma, urine, tissues, and in cell culture media. The ScFv Ab of the present invention may also be used in a diagnostic method and kit to permit detection of circulating DAMs which, in certain situations, may indicate the progression of a disease state such as the spread of micrometastases by primary tumours in situ.

These kits may include but are not limited to the following techniques; competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established. Intraassay and interassay variation is established at 20%, 50% and 80% points on the standard curves of displacement or activity.

One example of an assay kit commonly used in research and in the clinic is a radioimmunoassay (RIA) kit. After successful radioiodination and purification of a ScFv Ab, the antiserum possessing the highest titer is added at several dilutions to tubes containing a relatively constant amount of radioactivity, such as 10,000 cpm, in a suitable buffer system. Other tubes contain buffer or preimmune serum to determine the non-specific binding. After incubation at 4° C. for 24 hours, protein A is added and the tubes are vortexed, incubated at room temperature for 90 minutes, and centrifuged at approximately 2000-2500 times g at 4° C. to precipitate the complexes of antiserum bound to the labeled ScFv Ab. The supernatant is removed by aspiration and the radioactivity in the pellets counted in a gamma counter. The antiserum dilution that binds approximately 10 to 40% of the labeled ScFv Ab after subtraction of the non-specific binding is further characterized.

Immunohistochemistry

An immunohistochemistry kit may also be used for localization of DAM in tissues and cells. This immunohistochemistry kit provides instructions, a ScFv Ab, and possibly blocking serum and secondary antiserum linked to a fluorescent molecule such as fluorescein isothiocyanate, or to some other reagent used to visualize the primary antiserum. Immunohistochemistry techniques are well known to those skilled in the art. This immunohistochemistry kit permits localization of a DAM in tissue sections and cultured cells using both light and electron microscopy. It is used for both research and clinical purposes. For example, tumours are biopsied or collected and tissue sections cut with a microtome to examine sites of DAM production. Such information is useful for diagnostic and possibly therapeutic purposes in the detection and treatment of diseases such as cancer.

Foetal Cell Analysis

The ScFv antibody and/or the canine 5T4 sequence of the present invention are also useful in methods for isolating foetal cells from maternal blood. Isolation of foetal cells from maternal blood has been proposed as a non-invasive alternative to aminocentesis (see WO 97/30354).

In this embodiment of the invention the DAM may be any molecule which is expressed at different levels on maternal and foetal cells. Preferably the DAM is expressed exclusively on foetal cells. 5T4 is known to be expressed at very high levels on trophoblasts. Thus an antibody against 5T4 may be used to isolate trophoblasts from maternal blood. The antibody may, for example be an ScFv according to the present invention, or an antibody which is specific for (for example, raised against) a 5T4 polypeptide of a different species.

Thus the present invention also provides a method for isolating a foetal cell from maternal blood using an ScFv antibody of the present invention, or an anti-5T4 antibody from a different species. The canine 5T4 polypeptide of the present invention is useful for generating such cross-reactive antibodies.

The foetal cell may, for example, be a trophoblast or an erythrocyte.

The maternal/foetal cells may be from a human or an animal. Hence, the method of the present invention may be used for medical or veterinary applications. In a preferred embodiment, the mother and foetus are non-human, such that the isolation method is part of a veterinary application.

The isolation process may form part of a diagnostic method. For example, the foetal cells may then be subject to biochemical or genetic sampling. Such a procedure sould be used to test for foetal abnormalities such as Downs syndrome, or to determine the sex of the foetus.

Combination Therapy

The ScFv Abs of the present invention may be used in combination with other compositions and procedures for the treatment of diseases. By way of example, the ScFv Abs may also be used in combination with conventional treatments of diseases such as cancer. By ways of further example, a tumor may be treated conventionally with surgery, radiation or chemotherapy combined with a ScFv Ab or a ScFv Ab may be subsequently administered to the patient to extend the dormancy of micrometastases and to stabilize any residual primary tumor.

ScFv Ab Delivery

The ScFv Ab can be delivered with a therapeutically effective agent at the same moment in time and at the same site. Alternatively, the ScFv Ab and the therapeutically effective agent may be delivered at a different time and to a different site. The ScFv Ab and the therapeutically effective agent may even be delivered in the same delivery vehicle for the prevention and/or treatment of a disease condition such as cancer.

Therapeutic strategies based on the use of the ScFv Ab include the recruitment and activation of T cells by using a fusion of an DAM reactive ScFv Ab fragment with the bacterial superantigen staphylococcal enterotoxin (Dohlsten et al1994) or by using bispecific antibodies, directed to both DAM and the T-cell CD3 antigen (Kroesen et al1994). Anti-DAM antibodies may also be conjugated to different bacterial toxins to yield potent immunotoxins (LeMaistre et al1987; Zimmermann et al1997).

ScFv Abs may be used in combination with cytotoxic agents for the prevention and/or treatment of disease states such as angiogenesis and/or cancer. Cytotoxic agents such as ricin, linked to ScFv Ab may provide a tool for the destruction of cells that bind the ScFv Ab. These cells may be found in many locations, including but not limited to, micrometastases and primary tumours.

Screens

The ScFv Ab of the present invention or a derivative or homologue thereof and/or a cell line that expresses the ScFv Ab of the present invention or a derivative or homologue thereof may be used to screen for agents (such as peptides, organic or inorganic molecules) capable of affecting the binding specificity of the ScFv Ab.

In one embodiment, the screens of the present invention may identify agonists and/or antagonists of the ScFv Ab of the present invention.

In another embodiment, the ScFv Ab of the present invention may be used in a variety of drug screening techniques. The ScFv Ab employed in such a test may be free in solution, affixed to a solid support, borne on a cell surface, or located intracellularly.

The abolition of ScFv Ab binding specificity or the formation of binding complexes between the ScFv Ab and the agent being tested may be measured.

Another technique for screening provides for high throughput screening (HTS) of agents having suitable binding affinity to the ScFv Abs and is based upon the method described in detail in WO 84/03564.

It is expected that the assay methods of the present invention will be suitable for both small and large-scale screening of test compounds as well as in quantitative assays.

Phage Display Screens

Phage display may be employed in the identification of agents, such as a DAM that is engageable by the ScFv Ab of the present invention. Phage display is a protocol of molecular screening which utilises recombinant bacteriophage. The technology involves transforming bacteriophage with a nucleotide sequence encoding an appropriate ligand (such as a candidate DAM) which capable of reacting with a target ScFv Ab (or a derivative or homologue thereof) or the nucleotide sequence (or a derivative or homologue thereof) encoding same. The transformed bacteriophage (which preferably is tethered to a solid support) expresses the appropriate ligand (such as the candidate agent) and displays it on their phage coat. The entity or entities (such as cells) bearing the target ScFv Ab molecules which recognises the candidate DAM are isolated and amplified. The successful candidate DAM is then characterised.

The targeting of cells expressing a DAM with a ScFv Ab of the present invention facilitates the development of ScFv Abs to modulate the activity of cells expressing the DAM In another embodiment of the present invention, an ScFv Ab library may be used to screen for antibodies against specific DAMs. By way of example, a bacteriophage may be transformed with a nucleotide sequence encoding an appropriate ligand (such as a candidate ScFv Ab) which is capable of reacting with a target DAM (or a derivative or homologue thereof) or the nucleotide sequence (or a derivative or homologue thereof) encoding same. The transformed bacteriophage (which preferably is tethered to a solid support) expresses the appropriate ligand (such as the candidate ScFv Ab) and displays it on their phage coat. The entity or entities (such as cells) bearing the target DAM molecules which recognises the candidate ScFv Ab are isolated and amplified. The successful candidate ScFv Ab is then characterised.

By way of further example, a human ScFv fragment library called "the Griffin-1 library" has been constructed by recloning synthetic heavy and light chain variable regions (VH and VL) from the lox library vectors into the phagemid vector pHEN2. Modifications in the elution and screening procedures an result in the successful screening of phage display libraries for ScFv antibodies against a large variety of DAMs (see de Bruin et al 1999, Nature Biotechnology 17: 397-399).

Phage display has advantages over standard affinity ligand screening technologies. The phage surface displays the candidate agent in a three dimensional configuration, more closely resembling its naturally occuring conformation. This allows for more specific and higher affinity binding for screening purposes.

Assays for Mimetics

The positive identification of either a DAM or a ScFv Ab using phage display may faciliate the use of combinatorial libraries to identify mimetics capable of acting in the same or a similiar manner. Such mimetics can be administered alone or in combination with other therapeutics for the treatment of diseases associated with the DAM of the present invention.

Dosage

The dosage of the ScFv Ab of the present invention will depend on the disease state or condition being treated and other clinical factors such as weight and condition of the human or animal and the route of administration of the compound. Depending upon the half-life of the ScFv Ab in the particular animal or human, the ScFv Ab can be administered between several times per day to once a week. It is to be understood that the present invention has application for both human and veterinary use. The methods of the present invention contemplate single as well as multiple administrations, given either simultaneously or over an extended period of time.

Formulations

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

The ScFv Ab of the present invention may be effective in preventing and/or treating diseases such as cancer related diseases. The present invention includes the method of treating diseases such as cancer related disease with an effective amount of a ScFv Ab of the present invention. The ScFv Ab of the present invention can be provided as a synthetic peptide or an isolated and substantially purified proteins or protein fragments or a combination thereof in pharmaceutically acceptable compositions using formulation methods known to those of ordinary skill in the art. These compositions can be administered by standard routes. These include but are not limited to: oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) transdermal, intraperitoneal, intracranial, intracerebroventricular, intracerebral, intravaginal, intrauterine, or parenteral (e.g., intravenous, intraspinal, subcutaneous or intramuscular) routes.

The ScFv Ab formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

In addition, the ScFv Abs of the present invention may be incorporated into biodegradable polymers allowing for sustained release of the compound, the polymers being implanted in the vicinity of where drug delivery is desired, for example, at the site of a tumor or implanted so that the ScFv Ab is slowly released systemically. The biodegradable polymers and their use are described, for example, in detail in Brem et al(J. Neurosurg 1991 74:441-446). Osmotic minipumps may also be used to provide controlled delivery of high concentrations of ScFv Abs through cannulae to the site of interest, such as directly into a metastatic growth or into the vascular supply to that tumor.

The ScFv Abs of the present invention may be linked to cytotoxic agents which are infused in a manner designed to maximize delivery to the desired location. For example, ricin-linked high affinity ScFv Abs are delivered through a cannula into vessels supplying the target site or directly into the target. Such agents are also delivered in a controlled manner through osmotic pumps coupled to infusion cannulae.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

The ScFv Ab conjugates may be administered in any suitable way, usually parenterally, for example intravenously or intraperitoneally, in standard sterile, non-pyrogenic formulations of diluents and carriers, for example isotonic saline (when administered intravenously). Once the ScFv Ab conjugate has bound to the target cells and been cleared from the bloodstream (if necessary), which typically takes a day or so, the pro-drug is administered, usually as a single infused dose, or the tumour is imaged. If needed, because the ScFv Ab conjugate may be immunogenic, cyclosporin or some other immunosuppressant can be administered to provide a longer period for treatment but usually this will not be necessary.

The timing between administrations of the ScFv Ab conjugate and pro-drug may be optimised in a routine way since disease/normal tissue ratios of conjugate (at least following intravenous delivery) are highest after about 4-6 days, whereas at this time the absolute amount of conjugate bound to the DAM, in terms of percent of injected dose per gram, is lower than at earlier times.

Therefore, the optimum interval between administration of the ScFv Ab conjugate and the pro-drug will be a compromise between peak concentration of the enzyme at the disease site and the best distribution ratio between disease and normal tissues. The dosage of the ScFv Ab conjugate will be chosen by the physician according to the usual criteria. At least in the case of methods employing a targeted enzyme such as β-glucosidase and intravenous amygdalin as the toxic pro-drug, 1 to 50 daily doses of 0.1 to 10.0 grams per square metre of body surface area, preferably 1.0-5.0 g/m$^2$ are likely to be appropriate. For oral therapy, three doses per day of 0.05 to 10.0 g, preferably 1.0-5.0 g, for one to fifty days may be appropriate. The dosage of the ScFv Ab conjugate will similarly be chosen according to normal criteria, particularly with reference to the type, stage and location of the disease tissue and the weight of the patient. The duration of treatment will depend in part upon the rapidity and extent of any immune reaction to the ScFv Ab conjugate.

The functional portion of the ScFv Ab conjugate, when the ScFv Ab conjugate is used for diagnosis, usually comprises and may consist of a radioactive atom for scintigraphic studies, for example technetium 99m ($^{99m}$Tc) or iodine-123 ($^{123}$I, or a spin label for nuclear magnetic resonance (nmr) imaging (also known as magnetic resonance imaging, mri), such as iodine-123 again, iodine-313, indium-111, fluorine-19, carbon-13, nitrogen-15, oxygen-17, gadolinium, manganese or iron.

When used in a compound for selective destruction of, for example, the tumour, the functional portion of the ScFv Ab may comprise a highly radioactive atom, such as iodine-131, rhenium-186, rhenium-188, yttrium-90 or lead-212, which emits enough energy to destroy neighbouring cells, or a cytotoxic chemical compound such as methotrexate, adriamicin, vinca alkaliods (vincristine, vinblastine, etoposide), daunorubicin or other intercalating agents.

The radio- or other labels may be incorporated in the ScFv Ab conjugate in known ways. For example, the peptide may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can be attached via a cysteine residue in the peptide. Yttrium-90 can be attached via a lysine residue. The IODOGEN method (Fraker et al(1978) Biochem. Biophys. Res. Commun. 80: 49-57 can be used to incorporate iodine-123. "Monoclonal Antibodies in Immunoscinigraphy" (Chatal, CRC Press 1989) describes other methods in detail.

Pharmaceutical Compositions

In one aspect, the present invention provides a pharmaceutical composition, which comprises an ScFv Ab according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the pharmaceutical composition is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose or chalk, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Administration

Typically, a physician will determine the actual dosage which will be most suitable for an individual subject and it will vary with the age, weight and response of the particular patient and severity of the condition. The dosages below are exemplary of the average case. There can, of course, be individual instances where higher or lower dosage ranges are merited.

The compositions (or component parts thereof) of the present invention may be administered orally. In addition or in the alternative the compositions (or component parts thereof) of the present invention may be administered by direct injection. In addition or in the alternative the compositions (or component parts thereof) of the present invention may be administered topically. In addition or in the alternative the compositions (or component parts thereof) of the present invention may be administered by inhalation. In addition or in the alternative the compositions (or component parts thereof) of the present invention may also be administered by one or more of: parenteral, mucosal, intramuscular, intravenous, subcutaneous, intraocular or transdermal administration means, and are formulated for such administration.

By way of further example, the pharmaceutical composition of the present invention may be administered in accordance with a regimen of 1 to 10 times per day, such as once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The term "administered" also includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Hence, the pharmaceutical composition of the present invention may be administered by one or more of the following routes: oral administration, injection (such as direct injection), topical, inhalation, parenteral administration, mucosal administration, intramuscular administration, intravenous administration, subcutaneous administration, intraocular administration or transdermal administration.

Diseases

Pharmaceutical compositions comprising an effective amount of a ScFv Ab and/or an NOI encoding same may be used in the treatment of disorders such as those listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; diseases associated with viruses and/or other intracellular pathogens; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreoretinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue. Specific cancer related disorders include but not limited to: solid tumours; blood born tumours such as leukemias; tumor metastasis; benign tumours, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; coronnay collaterals; cerebral collaterals; arteriovenous malformations; ischeniic limb angiogenesis; neovascular glaucoma; retrolental fibroplasia; diabetic neovascularization; heliobacter related diseases, fractures, vasculogenesis, hematopoiesis, ovulation, menstruation and placentation.

FIGURES

The invention will now be further described only by way of example in which reference is made to the following Figures:

FIG. 1 which shows a DNA sequence (SEQ ID No 5) encoding a 5T4 ScFv designated 5T4ScFv.1. The sequence of the mature secreted protein (SEQ ID No 1) is provided.

FIG. 2 which shows a DNA sequence encoding a B7-1.5T4.1 fusion protein (SEQ ID No 7). A deduced amino acid sequence for the B7-1.5T4.1 fusion protein (SEQ ID No 3) is also provided.

FIG. 3a which shows a diagrammatic representation of a B7-1.5T4.1 construct.

FIG. 3b which shows a diagrammatic representation of a B7-1.5T4.2 construct.

FIG. 4 which shows a DNA sequence encoding a B7-2.5T4.1 fusion protein (SEQ ID No 9). A deduced amino acid sequence for the B7-2.5T4. 1 fusion protein (SEQ ID No 10) is also provided.

FIG. 5 which shows a B7 link ScFv sequence (SEQ ID No 11).

FIG. 6 which shows a DNA sequence encoding a Ig-5T4 fusion protein (SEQ ID No 8). A deduced amino acid sequence for the Ig-5T4 fusion protein (SEQ ID No 4) is also provided.

FIG. 7 which shows an ScFv-IgE sequence (SEQ ID No 12).

FIG. 8 which shows a B7-EGF sequence (SEQ ID No 13).

FIG. 9 which shows the effect of the ScFv Ab on CT26-neo tumour cell growth in Balb/c mice over a period of 35 days.

FIG. 10 which shows the effect of the ScFv Ab on CT26-h5T4 tumour cell growth in Balb/c mice over a period of 35 days.

FIG. 11 which shows the effect of the ScFv Ab on B16-neo tumour cell growth in Balb/c mice over a period of 35 days.

FIG. 12 which shows the effect of the ScFv Ab on B16-h5T4 tumour cell growth in Balb/c mice over a period of 35 days.

FIG. 13 shows ScFv constructs.
FIG. 14 shows a B7-scFv binding to the 5T4 target antigen.
FIG. 15 shows B7-scFv binding to CTLA4.
FIG. 16 shows FACS analysis of A9-5T4 (A) and A9-neo (5T4 negative) (B) cells incubated with scFv protein alone or scFv-HG1 fusion protein followed by goat anti-human IgG-FITC labelled antibody.
FIG. 17 shows 5T4 scFv-Hγ1 ADCC Activity.
FIG. 18 shows pONY8.1SM
FIG. 19 shows fusion protein constructs in pONY 8.1SM
  a. B7-5T4scFv
  b. L-5T4scFv
FIG. 20 shows pKLink
FIG. 21 shows an scFv and leader sequence in pBSII
FIG. 22 shows Leader-IL-5 scFv in pONY8.1SM
FIG. 23 shows Leader HIV-gp120 scFv in pONY8.1SM
FIG. 24 shows pAdApt
FIG. 25 shows Fusion protein constructs in pAdApt
  a. B7-5T4scFv
  b. L-5T4scFv
FIG. 26 shows the canine 5T4 coding sequence

IN SLIGHTLY MORE DETAIL

Figure 3A:
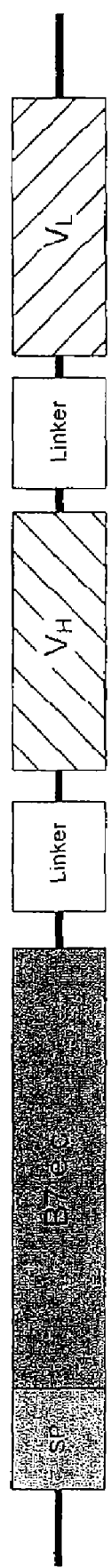

FIG. 20 shows the pKLink—the (Gly$_4$Ser)$_3$ linker in pBluescript II SK (pBS II). The flexible linker is synthesised as two complemantary oligonucleotides, that are annealed to give restriction enzyme overhangs and then cloned as a double stranded oligonucleotide into pBSII. The amino acid translation of (glycine$_4$ serine)$_3$ is shown in single letter code below the DNA sequence.

FIG. 21 shows a scFv (for example an IL-5 or HIV gp120 scFv) in PBSII and subsequent addition of the leader sequence. In this example the VH is amplified with additional Spe I and Mfe I restriction sites at the 5' end and an additional Age I site at the 3' end. The Spe I and Age I sites are used to clone into pKlink. The VL is amplified with an additional Bam HI restriction site at the 5' end and an additional Eco RI site at the 3'end, which are used for cloning into pKlink. The leader signal peptide is synthesised as two complemantary oligonucleotides, that are annealed to give restriction enzyme overhangs and then cloned as a double stranded oligonucleotide between the Spe I and Mfe I sites at the 5' end of the scFv cDNA. The Kozak sequence including the ATG start codon (underlined) is in bold and italics.

FIG. 26 shows the canine 5T4 coding sequence. A mongrel genomic library in λ dash was screened with a probe made from h5T4 cDNA. Positive clones were identified and sequenced.

EXAMPLES

Example 1

Construction of 5T4 ScFv Ab and Retroviral—Vector Delivery to Tumour

The cDNA encoding the murine 5T4 monoclonal antibody is cloned and sequenced by standard techniques (Antibody engineering: a practical approach ed McCafferty et al. 1996 OUP). The sequence of the variable region of the antibody can be used to construct a ScFv antibody. The coding sequence of a 5T4 ScFv, called 5T4ScFv. 1 (SEQ ID No 1), is shown in FIG. 1. In this molecule, the DNA sequence encodes the VH from the mouse 5T4 monoclonal antibody followed by a 15 amino acid flexible linker and the VL region of the mouse 5T4 antibody. The flexible linker encodes 3 copies of the amino-acid sequence gly-gly-gly-gly-ser and the DNA sequence similarity between the repeats has been minimised to avoid the risk of recombination between the repeats when plasmids containing them are grown in *E. coli*.

DNA Cassettes

Cassette 1—Translation Initiation Signal and Signal Peptide

In order to achieve correct translation initiation and secretion from mammalian cells, the following sequence is used (SEQ ID NO 16):

```
                                                    (SEQ ID NO:38)
AagcttCCACCATGGGATGGAGCTGTATCATCCTCTTCTTGGTAGCAACA
GCTACAGGTGTCCACTCC
```

This contains a convenient HindIII restriction site for cloning into expression vectors (lower case), the consensus translation initiation signal for mammalian cells (ANNATGPu) and the coding sequence for a signal peptide sequence from an immunoglobulin gene.

Cassette 2-scFv

The sequence of the secreted portion of the 5T4ScFv.1 is shown in FIG. 1. This molecule can be represented as Vh-(gly$_4$-ser)$_3$ linker-V1.

The 5T4 ScFv2 Ab consists of the 5T4 variable region sequences connected in the order V1—flexible linker Vh. In this case the linker encodes the 20 amino-acid peptide (gly$_4$-ser)$_4$. A longer linker improves assembly of the ScFv when the V-region segments are in this order. (Pluckthun et al in Antibody Engineering: a practical approach, ed McCafferty et al. 1996 OUP).

Expression of a 5T4 Specific ScFv

For expression of a 5T4-specific ScFv in human cells, the coding sequence is inserted into the vector pCIneo (Promega) under the control of a strong promoter and polyadenylation signal. The translation initiation signal and immunoglobulin leader (signal peptide) sequence from Cassette 1 at the 5'end of the coding region ensure efficient secretion of the ScFv from mammalian cells.

Example 2

Transfection of Macrophages/Monocytes with an Expression Vector Encoding an ScFv Ab Peripheral blood mononuclear cells are isolated from human peripheral blood at laboratory scale by standard techniques procedures (Sandlie and Michaelsen 1996 In Antibody engineering: a practical approach. Ed McCafferty et al. Chapter 9) and at large scale by elutriation (eg Ceprate from Cell-Pro). Adherent cells (essentially monocytes) are enriched by adherence to plastic overnight and cells can be allowed to differentiate along the macrophage differentiation pathway by culturing adherent cells for 1-3 weeks.

Monocytes and macrophages are transfected with an expression vector capable of expressing a ScFv Ab in human cells. For constitutive high level expression, the ScFv Ab is expressed in a vector which utilises the hCMV-MIE promoter-enhancer, pCI (Promega). For hypoxia-induced expression, the hCMV promoter is replaced by a promoter containing at least one HRE. A suitable promoter is a truncated HSV TK promoter with 3 copies of the mouse PGK HRE (Firth et al. 1994 Proc. Natl. Acad. Sci. 91: 6496-6500).

A variety of transfection methods can be used to introduce vectors into monocytes and macrophages, including particle-mediated DNA delivery (biolistics), electroporation, cationic agent-mediated transfection (eg using Superfect, Qiagen). Each of these methods is carried out according to the manufacturer's instructions, taking into account the parameters to be varied to achieve optimal results as specified by the individual manufacturer. Alternatively, viral vectors may be used such as defective Adenovirus vectors (Microbix Inc or Quantum Biotechnologies Inc).

Example 3

Construction of B7—ScFv Fusion Proteins

The extracellular domain of B7-1 is defined by amino-acid residues 1-215 of the native human B7-1 protein. This sequence, together with its signal peptide-encoding sequence, is used to construct secreted fusion proteins which also contain the ScFv derived from the 5T4 monoclonal antibody. The sequence of the 5T4 ScFv is given in FIG. 1.

Figure 3B:
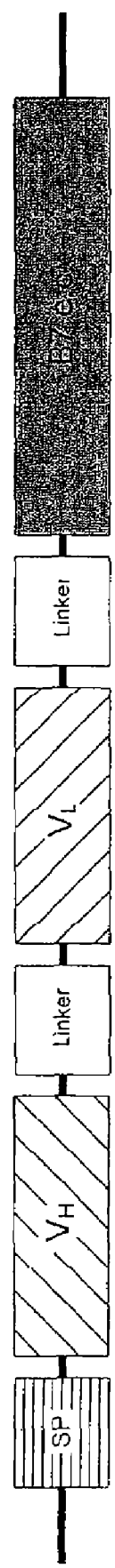

A DNA coding sequence is constructed using standard molecular biology techniques which encodes a fusion protein in which the N-terminus of the 5T4 ScFv is fused after amino acid 215 of human B7-1. The sequence of this coding sequence, B7-1.5T4.1 (SEQ ID No 7) is shown in FIG. 2. The fusion protein contains a flexible (gly-gly-gly-gly-ser) spacer between the B7-1 and 5T4 ScFv sequences. The introduction of a convenient BamH1 restriction site at the end of the linker insertion (beginning at nucleotide 733) also allows for further linkers to be screened for optimal expression of bi-functional fusion protein. FIG. 3 indicates the fusion protein in diagrammatic form. It is similarly possible to construct B7-1.5T4.2 (FIG. 3b) in which the ScFv is N-terminal and the B7 extracellular domain is C-terminal. In this case only the coding sequence of the mature B7-1 (without signal peptide) is required. A signal peptide such as an immunoglobulin leader sequence is added to the N-terminus of the ScFv in this instance.

For fusion proteins which use the co-stimulatory extracellular domain of B7-2 (Gerstmayer et al 1997 J Immunol 158 (10): 4584-90), the signal peptide and extracellular domain of B7-2 is used in place of B7-1 sequences. FIG. 4 shows the coding sequence of the SCM B7-2.5T4.1 co-stimulatory domain. It encodes the first 225 amino acids of human B7-2, preceded by its signal peptide, and a flexible linker (gly4-ser). The BamHI site at the end of this sequence can be used to insert the domain upstream of the 5T4ScFv.1 (see FIG. 3). The sequence includes the B7-2 signal peptide which can serve to allow secretion of this fusion protein in which the B7-2 domain is at the N-terminus of the fusion protein.

Each engineered cDNA is inserted into the mammalian expression vector pCI to allow expression in mammalian tissue culture cells. For this purpose, a linker sequence is added to the 5'-end of the coding sequence which introduces a convenient restriction site for insertion into the polylinker of pCI and adds the translation initiation signal CCACC immediately adjacent to the first ATG codon. Constructs in pCI are transfected into a suitable mammalian host cell line such as COS-1 to confirm secretion of the SCM. The transcription cassette from pCI or an appropriate segment of the transcription cassette is subsequently sub-cloned into the expression vector to be used as the gene delivery system for therapeutic use.

Example 4

Transfection of Macrophages/Monocytes with an Expression Vector Encoding a ScFv Ab Comprising a Secreted Co-stimulatory Molecule (SCM)

Peripheral blood mononuclear cells are isolated from human peripheral blood at laboratory scale by standard techniques procedures (Sandlie and Michaelsen 1996 In Antibody engineering: a practical approach. Ed McCafferty et al. Chapter 9) and at large scale by elutriation (eg Ceprate from Cell-Pro). Adherent cells (essentially monocytes) are enriched by adherence to plastic overnight and cells can be allowed to differentiate along the macrophage differentiation pathway by culturing adherent cells for 1-3 weeks.

Monocytes and macrophages are transfected with an expression vector capable of expressing an ScFv Ab comprising an SCM in human cells. For constitutive high level expression, the SCM is expressed in a vector which utilises the hCMV-MIE promoter-enhancer, pCI (Promega). For hypoxia-induced expression, the hCMV promoter is replaced by a promoter containing at least one HRE. A suitable promoter is a truncated HSV TK promoter with 3 copies of the mouse PGK HRE (Firth et al. 1994 Proc. Natl. Acad. Sci. 91: 6496-6500).

A variety of transfection methods can be used to introduce vectors into monocytes and macrophages, including particle-mediated DNA delivery (biolistics), electroporation, cationic agent-mediated transfection (eg using Superfect, Qiagen). Each of these methods is carried out according to the manufacturer's instructions, taking into account the parameters to be varied to achieve optimal results as specified by the individual manufacturer. Alternatively, viral vectors may be used such as defective Adenovirus vectors (Microbix Inc or Quantum Biotechnologies Inc).

Example 5

Analysis of SCM Binding to CTLA-4 and 5T4-antigen Expressing Cells

The B7-1 or B7-2 domains of an ScFv Ab-SCM fusion protein are expected to bind specifically to CD28 and CTLA-4 present on human T-cells. Binding to T-cells or Chinese hamster ovary cells transfected with human CTLA-4 or CD28 is determined using FACS analysis as follows. $5 \times 10^5$ CTLA-4 expressing target cells or equivalent cells lacking CTLA-4 (untransfected CHO cells) are incubated with 0.1 ml culture supernatant from COS-1 cells transiently transfected with SCM genes for 1 h at 4° C. The cells are washed and incubate with 1 mg monoclonal antibody specific for the B7 domain (eg Mab 9E10) followed by FITC-labelled goat anti-mouse IgG (Pharmingen) and analysis by FACS.

Binding of ScFv to 5T4-antigen is similarly assessed using target cells expressing 5T4-antigen (5T4-transfected A9 cells) or control cells (A9).

Example 6

Analysis of Co-stimulatory Activity

An established mouse cell line of Balb/c origin such as HC11 cells is transfected with the cDNA encoding human 5T4-antigen (Myers et al. 1994 J. Biol. Chem. 269; 9319-9324) inserted in the expression vector pCIneo.

Splenic T-cells from Balb/c mice are isolated by standard procedures (Johnstone and Thorpe 1996 In Immunochemistry in Practice. Blackwell. Chapter 4). T-cells are pre-stimulated by incubation for 1-2 days in medium containing 10 ng/ml PMA (Sigma) and 100 U/ml human IL-2 (Boehringer Mannheim). HC11-5T4 cells are incubated at $10^4$ cells /well of a 96-well tissue culture tray for 2 h with up to 0.1 ml supernatant from COS cells transfected with SCM gene. Up to $10^5$ pre-stimulated T-cells are added to each well, the cells are pulsed with 0.25 mCi/well $^3$H-thymidine and incorporation of $^3$H-thymidine is measured using a liquid scintillation counter after 24 h.

Example 7

Analysis of co-stimulation in Animal Models

HC11 cells transfected with the human 5T4-antigen gene are grown as tumours in Balb/c mice. SCM genes B7-1.5T4.1 or B7-2.5T4.1 or a combination of both genes are introduced into the tumour cells prior to implantation and the growth of the tumours and the growth of control tumours which do not express SCM genes in vivo are monitored.

Example 8

Construction of a B7-1/ScFv, Specific for Human 5T4, Fusion Protein

Standard molecular biology techniques are used to construct a fusion protein consisting of the leader sequence and extracellular domain of B7-1, fused via a flexible linker to the $V_H$ and $V_L$ of the murine Mab 5T4 specific to human 5T4.

The flexible linker, used to join the extracellular domain of B7.1 and the ScFv, was constructed by annealing two homologous oligonucleotides with engineered 5' Sma I and 3' Spe I sites—using oligonucleotides

```
Upper                              (SEQ ID NO:6)
5' GGG GGT GGT GGG AGC GGT GGT GGC GGC AGT GGC GGC
GGC GGA A 3' and lower                          (SEQ ID NO:16)
5' CTA GTT CCG CCG CCG CCA CTG CCG CCA CCA CCG CTC
CCA CCA CCC CC 3'
```

The linker is cloned into pBluescript (Stratagene) via Sma I and Spe I to produce pLINK. The signal peptide (sp) and extracellular domain of murine B7.1 were ampified by PCR from pLK444-mB7.1 (supplied by R. Germain NIH, USA) via primers that introduce 5' EcoRI and 3' Sma I sites—primers forward The linker is cloned into pBluescript (Stratagene) via Sma I and Spe I to produce pLINK. The signal peptide (sp) and extracellular domain of murine B7.I were amplified by PCR from pLK444-mB7.I (supplied by R. Germain NIH, USA) via primers that introduce 5' EcoRI and 3'

```
Sma I sites - primers forward      (SEQ ID NO:17)
5' C TCG AAT TCC ACC ATG GCT TGC AAT TGT CAG TTG
ATG C 3' reverse                            (SEQ ID NO:18)
5' CTC CCC GGG CTT GCT ATC AGG AGG GTC TTC 3'
```

The B7.1 PCR product was cloned into pLINK via Eco RI and Sma I to form pBS/B7Link.

The $V_H$ and $V_L$ of the 5T4 specific ScFv was amplified via primers—

```
forward primer                     (SEQ ID NO:19)
5' CTC ACT AGT GAG GTC CAG CTT CAG CAG TC 3' reverse primer                     (SEQ ID NO:20)
5' CTC GCG GCC GCT TAC CGT TTG ATT TCC AGC TTG GTG
CCT CCA CC 3'
``` that introduce 5' Spe I and 3' Not I sites from pHEN1-5T4 ScFv. PBS/B7Link was digested with Spe I and Not I and ligated with the ScFv to form OBM 233 consisting of the sequence shown as SEQ ID No. 11: B7 Link ScFv sequence (FIG. 5).

This fusion can be used to construct a recombinant vector e.g. retrovirus, Lentivirus, adenovirus, poxvirus, vaccinia virus, baculovirus. Such vectors can be used to inject patient tumours directly. To deliver the fusion protein to tumour cells the recombinant vector is used to transduce macrophages/monocytes/CD34+ cells ex vivo before injection back into patients. These cells will traffic to tumours. The ScFv will bind to a specific tumour antigen expressed on the surface of tumour cells e.g. 5T4 (Myers et al 1994 JBC). B7 is found on the surface of professional antigen presenting cells e.g. macrophages, dendritic cells and B cells. It interacts with it ligands CD28 and CTL-A4 located on CD4 and CD8 cells. The simultaneous interaction of B7-CD28/CTL-A4 and MHC-peptide/T cell receptor leads to a pronounced increase in IL-2 which promotes CD8 (cytotoxic T cell) expansion (Linsley P S, Brady W, Grosmaire L, Aruffo A, Damle N K, Ledbetter J A J Exp Med 1991 Mar 1; 173(3):721-730 Binding of the B cell activation antigen B7 to CD28 costimulates T cell proliferation and Il-2 mRNA accumulation.) Tumour cells that have been B7 tranfected with B7 have been shown retardation in animal models (Townsend S E, Allison J P Science 1993 15;259(5093):368-370).

Example 9

Transient Expression and Purification of B7-1/ScFv and Leader ScFv(LScFv)

For transient expression of B7-1/ScFv the human CMV expression plasmid pCIneo (Promega) was used. B7/ScFv was excised from OBM 233 by digestion with EcoR I/Not I and cloned into pCIneo that was previously digested with EcoRI/Not I. Transient expression of recombinant protein is made by transfection of 293T cells with the relevant plasmid using calcium phosphate (Profectin, Promega). Conditions used were similar to those recommended by the manufacturer. To reduce bovine serum contamination serum free optimum media (Gibco BRL). After 36-48 hours transfection supernatants were harvested and spun through a Centriprep (Amicon, Glos. UK) 10 filter (all proteins larger than 10 kDa are purified/concentrated) and a Centricon (Amicon) 10 filter. Supernatants are concentrated approximately 30 fold.

For B7-1 to be biologically functional it must be able to display binding with one of it's natural ligands either CTLA-4 or CD28 found on the surface of specific populations of T cells (e.g CD4+). The biological activity B7-1/ScFv fusion protein was analysed for simultaneous interaction with its natural ligand CTLA-4 (in the form of CTLA4-Ig supplied by Ancell, MN, USA) and A9 cells expressing human 5T4. Briefly: approximately. $5 \times 10^5$ A9-h5T4 cells were incubated with 100 ul of either B7.1/ScFv or LScFv supernatant in a U bottom 96 well plate at 4° C. for 1 hour. After washing cells were incubated with CTLA4-Ig (Ancell) for 1 hour. After washing, bound CTLA4-Ig was detected using an FITC conjugated anti-mouse Ig (Dako).

Results show obvious binding of CTLA-Ig with the B7-1 extracellular domain, bound via the ScFv, to the surface of human 5T4 positive A9 cells. The lack of binding activity with 5T4 negative A9 cells further illustrates that the interaction of B7 with CTLA4-Ig and ScFv with 5T4 are specific.

Example 10

ScFv-IgG Fusion Example

Construction of ScFv-IgG

The sequence encoding a translation initiation sequence and the human immunoglobulin kappa light chain signal peptide is synthesised as two complementary single stranded oligonucleotides which when annealed also contain an internal Xho I site at the 5' end and in addition leave a Xba I compatible 5' overhang and a Pst I compatible 3' overhang

```
                                        (SEQ ID NO:21)
ctagactcgagCCACC ATG GGA TGG AGC TGT ATC ATC CTC
TTC TTG GTA GCA ACA GCT ACA GGT GTC CAC TCC GAG
GTC CAG ctgca
and
                                        (SEQ ID NO:22)
g CTG GAC CTC GGA GTG GAC ACC TGT AGC TGT TGC TAC
CAA GAA GAG GAT GAT ACA GCT CCA TCC CAT GGTGGctcga
gt
```

This is then cloned into pBluescript II (Stratagene) restricted with Xba I and Pst I to create pBSII/Leader.

The 5T4 ScFv is amplified by PCR from pHEN1 using oligonucleotides which incorperate a Pst I site at the 5' end of the product and a Hind III at the 3' end

```
GTC CAG CTG CAG CAG TCT GG             (SEQ ID NO:23)
and
CG TTT GAT TTC AAG CTT GGT GC          (SEQ ID NO:24)
```

This is then restricted with those enzymes and inserted into pBSII/Leader restricted with the same enzymes, creating pBSII/Leader/ScFv.

The HIgG 1 constant region is amplified by PCR from the cloned gene using oligonucleotides which incorporate a Hind III site at the 5' end and a Xho I site at the 3' end

```
                                        (SEQ ID NO:25)
gcgc AAG CTT gaa atc aaa cgg GCC TCC ACC AAG GGC
CCA
and
                                        (SEQ ID NO:26)
gcgc ctcgag TCA TTT ACC CGG AGA CAG GG
```

This is then restricted with those enzymes and inserted into pBSII/Leader/ScFv restricted with the same enzymes, creating pBSII/Leader/ScFv/HG1. The sequence for this construct is shown in the FIG. 4 (SEQ ID NO: 10).

This fusion can be used to construct a recombinant vector e.g. retrovirus, Lentivirus, adenovirus, poxvirus, vaccinia virus, baculovirus. Such vectors can be used to inject patient tumours directly. To deliver the fusion protein to tumour cells the recombinant vector is used to transduce macrophages/monocytes/CD34+ cells ex vivo before injection back into patients. These cells will traffic to tumours. The ScFv will bind to a specific tumour antigen expressed on the surface of tumour cells e.g. 5T4 (Myers et al 1994 JBC). Bound IgG will promote specific tumour destruction via a collection of mechanisms collectively known as antibody dependent cellular cytotoxicity (Munn et alCan res 1991 ibid, Primus et al 1993 Cancer Res ibid).

Example 11

Construction of ScFv-IgE1 (Human IgE1 Heavy Constant Region)

A similar fusion construct of 5T4 ScFv—human IgE constant heavy chain is made consisting of the sequence shown as FIG. 7 (SEQ ID No. 12).

This fusion construct is made by amplifying the human IgE1 constant heavy region by PCR cDNA derived from human B-cells RNA by RT and subsequently using oligonucleotides which incorporate a Hind III site at the 5' end and a Xho I site at the 3' end

```
                                        (SEQ ID NO:27)
gcgc AAG CTT gaa atc aaa cgg GCC TCC ACA CAG AGC
CCA
```
and

```
                                        (SEQ ID NO:28)
gcgc ctcgag TCA TTT ACC GGG ATT TAC AGA
```

This is then restricted with those enzymes and inserted into pBSII/Leader/ScFv restricted with the same enzymes, creating pBSII/Leader/ScFv/HE1.

As described above the ScFv-IgE construct can be incorporated into a recombinant viral vector for use in gene therapy of cancer e.g. inject patient tissue directly or to transduce patient derived macrophages/moncytes/CD34+ cells ex vivo. The fusion protein will be secreted and will bind to tumour cells bearing the antigen that the ScFv is specific for. Binding of IgE to tumour cells should promote a strong histamine response via activation of mast cells. This will lead to a strong inflammatory response and destruction tumour cells as is reported for IgE cytotoxic destruction of parasites e.g. helminth larvae (Capron M 1988 Eosinophils in diseases: receptors and mediators. In progress in allergy and clinical immunology (Proc. 13$^{th}$ Int. Congress of Allergy and Clinical Immunology) Hogrefe & Huber Toronto p 6). Such inflammation and tumour destruction should initiate the recruitment of other immune effector cells. Past reports indicate that treatment with an MMTV antigen specific IgE Mab leads to protection from a tumour expressing MMTV antigen (Nagy E Istanvan B, Sehon A H 1991 Cancer Immunol. Immunotherapy vol 34:63-69).

Example 12

Construction of B7/EGF

B7—EGF Synthetic Gene.

A fusion construct of B7—EGF is made by inserting a PCR product amplified from the region of the gene encoding the mature EGF peptide (see accession number X04571) into pBS/B7 Link. This construct has the sequence shown in FIG. 8 (SEQ ID No. 13).

Using cDNA derived by RT of RNA isolated from a cell line such the 293 human kidney line (ATCC: CRL1573), the DNA is amplified by PCR using oligonucleotides containing a Spe I restriction enzyme site at the N-terminus and a stop codon and a Not I site at the C-terminus

```
                                        (SEQ ID NO:29)
GG ACT AGT AAT AGT GAC TCT GAA TGT CCC
```
and

```
                                        (SEQ ID NO:30)
ATT AGC GGC CGC TTA GCG CAG TTC CCA CCA CTT C
```

The resulting product is digested with those enzymes and ligated to pBS/B7 Link which has been restricted with the same enzymes creating pBS/B7 Link EGF. The B7 Link EGF cassette is then excised with Eco RI and Not I and inserted into a derivative of pHIT111 (Soneoka et al, 1995, Nucl Acid Res 23; 628) which no longer carries the LacZ gene.

An alternative to using ScFv is to use growth factors that have a high affinity to their corresponding receptor e.g. epidermal growth factor which binds to several receptors including erb-2 which is highly associated with tumourgenesis.

As described above the fusion construct can be incorporated into a recombinant viral vector for use in gene therapy e.g. inject patient tissue directly or to transduce patient derived macrophages/moncytes/CD34+ cells ex vivo. The fusion protein will be secreted and will bind to tumour cells bearing the erb-2 antigen.

Epidermal growth factor (EGF) will bind to its ligand erb-2 (an EGF receptor) thus obviating the requirement of a ScFv. Erb-2 is highly associated with tumour cells (Hynes N E Semin Cancer Biol February 1993;4(1):19-26, Amplification and over expression of the erbB-2 gene in human tumors: its involvement in tumor development, significance as a prognostic factor, and potential as a target for cancer therapy). B7 is found on the surface of professional antigen presenting cells e.g. macrophages, dendritic cells and B cells. It interacts with it ligands CD28 and CTL-A4 located on CD4 and CD8 cells. The simultaneous interaction of B7-CD28/CTL-A4 and MHC-peptide/T cell receptor leads to massive increase in IL-2 which promotes CD8 (cytotoxic T cell) expansion (Linsley P S, Brady W, Grosmaire L, Aruffo A, Damle N K, Ledbetter J A J Exp Med Mar. 1,1991;173(3):721-730 Binding of the B cell activation antigen B7 to CD28 costimulates T cell proliferation and interleukin 2 mRNA accumulation.) Tumour cells that have been B7 transfected with B7 have shown retardation in animal models (Townsend S E, Allison J P Science 1993 15;259(5093):368-370 Tumor rejection after direct costimulation of CD8+ T cells by B7-transfected melanoma cells). It is has been reported that B7 will enhance the CTL response to tumour antigens specific to tumour cells thus leading to the destruction of all such cells.

Example 13

Production of Cell Lines Expressing Fusion Constructs

The ScFv-IgG gene was excised from pBSII/L/ScFv/hIgG1 by Xho I digestion, and cloned into pLXSN via the Xho I site, to make pLXSN/ScFv-IgG, such that after chromosomal integration it is under transcriptional control of the LTR. Virus was made in the human kidney cell line 293T by co-transfecting plasmids containing the MLV gap-pol genes (pCIEGPPD) and and the VSV G envelope (pRV67) using the triple plasmid HIT system (Landau & Littman 1992 J Virol 66 5110, Soneoka Y et al 1995 NAR 23:628-633). Virus is harvested after 48 hours and used to transduce BHK-21 cells (ATCC# CCL-10). Approximately 24 hours post-transduction, transduced cells are selected by the addition of 1 mg/ml G418 (Gibco BRL) to culture medium. The supernatant from positive colonies was harvested and concentrated by centrifugation through a Centriprep (Amicon, Glos. UK) 10 filter (all proteins larger than 10 kDa are purified/concentrated) and a Centricon (Amicon) 10 filter. Supernatants were concentrated approximately 30 fold.

Other fusion proteins are cloned into pLXSN via the Xho I site and expressed and concentrated using a similar protocol.

FACS Analysis of Fusion Protein Binding with Cells Expressing Specific Ligand

To determine if the ScFv-IgG fusion protein is specific for its antigen, human 5T4, FACS analysis of a human bladder carcinoma tumour line (EJ) or a stable murine cell line expressing h5T4, A9-h5T4 (Myers et al 1994 JBC) and a 5T4 negative line A9-neo was carried out. Approximately $5 \times 10^5$ A9 or EJ cells, in a round bottom 96 well plate (Falcon) were incubated with 100 ul of a 1:5 dilution of concentrated supernatant (as described above) for 1 hour at 4° C. After washing, bound protein is detected using 5 an anti human IgG/FITC conjugated antibody (Dako). Cells were analysed on a Becton Dickinson FACS machine. FACS results show that there is at least a 1 log shift in fluorescence activity in those 5T4 positive cells treated with the ScFv-IgG construct compared to the negative control construct consisting of the ScFv protein alone. A9 neo FACS shows that there is no non-specific binding of the ScFv component of the fusion protein.

FACS analysis of ScFv-IgE is carried out similar to above except that anti-human IgE-FITC (Dako) is used to detect binding of the fusion protein.

The B7/EGF fusion protein is analysed for binding using FACS and HC11-erb-2 positive cells (Hynes et al 1990). CTLA4-Ig (Ancell, USA) is used to analyse the bioactivity of the B7 component of the bound fusion protein. Anti-mouse IgG-FITC is used to show CTLA-4 binding.

Analysis of Fusion Proteins

Facs Analysis of B7-scFv

Figure 13:
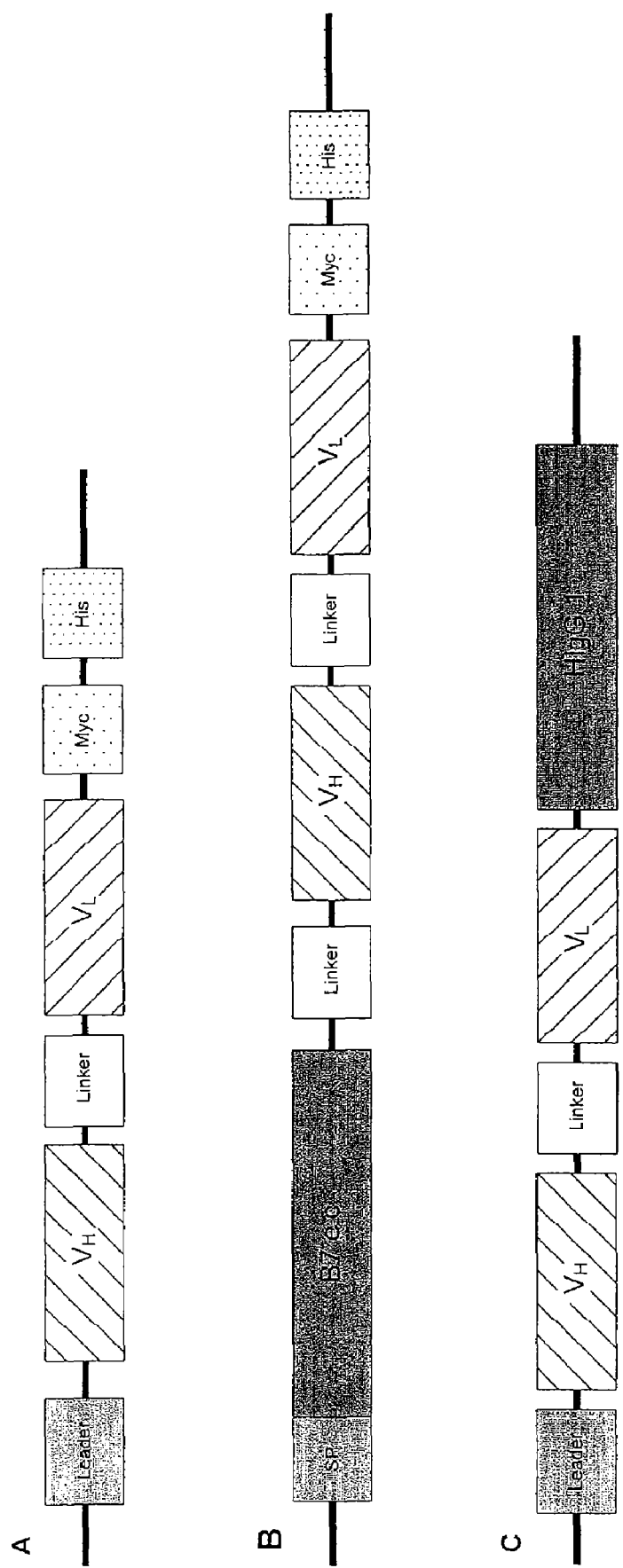
Figure 14:
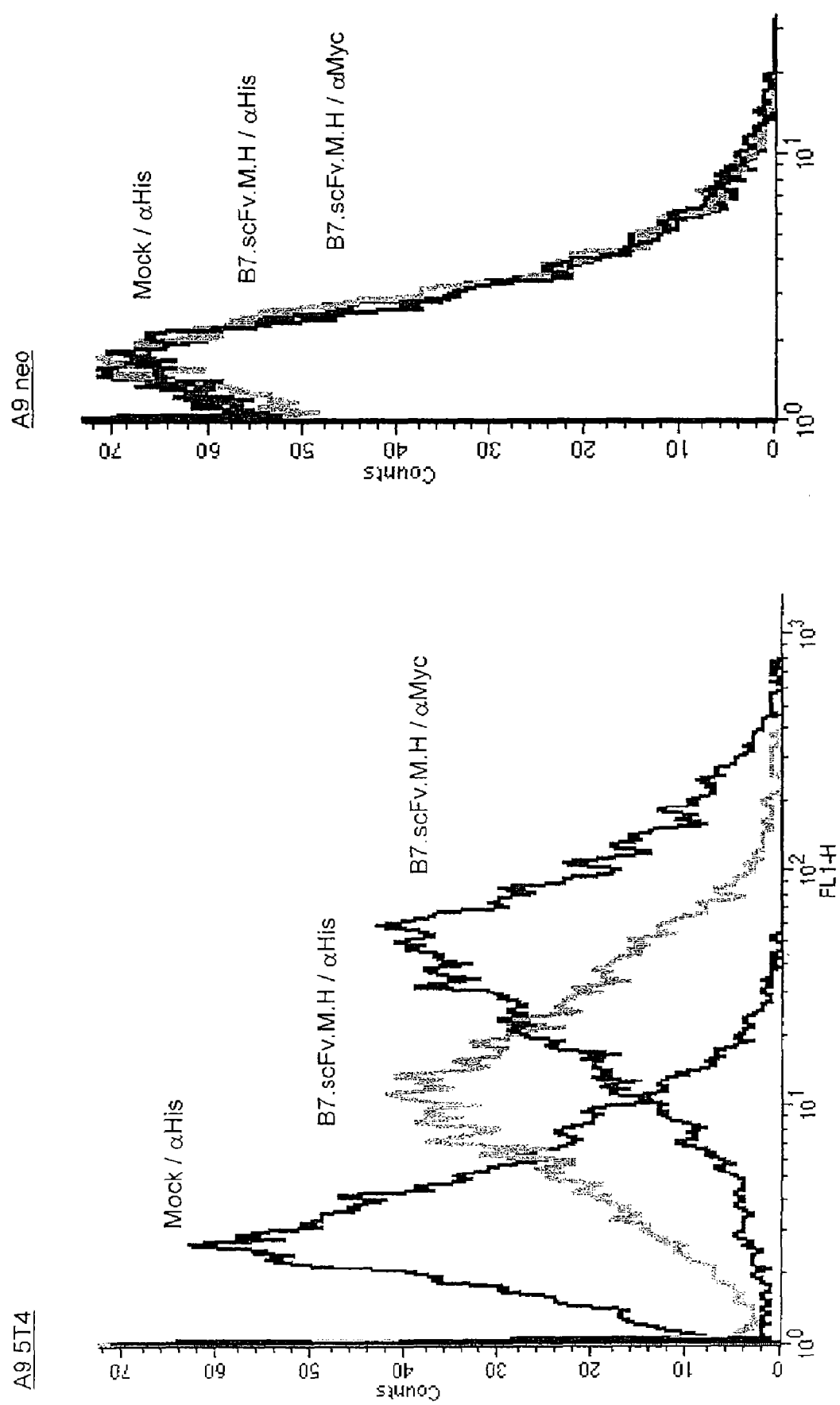
FIG. 14 shows supernatants from mock transfected 293T cells or those transfected with the tagged B7-scFv construct were incubated with A9 5T4 and A9 neo cells. Detection used FITC conjugated αHis or αMyc antibodies.

Recombinant protein was generated by expression from a stably transfected BHK-21 cell line as described below (to allow identification and also purification) c-terminal to the scFV (FIG. 13B) in the plasmid pCIneo (Promega). To demonstrate that the scFv is able to bind to the 5T4 antigen, supernatants from these and from mock transfected 293T cells were added to mouse A9 cells expressing h5T4 (stable transfectants with a h5T4/neomycin resistance expression construct). Detection using FITC conjugated αHis or αMyc antibodies confirmed binding of the scFv to the A9-5T4 cells but not 5T4 negative A9 neo cells indicating that the fusion construct is able to bind the target antigen (FIG. 14).

Figure 15:
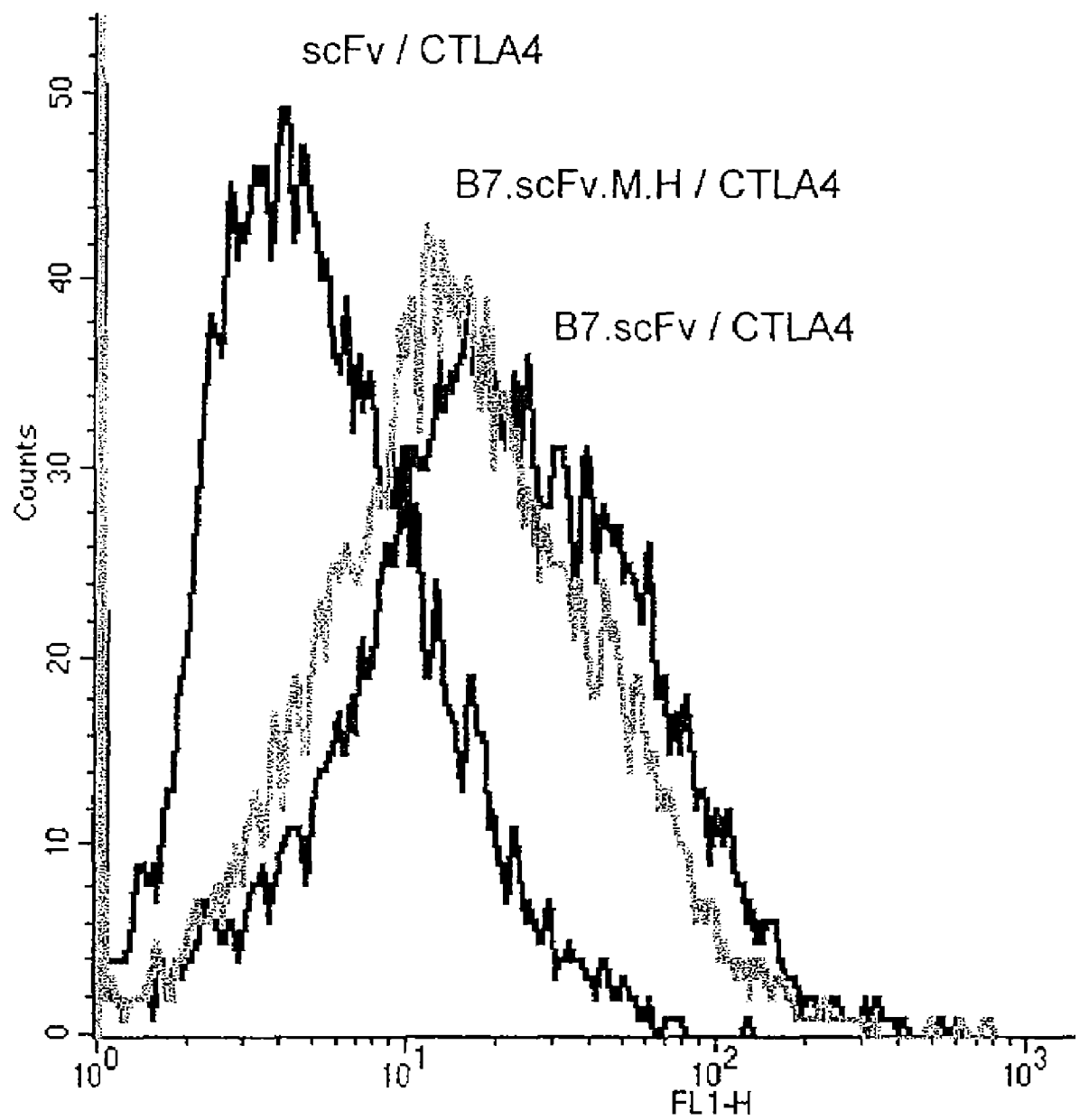
FIG. 15 shows A9 5T4 and A9 neo cells which were incubated with the scFv alone, a B7-scFv construct lacking the Myc-His tag or the tagged B7-scFv construct. The B7.1 ligand, CTLA4-Ig was added and detection used FITC conjugated αmouse IgG.

Further FACS analysis was undertaken to show that the B7-scFv protein is able to bind simultaneously the B7.1 ligand, CTLA4 and cells expressing h 5T4. A9 5T4 and A9 neo cells were incubated with the scFv alone, a B7-scFv construct lacking the Myc-His tag or the tagged B7-scFv construct. The B7.1 ligand, CTLA4-Ig was added and detected using FITC conjugated amouse IgG (FIG. 15). The presence or absence of the Myc-His tag made little difference to the simultaneous binding of the protein to 5T4 antigen and CTLA-4.

Analysis of 5T4 scFv HIgG 1 Protein

Figure 16:
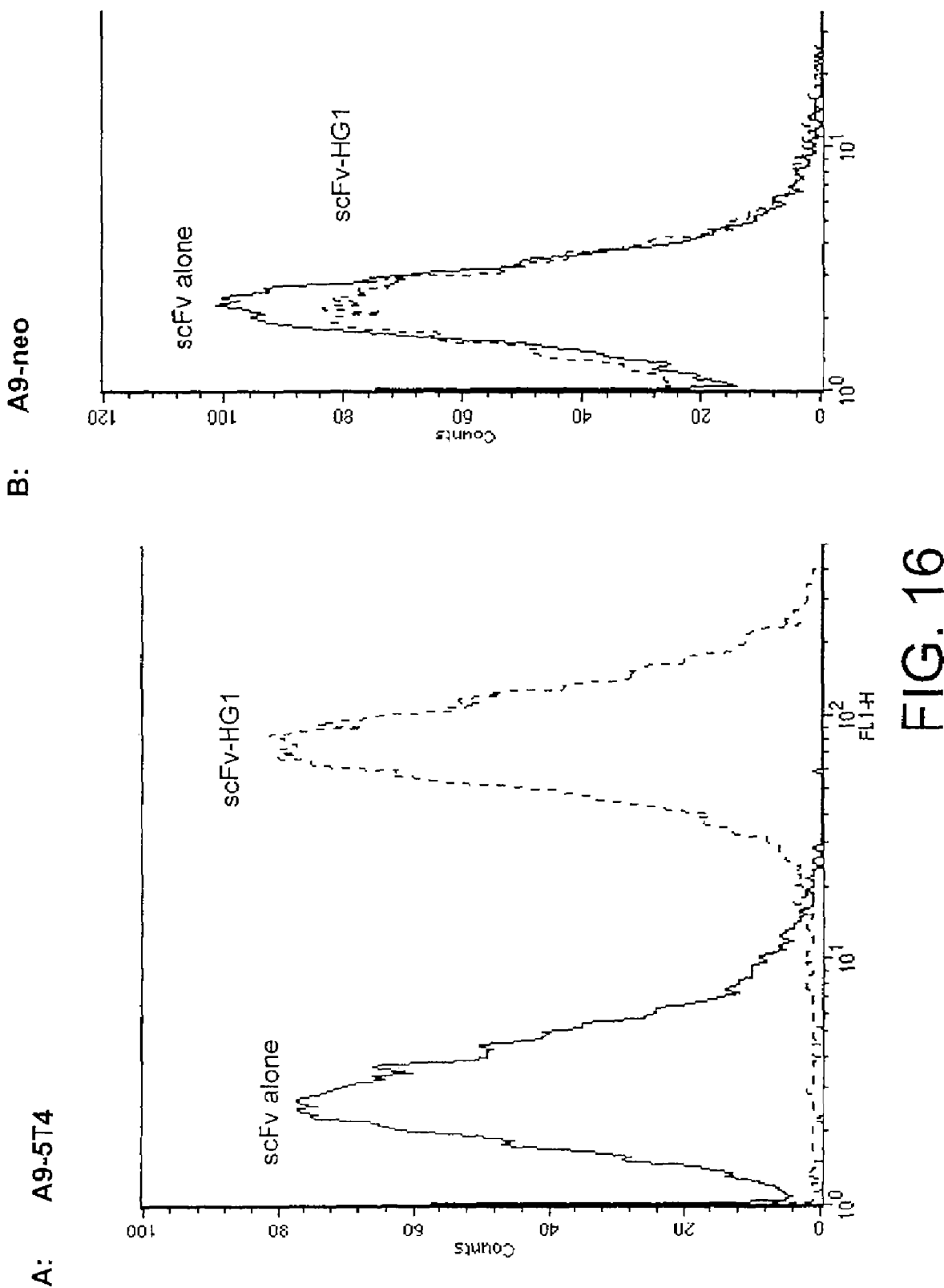

Recombinant protein was generated by stable transfection of BHK-21 cells with constructs containing either 5T4 scFv alone or 5T4scFv-Hgl (FIG. 13A & C respectively) fusion under the control of the CMV immediate/early promoter. FIG. 16 shows FACS analysis of mouse A9 5T4 cells. The cells were incubated with cell supernatent from BHK-21 cells expressing either scFv alone or scFv-HG1, followed by goat anti-human IgG—FITC labelled antibody. As can be seen the scFv-HG1 is able to bind the 5T4 expressing cells and can be detected with the goat anti-human IgG—FITC labelled antibody. FIG. 16b shows that this is due to the presence of 5T4 at the cell surface since no binding is observed with A9 cells that express the neomycin resistance marker, but no h5T4.

The same supernatents were used in an antibody dependent cell-mediated cytotoxicity (ADCC) assay which demonstrated that the scFv-Hγ1 fusion protein is able to direct lysis of A9 5T4 cells. The A9 5T4 and neo cell lines were used in a chromium release assay. After labelling with $^{51}$Cr, cells were incubated with either no protein the scFv alone or the scFv-Hγ1 fusion construct. Freshly isolated peripheral blood lymphocytes were added and incubated for 4 hours. An aliquot of supernatant was taken for scintillation counting.

% lysis was calculated as:

$$\frac{\text{Test Release} - \text{Spontaneous Release}}{\text{Maximum Release} - \text{Spontaneous Release}} \times 100$$

Figure 17:
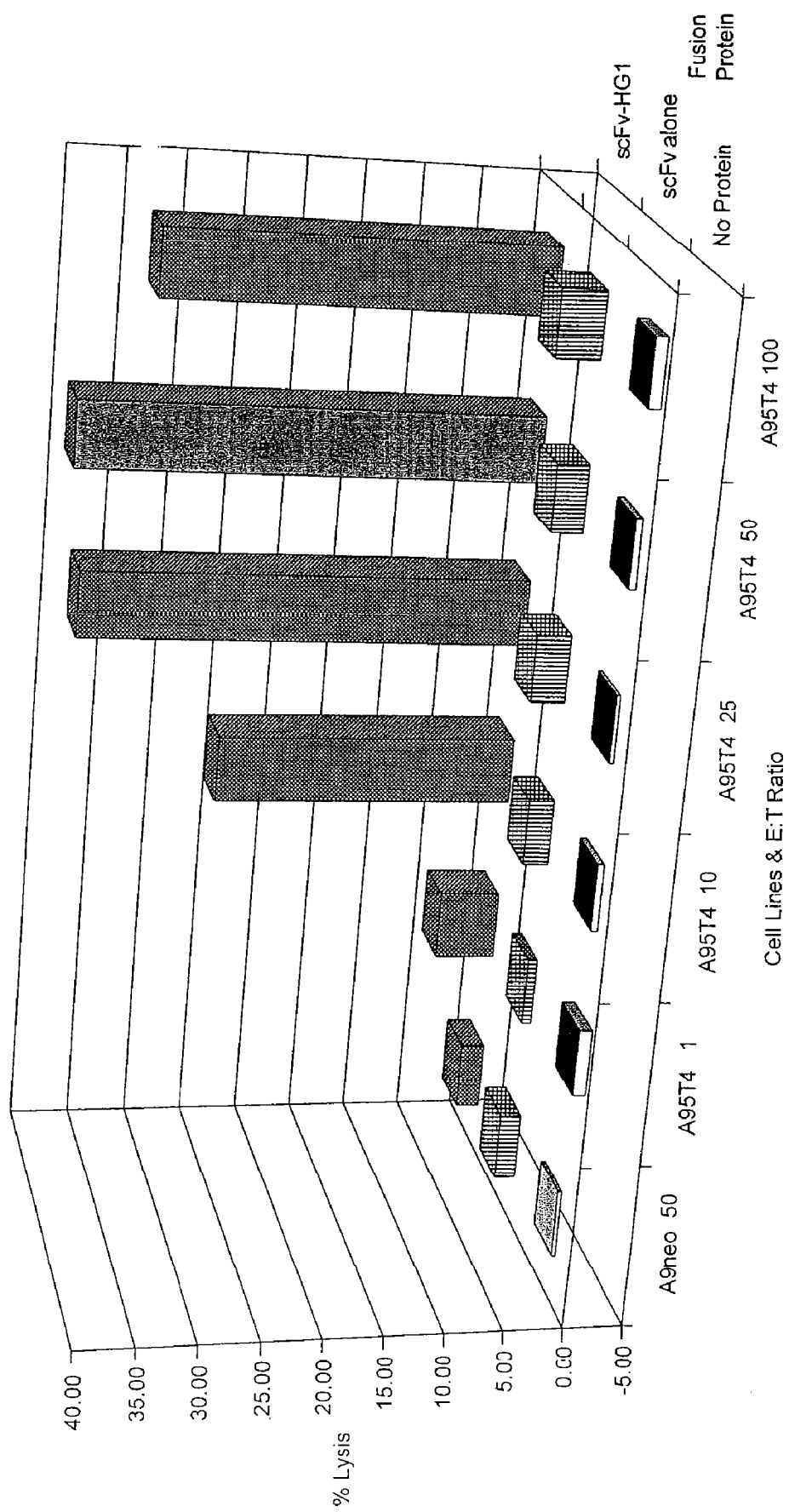

Up to ~40% lysis was obtained with increasing effector:target ratio when compared to the scFv alone. The 5T4 negative cell line showed no increased lysis (FIG. 17).

Example 14

Analysis of Efficacy in Animal Models

Human tumour—derived cell lines and tissues are cultured in vivo in genetically immunodeficient, "nude" mice according to well established techniques (see for example Strobel et al. 1997 Cancer Res. 57: 1228-1232; McLeod et al. 1997 Pancreas 14: 237-248). Syngeneic mouse models, in which a syngeneic tumour line is introduced into an immunocompetent mouse strain may also be used. These serve as suitable animal models for evaluating gene delivery systems of the invention. Vectors or engineered cells are administered systemically or directly into the tumour and tumour growth is monitored in treated and untreated animals. This system is used to define the effective dose range of the treatments of the invention and the most appropriate route of administration.

ScFv Fusion Protein In vivo Anti Tumour Efficacy Data

The purpose of the study was to test the efficacy of a series of single chain antibody fusion proteins.

Murine mouse models, based on CT26, a chemically induced adenocarcinoma of BALB/c origin (Brittain et al., (1980) Cancer Res. 40:179-184), and on B16, a melanoma line derived from C57 B6 mice. Both the CT26 line and B16 are stably transformed to express human and murine 5T4. Mice are injected I.V. (to induce lung nodules, CT26) or subcutaneously (CT26 and B16) to make single mass subcutaneous tumours.

Experimental Design

CT26 cells expressing human 5T4 (CT26-h5T4) and CT26-neo

Cells were pre-incubated with:

PBS, LScFv-1, LScFv-2, B7-ScFv, ScFv-Ig

LScFv-1 and 2 were expressed in a BHK cell line. LScFv-1 was purified via its Histidine tag on a Nickel column and ScFv-2 was purified using a filtration system. B7-ScFv was purified from a BHK line via a His tag and ScFv-Ig was purified via a filtration column. The concentration of each ScFv used in the experiment was defined as the amount of protein required to saturate binding of CT26-h5T4 cells in a FACS assay.

CT26-h5T4 and CT26-neo cells were pre-incubated with saturating amounts of each ScFv and incubated for 1 hour. After washing cells 5×10$^5$ cells were injected subcutaneously into the flanks of syngeneic BALB/c mice.

Tumour measurements were taken every two days and the volume calculated.

Results 14

FIG. 9: CT26-neo

There is not a significant difference between the groups studied apart from the treatment with LScFv-l, for which there is an approximate 3-fold reduction in tumour size compared to the PBS control 36 days after tumour inoculation.

FIG. 10: CT26-h5T4

Tumours treated with all of the 5T4 ScFv constructs had a significant effect on tumour growth. Four of the five mice treated with 5T4 ScFv-1 were tumour free on day 36. On day 36 ScFv-1 treated tumour cells were >60 fold smaller than tumours treated with PBS.

Figure 11:
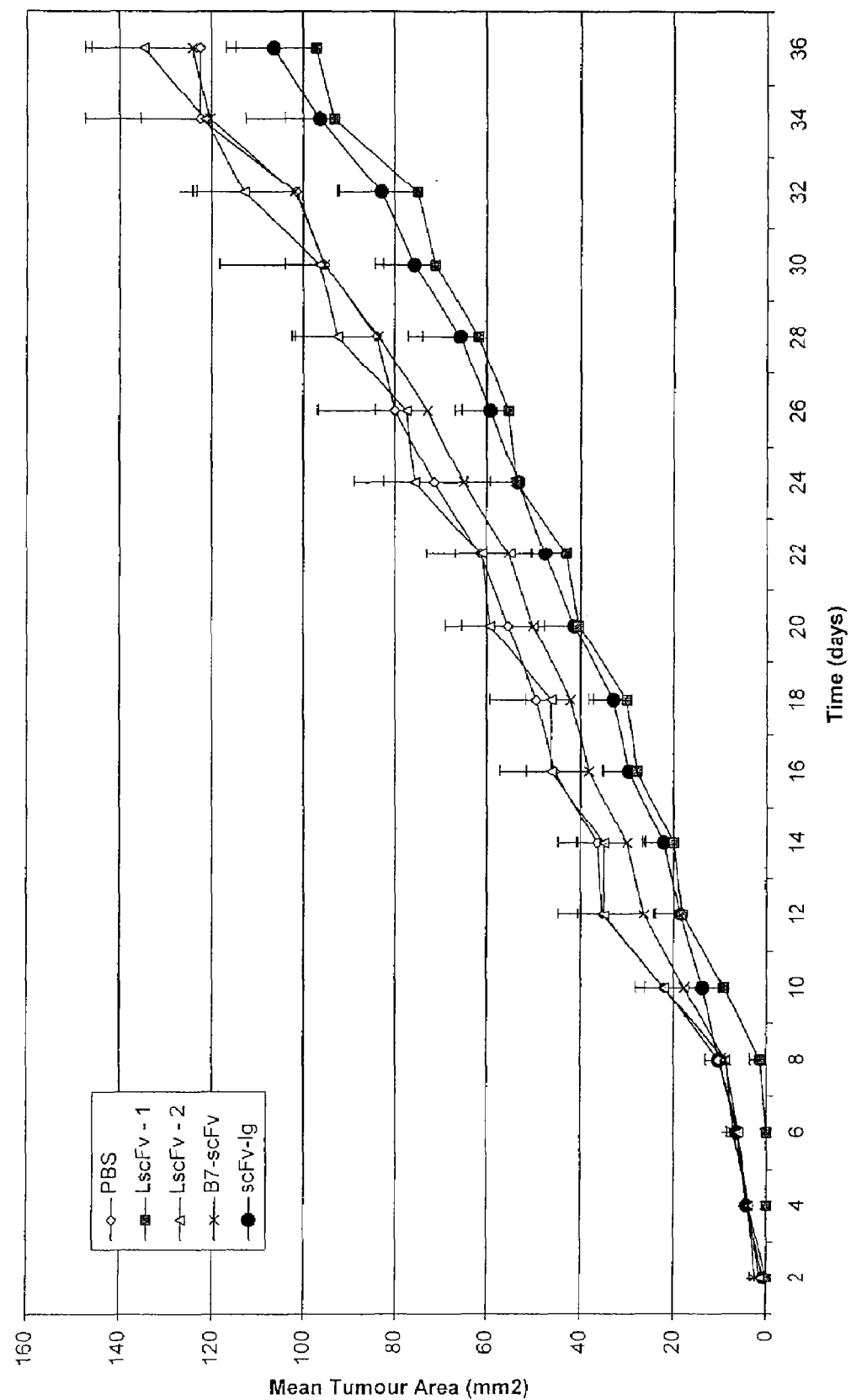
Figure 12:
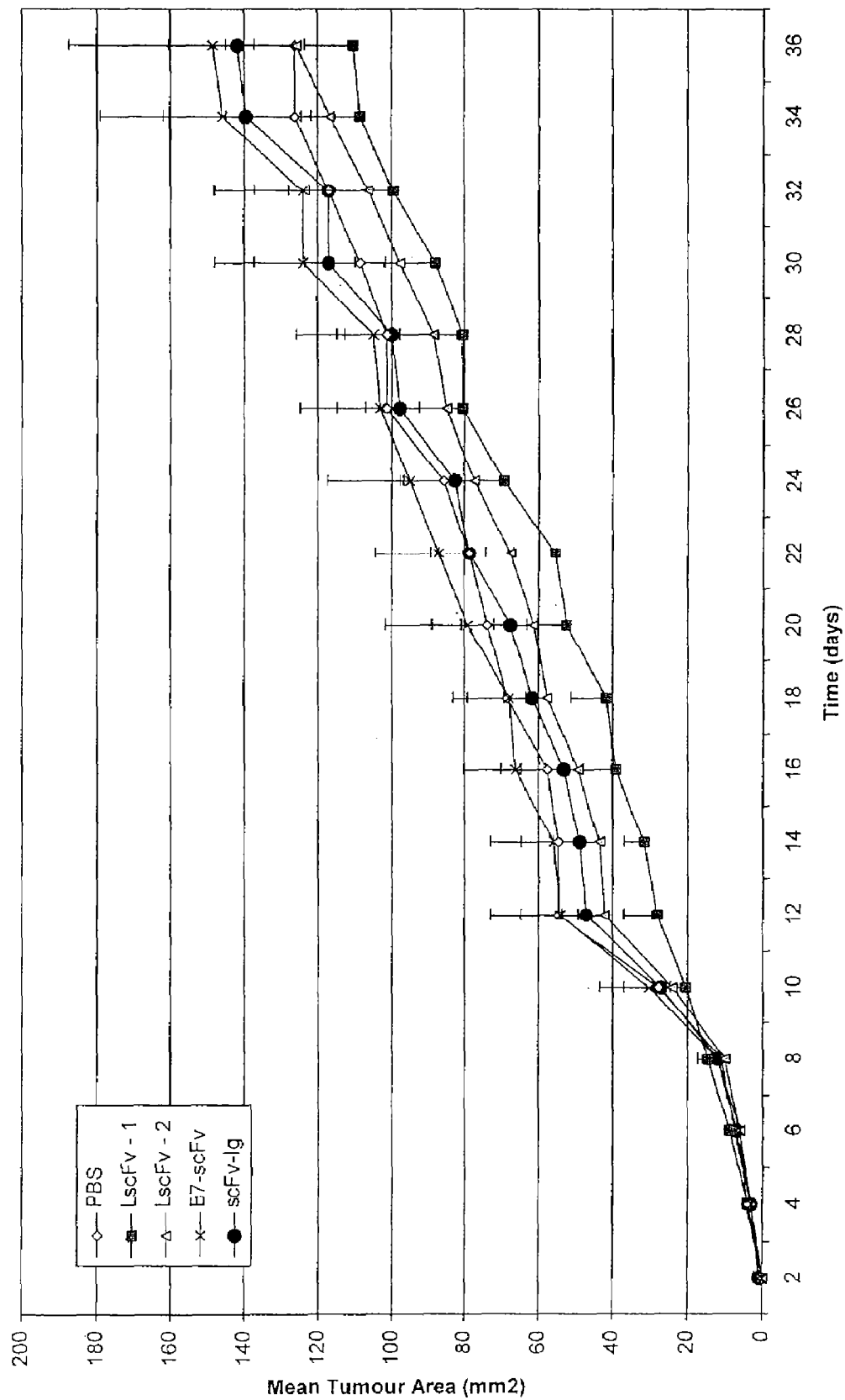

When similiar experiments were carried out using a mouse melanoma line (B16) engineered to express h5T4 a minimal anti-tumour effect was found with the ScFv constructs used (see FIGS. 11 and 12). The CT26 appear to be more sensitive to anti-tumour immune responses induced by ScFv binding than the B16 cells. In addition, B16 cells do not express murine 5T4 whereas CT26 cells have mRNA to murine 5T4.

In summary there appears to be no benefit of fusing B7 or IgG to the 5T4 specific ScFv in the CT26 and B16 murine models. In fact, we have found in our examples that the ScFv alone is more efficacious than the ScFv fusion constructs due to its higher binding affinity (as shown in BIACORE compared to B7-ScFv). Thefore these data indicate that the ScFv alone has a significant effect on tumour retardation and immune enhancing molecules fused to the ScFv may not be required to show an effect on tumour retardation in the 5T4 model.

Example 15

Production of Lentiviral Vectors Expressing the Fusion Constructs

Figure 18:
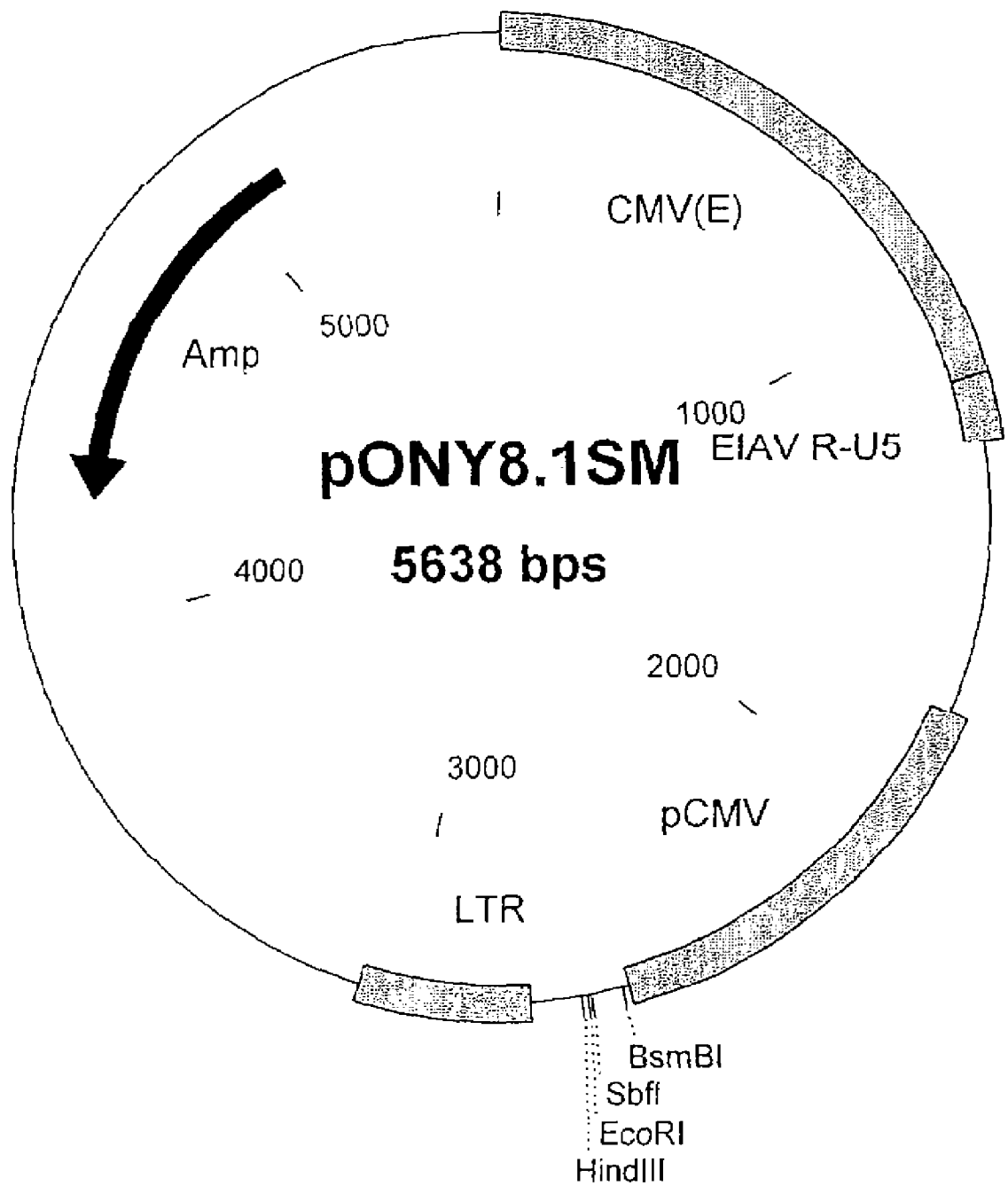

B7-5T4 scFv and L-5T4 scFv cloning into pONY 8.1SM pONY8.1SM (FIG. 18) is an EIAV vector with four unique cloning sites downstream of a CMV promoter. It is derivable from the vector shown in WO 99/32646, FIG. 1. pONY 8.1SM is the most minimal EIAV vector to date in terms of EIAV sequence that it contains (~1.1 kb) and EIAV proteins it expresses (none).

In order to clone B7-5T4 scFv and Leader-5T4 scFv (L-5T4 scFv) into pONY 8.1SM, the sequences are amplified by PCR from the constructs previously cloned into pBluescript II (see Examples 8 and 10), to incorporate an Sbf I site at the 5' end of the gene and an EcoRI site after the termination codon, using the primers shown below. The products are then directly ligated to pONY 8.1SM, previously digested with the same enzymes.

For B7-5T4 scFv the primers are as follows:
Primer 1. B7-Sbf (SEQ ID NO:31)
ATCG<u>CCTGCAGG</u> *CCACATG* GCTTGCAATTGTCAG Sbf I site=underlined
Kozak sequence=bold and italics with the ATG start codon underlined.
2. 5T4sc-RI (SEQ ID NO:32)
GCGC<u>GAATTC</u> *TTA*CCGTTTGATTTCCAGCTTGGT Eco RI site=underlined
TAA stop codon=bold and italics
The resultant product is then cloned into pONY 8.1 SM to produce the fusion protein construct shown in FIG. 19a.

Figure 9:
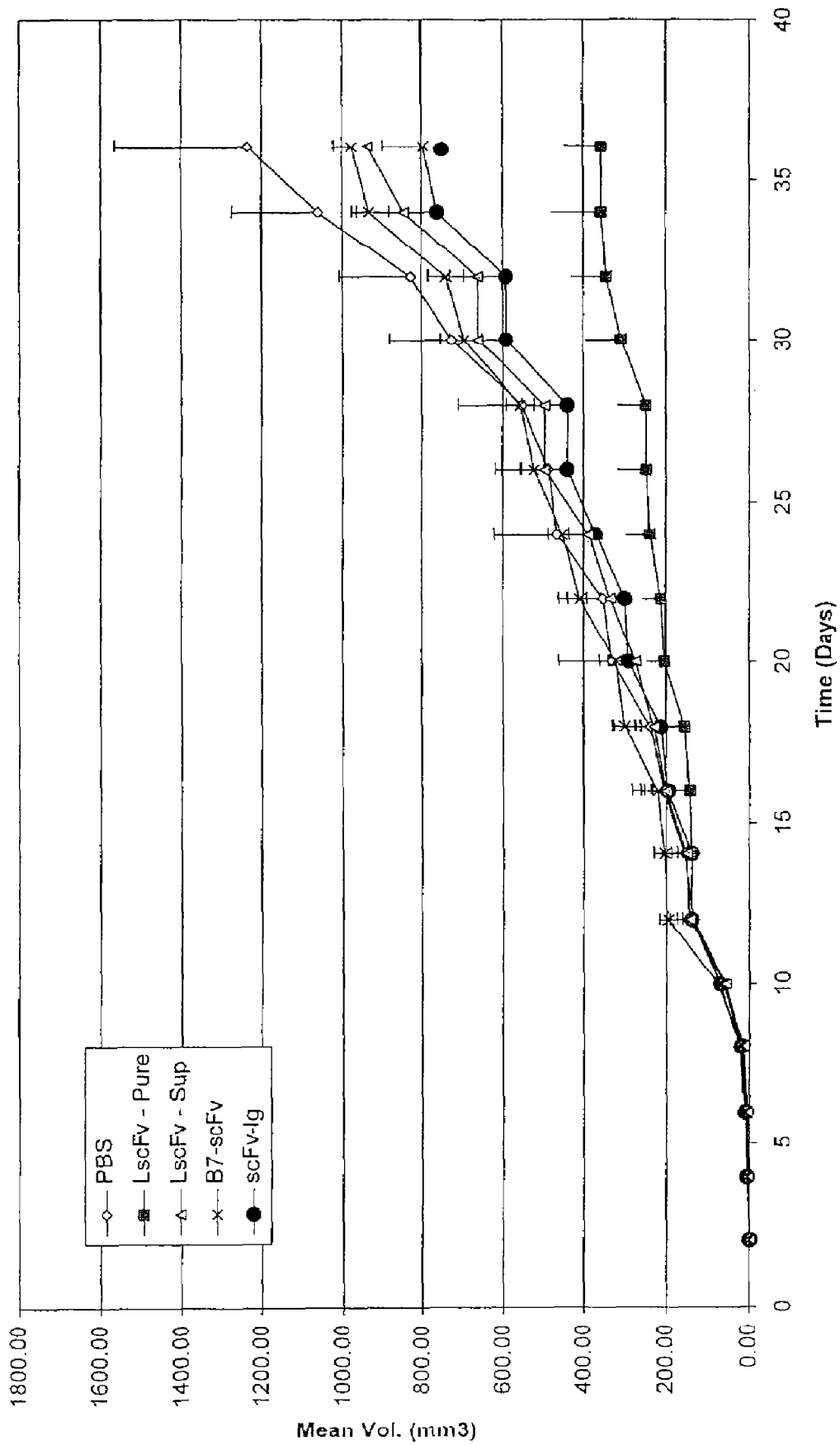
Figure 10:
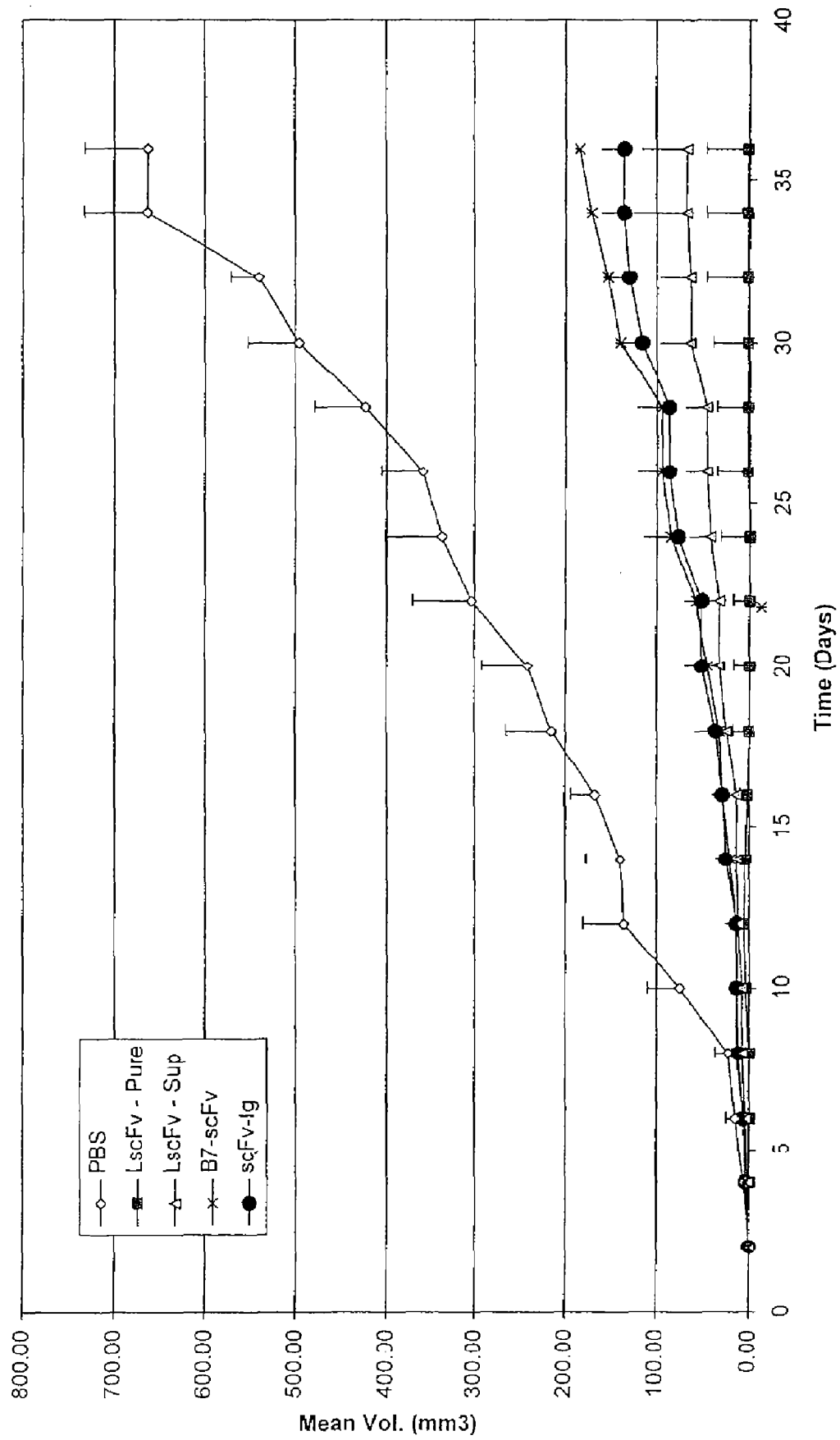

For L-5T4 scFv the primers are as follows:
Primer 1. L-Sbf (SEQ ID NO:33)
ATCG<u>CCTGCAGG</u> *CCACATG* GGATGGAGCTGTAT Sbf I site=underlined
Kozak sequence=bold and italics, with the ATG start codon underlined.
Primer 2. 5T4sc-RI (SEQ ID NO:34)
GCGC<u>GAATTC</u> *TTA*CCGTTTGATTTCCAGCTTGGT Eco RI site=underlined
TAA stop codon=bold and italics
The resultant product is then cloned into pONY 8.1 SM to produce the construct shown in FIG. 9b.

Assembly and Cloning of scFv Specific for IL-5

The anti-IL-5 scFv is assembled by RT-PCR using material prepared from a hybridoma line such as the one expressing the humanised Mab to IL-5, SB 240563 (Leckie, M J, Am. J. Respir. Crit. Care Med. 159, A624 1999). Techniques are similar to that described by Clackson et al (Genetically engineered monoclonal antibodies. Br J Rheumatol. 1991;30 Suppl 2:36-9). Briefly, Total RNA is prepared from SB 240563 cells. First strand synthesis is performed using MMLV reverse transcriptase using oligo dT primer. Template cDNAs are amplified by PCR with $V_H$ and $V_L$ gene specific primer pairs that include restriction enzyme sites, such as those shown below, to allow cloning into pKLink, a pBluescript II SK (PBSII) plasmid that contains a flexible linker sequence, $(Gly_4Ser)_3$ (FIG. 20) This forms the single chain antibody cDNA (FIG. 19). A double stranded oligonucleotide encoding a translation initiation, Kozak sequence and the human Ig kappa light chain signal peptide for secretion, similar to that described in the construction of the scFv to 5T4 (see Example 10), is then cloned upstream of the scFv (FIG. 21).

Figure 22:
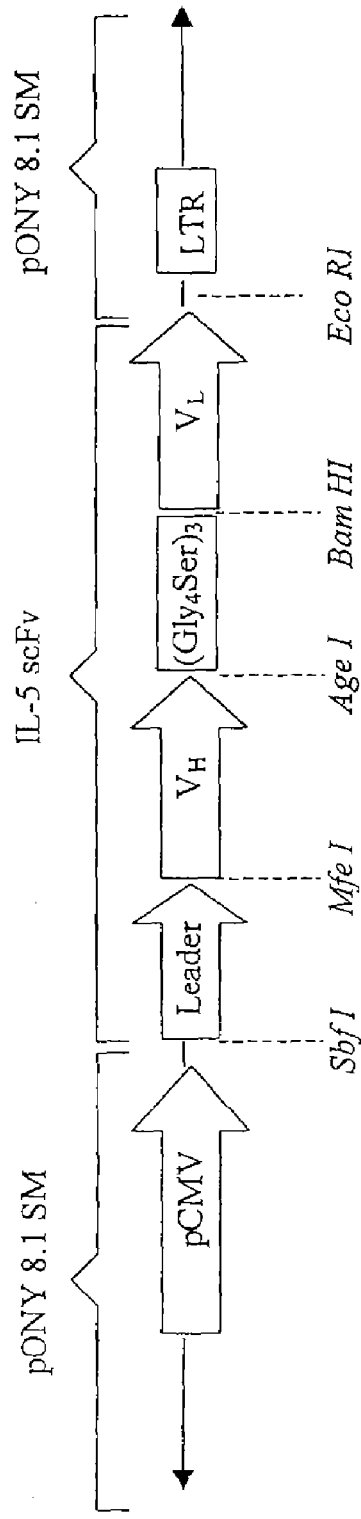

The whole construct is then excised with Sbf I and Eco RI and cloned into pONY 8.1 SM (FIG. 22).

Assembly and Cloning of scFv Specific for the Envelope Protein gp120 of HIV

The anti-HIV scFv is assembled by RT-PCR using material prepared from a hybridoma line expressing a mAb to the envelope protein gp120 of HIV, such as mAb 110.3 (Conelly et al, Virology 295: 554-557, 1994.). Alternatively guided selection is used to make a humanised antibody (see Beiboer S H et al, *J Mol Biol,*2000; 296:833-849) from which the scFv is then derived. Techniques are similar to that described by Clackson et al (Genetically engineered monoclonal antibodies. Br J Rheumatol. 1991;30 Suppl 2:36-9). Briefly, Total RNA is prepared from the hybridoma cells. First strand synthesis is performed using MMLV reverse transcriptase using oligo dT primer. Template cDNAs are amplified by PCR with $V_H$ and $V_L$ gene specific primer pairs that include restriction enzyme sites, such as those shown below, to allow cloning into pKLink, a pBluescript II SK (pBSII) plasmid that contains a flexible linker sequence, $(Gly_4Ser)_3$ (FIG. 20) This forms the single chain antibody cDNA (FIG. 21). A double stranded oligonucleotide encoding a translation initiation, Kozak sequence and the human Ig kappa light chain signal peptide for secretion, similar to that described in the construction of the scFv to 5T4 (see Example 10), is then cloned upstream of the scFv (FIG. 19).

Figure 23:
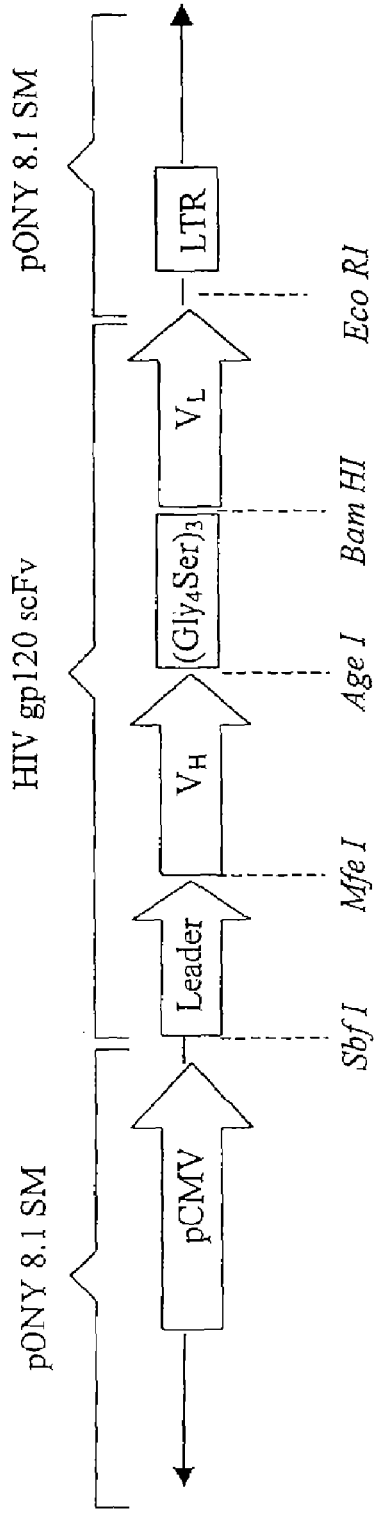

The whole construct is then excised with Sbf I and Eco RI and cloned into pONY 8.1SM (FIG. 18) to produce the construct shown in FIG. 23.

Example 16

Production of Adenoviral Vectors Expressing the Fusion Constructs

Production of Recombinat Adenovirus Expressing 5T4scFv Fusion Constructs, IL-5 scFv and ⁻HIV gp120 scFv.

B7-5T4 scFv and L-5T4 scFv cloning into pAdApt

An adenovirus transfer vector (pAdApt; see FIG. 24) with eight unique cloning sites downstream of a CMV promoter is available from Crucell, Leiden, Netherlands.

In order to clone B7-5T4 scFv and Leader-5T4 scFv (L-5T4 scFv) into pAdApt the sequences are excised from the constructs previously cloned into pBluescript II (see examples 8 and 10) and ligated into the vector as follows:

For B7-5T4 scFv:—

The B7-scFv is digested with Xba I, filled in to give a blunt end then digested with Eco RI. This fragment is then ligated to the pAdApt vector previously digested with Hpa I and Eco RI (FIG. 25A).

For L-5T4 scFv:—

The L-5T4 scFv is excised with Xho I, filled in to give blunt ends and then ligated to the pAdApt vector previously digested with Hpa I. Subsequent clones are then checked for the correct orientation of the L-5T4 scFv insert (FIG. 25B).

Cloning of scFv Specific for IL-5 into pAdApt

The L-scFv cloned into pBSII (see Example 13) is digested with Xba I, filled in to give a blunt end and then digested with Eco RI. The pAdApt vector is digested with Hind III filled in to give a blunt end and then digested Eco RI. The two molecules are then ligated to give a recombinant transfer vector resembling FIG. 25B above (with the exception that the Eco RI restriction site is at the 3' end of the fusion construct, the 5' end of the gene abutting the filled in Hind III site).

Cloning of scFv Specific for the Envelope Protein gp120 of HIV

The L-scFv cloned into pBSII (see Example 13) is digested with Xba I, filled in to give a blunt end and then digested with Eco RI. The pAdApt vector is digested with Hind III filled in to give a blunt end and then digested Eco RI. The two molecules are then ligated to give a recombinant transfer vector resembling FIG. 25B above (with the exception that the Eco RI restriction site is at the 3' end of the fusion construct, the 5' end of the gene abutting the filled in Hind III site).

Production of Recombinant Adenovirus Expressing the scFv Fusion Constructs

To produce recombinant adenovirus expressing the scFv fusion constructs, PerC6 cells are transfected with equimolar amounts of the recombinant transfer vector containing the fusion construct and an adenovirus Genome vector (AdEasy from Quantum Apligene, Harefield UK). Recombinant virus is then harvested as described in the Crucell protocol.

SUMMARY

The present invention therefore provides antibodies capable of recognising a disease associated cell surface marker (DAM). These antibodies may be used in the diagnosis and treatment of diseases associated with a DAM.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be covered by the present invention.

SEQUENCE LISTING PART OF THE DESCRIPTION

SEQ ID NO. 1 and SEQ ID No 5
See FIG. 1 (5T4ScFv. 1)
SEQ ID NO. 3 and SEQ ID No 7
See FIG. 2 (B7-1. 5T4ScFv. 1)
SEQ ID NO. 4 and SEQ ID No 8
See FIG. 6 (5T4ScFv. 1-IgG)
SEQ ID NO. 9 and SEQ ID No 10
See FIG. 4 (B7-2.5T4 1)
SEQ ID No 11
FIG. 5 (B7 link ScFv)
SEQ ID NO.12
FIG. 7 (ScFv-IgE)
SEQ ID NO. 13
FIG. 8 (B7-EGF)
SEQ ID NO. 14 and 15
FIG. 26 (canine 5T4 sequence)

---

The invention claimed is:

1. An isolated nucleic acid molecule comprising the nucleotide sequence represented by SEQ ID No: 5 or a fragment thereof, wherein the nucleotide sequence encodes an ScFv antibody (ScFv Ab) that binds to 5T4 antigen.

2. An isolated nucleic acid molecule that comprises a nucleotide sequence that is capable of hybridising under stringent conditions that include washing at 65° C. in 0.1×SSC to a full complement of a polynucleotide comprising SEQ ID NO: 5; wherein the nucleotide sequence encodes a ScFv antibody that binds to 5T4 antigen.

3. The isolated nucleic acid molecule nucleotide according to claim 2 wherein the nucleotide sequence is operably linked to a promoter.

4. An isolated construct, vector, plasmid, or host cell comprising the nucleic acid molecule according to claim 2.

5. An isolated construct, vector, plasmid, or host cell comprising the nucleic acid molecule according to claim 1.

6. The nucleic acid molecule according to claim 1 wherein the nucleotide sequence is operably linked to a promoter.

7. An isolated construct, vector, plasmid, or host cell comprising the nucleic acid molecule according to claim 6.

8. A process for preparing an ScFv antibody (ScFv Ab) capable of recognizing 5T4 antigen, said process comprising expressing the nucleic acid molecule of claim 1 in a cell.

9. The process of claim 8, wherein said nucleic acid molecule is in a construct, vector or plasmid.

10. An isolated nucleic acid molecule encoding an ScFv antibody (ScFv Ab) comprising a nucleotide sequence represented by SEQ ID No: 1 or a fragment thereof, wherein the ScFv Ab binds to 5T4 antigen.

11. An isolated construct, vector, plasmid, or host cell comprising the nucleic acid molecule according to claim 10.

12. The nucleic acid molecule according to claim 10 wherein the nucleotide sequence is operably linked to a promoter.

13. An isolated construct, vector, plasmid, or host cell comprising the nucleic acid molecule according to claim 12.

14. A process for preparing an ScFv antibody (ScFv Ab) capable of recognizing 5T4 antigen, said process comprising expressing the nucleic acid molecule of claim 10 in a cell.

15. The process of claim 14, wherein said nucleic acid molecule is in a construct, vector or plasmid.

16. An isolated nucleic acid molecule that comprises a nucleotide sequence having at least 95% identity to the nucleotide sequence of SEQ ID NO: 5 or a fragment thereof, wherein the nucleic acid molecule encodes an ScFv antibody (ScFv Ab) that binds to 5T4 antigen.

17. An isolated nucleic acid molecule that comprises a nucleotide sequence encoding an ScFv antibody (ScFv Ab) comprising a sequence having at least 95% identity to the sequence of SEQ ID NO: 1 or a fragment thereof, wherein the ScFv Ab binds to 5T4 antigen.

18. The process according to claim 8, further comprising purifying the ScFv antibody.

19. The process according to claim 14, further comprising purifying the ScFv antibody.

20. A process for preparing an ScFv antibody (ScFv Ab) capable of recognizing 5T4 antigen, said process comprising expressing the nucleic acid molecule of claim 2 in a cell.

21. The process according to claim 20, further comprising purifying the ScFv antibody.

22. A process for preparing an ScFv antibody (ScFv Ab) capable of recognizing 5T4 antigen, said process comprising expressing the nucleic acid molecule of claim 16 in a cell.

23. The process according to claim 22, further comprising purifying the ScFv antibody.

24. A process for preparing an ScFv antibody (ScFv Ab) capable of recognizing 5T4 antigen, said process comprising expressing the nucleic acid molecule of claim 17 in a cell.

25. The process according to claim 24, further comprising purifying the ScFv antibody.

* * * * *

SEQUENCE LISTING

```
<160> NUMBER OF SEQ ID NOS: 37

<210> SEQ ID NO 1
<211> LENGTH: 243
<212> TYPE: PRT
<213> ORGANISM: Artificial Sequence
<220> FEATURE:
<223> OTHER INFORMATION: sequence of the mature secreted protein

<400> SEQUENCE: 1

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30
```

```
Tyr Met His Trp Val Lys Gln Ser His Gly Lys Ser Leu Glu Trp Ile
         35                  40                  45
Gly Arg Ile Asn Pro Asn Asn Gly Val Thr Leu Tyr Asn Gln Lys Phe
     50                  55                  60
Lys Asp Lys Ala Ile Leu Thr Val Asp Lys Ser Ser Thr Thr Ala Tyr
 65                  70                  75                  80
Met Glu Leu Arg Ser Leu Thr Ser Glu Asp Ser Ala Val Tyr Tyr Cys
                 85                  90                  95
Ala Arg Ser Thr Met Ile Thr Asn Tyr Val Met Asp Tyr Trp Gly Gln
             100                 105                 110
Val Thr Ser Val Thr Val Ser Ser Gly Gly Gly Ser Gly Gly Gly
         115                 120                 125
Gly Thr Gly Gly Gly Gly Ser Ser Ile Val Met Thr Gln Thr Pro Thr
     130                 135                 140
Phe Leu Leu Val Ser Ala Gly Asp Arg Val Thr Ile Thr Cys Lys Ala
145                 150                 155                 160
Ser Gln Ser Val Ser Asn Asp Val Ala Trp Tyr Gln Gln Lys Pro Gly
                 165                 170                 175
Gln Ser Pro Thr Leu Leu Ile Ser Tyr Thr Ser Ser Arg Tyr Ala Gly
             180                 185                 190
Val Pro Asp Arg Phe Ile Gly Ser Gly Tyr Gly Thr Asp Phe Thr Phe
         195                 200                 205
Thr Ile Ser Thr Leu Gln Ala Glu Asp Leu Ala Val Tyr Phe Cys Gln
     210                 215                 220
Gln Asp Tyr Asn Ser Pro Pro Thr Phe Gly Gly Gly Thr Lys Leu Glu
225                 230                 235                 240
Ile Lys Arg

<210> SEQ ID NO 2
<211> LENGTH: 68
<212> TYPE: DNA
<213> ORGANISM: Artificial Sequence
<220> FEATURE:
<223> OTHER INFORMATION: Cassette 1- Translation initiation signal and
      signal peptide

<400> SEQUENCE: 2
aagcttccac catgggatgg agctgtatca tcctcttctt ggtagcaaca gctacaggtg    60
tccactcc                                                             68

<210> SEQ ID NO 3
<211> LENGTH: 488
<212> TYPE: PRT
<213> ORGANISM: Artificial Sequence
<220> FEATURE:
<223> OTHER INFORMATION: deduced amino acid sequence for the B7-1.5T4.1
      fusion protein

<400> SEQUENCE: 3

Met Gly His Thr Arg Arg Gln Gly Thr Ser Pro Ser Lys Cys Pro Tyr
 1               5                  10                  15
Leu Asn Phe Phe Gln Leu Leu Val Leu Ala Gly Leu Ser His Phe Cys
                 20                  25                  30
Ser Gly Val Ile His Val Thr Lys Glu Val Lys Glu Val Ala Thr Leu
         35                  40                  45
Ser Cys Gly His Asn Val Ser Val Glu Glu Leu Ala Gln Thr Arg Ile
     50                  55                  60
```

```
Tyr Trp Gln Lys Glu Lys Met Val Leu Thr Met Met Ser Gly Asp
 65                  70                  75                  80

Met Asn Ile Trp Pro Glu Tyr Lys Asn Arg Thr Ile Phe Asp Ile Thr
                 85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Gly Gly Gly Gly Ser Glu Val Gln Leu Gln Gln Ser Gly Pro Asp
                245                 250                 255

Leu Val Lys Pro Gly Ala Ser Val Lys Ile Ser Cys Lys Ala Ser Gly
            260                 265                 270

Tyr Ser Phe Thr Gly Tyr Tyr Met His Trp Val Lys Gln Ser His Gly
        275                 280                 285

Lys Ser Leu Glu Trp Ile Gly Arg Ile Asn Pro Asn Asn Gly Val Thr
    290                 295                 300

Leu Tyr Asn Gln Lys Phe Lys Asp Lys Ala Ile Leu Thr Val Asp Lys
305                 310                 315                 320

Ser Ser Thr Thr Ala Tyr Met Glu Leu Arg Ser Leu Thr Ser Glu Asp
                325                 330                 335

Ser Ala Val Tyr Tyr Cys Ala Arg Ser Thr Met Ile Thr Asn Tyr Val
            340                 345                 350

Met Asp Tyr Trp Gly Gln Val Thr Ser Val Thr Val Ser Ser Gly Gly
        355                 360                 365

Gly Gly Ser Gly Gly Gly Gly Thr Gly Gly Gly Ser Ser Ile Val
    370                 375                 380

Met Thr Gln Thr Pro Thr Phe Leu Leu Val Ser Ala Gly Asp Arg Val
385                 390                 395                 400

Thr Ile Thr Cys Lys Ala Ser Gln Ser Val Ser Asn Asp Val Ala Trp
                405                 410                 415

Tyr Gln Gln Lys Pro Gly Gln Ser Pro Thr Leu Leu Ile Ser Tyr Thr
            420                 425                 430

Ser Ser Arg Tyr Ala Gly Val Pro Asp Arg Phe Ile Gly Ser Gly Tyr
        435                 440                 445

Gly Thr Asp Phe Thr Phe Thr Ile Ser Thr Leu Gln Ala Glu Asp Leu
    450                 455                 460

Ala Val Tyr Phe Cys Gln Gln Asp Tyr Asn Ser Pro Pro Thr Phe Gly
465                 470                 475                 480
```

```
Gly Gly Thr Lys Leu Glu Ile Lys
                485

<210> SEQ ID NO 4
<211> LENGTH: 592
<212> TYPE: PRT
<213> ORGANISM: Artificial Sequence
<220> FEATURE:
<223> OTHER INFORMATION: deduced amino acid sequence for the Ig-5T4
      fusion protein

<400> SEQUENCE: 4

Met Gly Trp Ser Cys Ile Ile Leu Phe Leu Val Ala Thr Ala Thr Gly
1               5                   10                  15

Val His Ser Glu Val Gln Leu Gln Gln Ser Gly Pro Asp Leu Val Lys
            20                  25                  30

Pro Gly Ala Ser Val Lys Ile Ser Cys Lys Ala Ser Gly Tyr Ser Phe
        35                  40                  45

Thr Gly Tyr Tyr Met His Trp Val Lys Gln Ser His Gly Lys Ser Leu
    50                  55                  60

Glu Trp Ile Gly Arg Ile Asn Pro Asn Asn Gly Val Thr Leu Tyr Asn
65                  70                  75                  80

Gln Lys Phe Lys Asp Lys Ala Ile Leu Thr Val Asp Lys Ser Ser Thr
                85                  90                  95

Thr Ala Tyr Met Glu Leu Arg Ser Leu Thr Ser Glu Asp Ser Ala Val
            100                 105                 110

Tyr Tyr Cys Ala Arg Ser Thr Met Ile Thr Asn Tyr Val Met Asp Tyr
        115                 120                 125

Trp Gly Gln Val Thr Ser Val Thr Val Ser Ser Gly Gly Gly Gly Ser
    130                 135                 140

Gly Gly Gly Gly Thr Gly Gly Gly Ser Ser Ile Val Met Thr Gln
145                 150                 155                 160

Thr Pro Thr Phe Leu Leu Val Ser Ala Gly Asp Arg Val Thr Ile Thr
                165                 170                 175

Cys Lys Ala Ser Gln Ser Val Ser Asn Asp Val Ala Trp Tyr Gln Gln
            180                 185                 190

Lys Pro Gly Gln Ser Pro Thr Leu Leu Ile Ser Tyr Thr Ser Ser Arg
        195                 200                 205

Tyr Ala Gly Val Pro Asp Arg Phe Ile Gly Ser Gly Tyr Gly Thr Asp
    210                 215                 220

Phe Thr Phe Thr Ile Ser Thr Leu Gln Ala Glu Asp Leu Ala Val Tyr
225                 230                 235                 240

Phe Cys Gln Gln Asp Tyr Asn Ser Pro Pro Thr Phe Gly Gly Gly Thr
                245                 250                 255

Lys Leu Glu Ile Lys Arg Ala Ser Thr Lys Gly Pro Ser Val Phe Pro
            260                 265                 270

Leu Ala Pro Ser Ser Lys Ser Thr Ser Gly Gly Thr Ala Ala Leu Gly
        275                 280                 285

Cys Leu Val Lys Asp Tyr Phe Pro Glu Pro Val Thr Val Ser Trp Asn
    290                 295                 300

Ser Gly Ala Leu Thr Ser Gly Val His Thr Phe Pro Ala Val Leu Gln
305                 310                 315                 320

Ser Ser Gly Leu Tyr Ser Leu Ser Ser Val Val Thr Val Pro Ser Ser
                325                 330                 335

Ser Leu Gly Thr Gln Thr Tyr Ile Cys Asn Val Asn His Lys Pro Ser
            340                 345                 350
```

```
Asn Thr Lys Val Asp Lys Lys Val Glu Pro Lys Ser Cys Asp Lys Thr
        355                 360                 365
His Thr Cys Pro Pro Cys Pro Ala Pro Glu Leu Leu Gly Gly Pro Ser
    370                 375                 380
Val Phe Leu Phe Pro Pro Lys Pro Lys Asp Thr Leu Met Ile Ser Arg
385                 390                 395                 400
Thr Pro Glu Val Thr Cys Val Val Val Asp Val Ser His Glu Asp Pro
                405                 410                 415
Glu Val Lys Phe Asn Trp Tyr Val Asp Gly Val Glu Val His Asn Ala
            420                 425                 430
Lys Thr Lys Pro Arg Glu Glu Gln Tyr Asn Ser Thr Tyr Arg Val Val
        435                 440                 445
Ser Val Leu Thr Val Leu His Gln Asp Trp Leu Asn Gly Lys Glu Tyr
    450                 455                 460
Lys Cys Lys Val Ser Asn Lys Ala Leu Pro Ala Pro Ile Glu Lys Thr
465                 470                 475                 480
Ile Ser Lys Ala Lys Gly Gln Pro Arg Glu Pro Gln Val Tyr Thr Leu
                485                 490                 495
Pro Pro Ser Arg Asp Glu Met Thr Lys Asn Gln Val Ser Leu Thr Cys
            500                 505                 510
Leu Val Lys Gly Phe Tyr Pro Ser Asp Ile Ala Val Glu Trp Glu Ser
        515                 520                 525
Asn Gly Gln Pro Glu Asn Asn Tyr Lys Thr Thr Pro Pro Val Leu Asp
    530                 535                 540
Ser Asp Gly Ser Phe Phe Leu Tyr Ser Lys Leu Thr Val Asp Lys Ser
545                 550                 555                 560
Arg Trp Gln Gln Gly Asn Val Phe Ser Cys Ser Val Met His Glu Ala
                565                 570                 575
Leu His Asn His Tyr Thr Gln Lys Ser Leu Ser Leu Ser Pro Gly Lys
            580                 585                 590

<210> SEQ ID NO 5
<211> LENGTH: 729
<212> TYPE: DNA
<213> ORGANISM: Artificial Sequence
<220> FEATURE:
<223> OTHER INFORMATION: DNA sequence encoding a 5T4 ScFv designated
      5T4ScFv.1

<400> SEQUENCE: 5
gaggtccagc ttcagcagtc tggacctgac ctggtgaagc ctggggcttc agtgaagata      60
tcctgcaagg cttctggtta ctcattcact ggctactaca tgcactgggt gaagcagagc     120
catggaaaga gccttgagtg gattggacgt attaatccta caatggtgt tactctctac       180 aaccagaaat tcaaggacaa ggccatatta actgtagaca gtcatccac acagcctac       240 atggagctcc gcagcctgac atctgaggac tctgcggtct attactgtgc aagatctact     300
atgattacga actatgttat ggactactgg ggtcaagtaa cctcagtcac cgtctcctca     360
ggtggtggtg ggagcggtgg tggcggcact ggcggcggcg gatctagtat tgtgatgacc     420
cagactccca cattcctgct tgtttcagca ggagacaggg ttaccataac ctgcaaggcc     480
agtcagagtg tgagtaatga tgtagdttgg taccaacaga agccagggca gtctcctaca     540
ctgctcatat cctatacatc cagtcgctac gctggagtcc ctgatcgctt cattggcagt     600
ggatatggga cggatttcac tttcaccatc agcactttgc aggctgaaga cctggcagtt     660
```

```
tatttctgtc agcaagatta taattctcct ccgacgttcg gtggaggcac caagctggaa      720
atcaaacgg                                                              729

<210> SEQ ID NO 6
<211> LENGTH: 43
<212> TYPE: DNA
<213> ORGANISM: Artificial Sequence
<220> FEATURE:
<223> OTHER INFORMATION: oligonucleotide used to construct flexible
      linker to join the ext racellular domain of B7.1 and ScFv

<400> SEQUENCE: 6
gggggtggtg ggagcggtgg tggcggcagt ggcggcggcg gaa                        43

<210> SEQ ID NO 7
<211> LENGTH: 1467
<212> TYPE: DNA
<213> ORGANISM: Artificial Sequence
<220> FEATURE:
<223> OTHER INFORMATION: DNA sequence encoding a B7-1.5T4.1 fusion
      protein

<400> SEQUENCE: 7
atgggccaca cacggaggca gggaacatca ccatccaagt gtccataccT caatttcttt      60
cagctcttgg tgctggctgg tctttctcac ttctgttcag gtgttatcca cgtgaccaag      120
gaagtgaaag aagtggcaac gctgtcctgt ggtcacaatg tttctgttga agagctggca      180
caaactcgca tctactggca aaaggagaag aaaatggtgc tgactatgat gtctggggac      240
atgaatatat ggcccgagta caagaaccgg accatctttg atatcactaa taacctctcc      300
attgtgatcc tggctctgcg cccatctgac gagggcacat acgagtgtgt tgttctgaag      360
tatgaaaaag acgctttcaa gcgggaacac ctggctgaag tgacgttatc agtcaaagct      420
gacttcccta cacctagtat atctgacttt gaaattccaa cttctaatat tagaaggata      480
atttgctcaa cctctggagg ttttccagag cctcacctct cctggttgga aaatggagaa      540
gaattaaatg ccatcaacac aacagttccc caagatcctg aaactgagct ctatgctgtt      600
agcagcaaac tggatttcaa tatgacaacc aaccacagct tcatgtgtct catcaagtat      660
ggacatttaa gagtgaatca gaccttcaac tggaatacaa ccaagcaaga gcattttcct      720
gatggaggcg ggggatccga ggtccagctt cagcagtctg gacctgacct ggtgaagcct      780
ggggcttcag tgaagatatc ctgcaaggct tctggttact cattcactgg ctactacatg      840
cactgggtga agcagagcca tggaaagagc cttgagtgga ttggacgtat taatcctaac      900
aatggtgtta ctctctacaa ccagaaattc aaggacaagg ccatattaac tgtagacaag      960
tcatccacca cagcctacat ggagctccgc agcctgacat ctgaggactc tgcggtctat     1020
tactgtgcaa gatctactat gattacgaac tatgttatgg actactgggg tcaagtaacc     1080
tcagtcaccg tctcctcagg tggtggtggg agcggtggtg gcggcactgg cggcggcgga     1140
tctagtattg tgatgaccca gactcccaca ttcctgcttg tttcagcagg agacagggtt     1200
accataacct gcaaggccag tcagagtgtg agtaatgatg tagcttggta ccaacagaag     1260
ccagggcagt ctcctacact gctcatatcc tatacatcca gtcgctacgc tggagtccct     1320
gatcgcttca ttggcagtgg atatgggacg gatttcactt tcaccatcag cacttttgcag     1380 gctgaagacc tggcagttta tttctgtcag caagattata attctcctcc gacgttcggt     1440
ggaggcacca agctggaaat caaataa                                         1467
```

<210> SEQ ID NO 8
<211> LENGTH: 1796
<212> TYPE: DNA
<213> ORGANISM: Artificial Sequence
<220> FEATURE:
<223> OTHER INFORMATION: DNA sequence encoding a Ig-5T4 fusion protein

<400> SEQUENCE: 8

```
ctcgagccac catgggatgg agctgtatca tcctcttctt ggtagcaaca gctacaggtg      60
tccactccga ggtccagctg cagcagtctg gacctgacct ggtgaagcct ggggcttcag     120
tgaagatatc ctgcaaggct tctggttact cattcactgg ctactacatg cactgggtga     180
agcagagcca tggaaagagc cttgagtgga ttggacgtat taatcctaac aatggtgtta     240
ctctctacaa ccagaaattc aaggacaagg ccatattaac tgtagacaag tcatccacca     300
cagcctacat ggagctccgc agcctgacat ctgaggactc tgcggtctat tactgtgcaa     360
gatctactat gattacgaac tatgttatgg actactgggg tcaagtaact tcagtcaccg     420
tctcttcagg tggtggtggg agcggtggtg gcggcactgg cggcggcgga tctagtattg     480
tgatgaccca gactcccaca ttcctgcttg tttcagcagg agacagggtt accataacct     540
gcaaggccag tcagagtgtg agtaatgatg tagcttggta ccaacagaag ccagggcagt     600
ctcctacact gctcatatcc tatacatcca gtcgctacgc tggagtccct gatcgcttca     660
ttggcagtgg atatgggacg gatttcactt tcaccatcag cactttgcag gctgaagacc     720
tggcagttta tttctgtcag caagattata attctcctcc gacgttcggt ggaggcacca     780
agcttgaaat caaacgggcc tccaccaagg gcccatcggt cttccccctg gcaccctcct     840
ccaagagcac ctctgggggc acagcggccc tgggctgcct ggtcaaggac tacttccccg     900
aaccggtgac ggtgtcgtgg aactcaggcg ccctgaccag cggcgtgcac accttcccgg     960
ctgtcctaca gtcctcagga ctctactccc tcagcagcgt ggtgaccgtg ccctccagca    1020
gcttgggcac ccagacctac atctgcaacg tgaatcacaa gcccagcaac accaaggtgg    1080
acaagaaagt tgagcccaaa tcttgtgaca aaactcacac atgcccaccg tgcccagcac    1140
ctgaactcct ggggggaccg tcagtcttcc tcttcccccc aaaacccaag gacaccctca    1200
tgatctcccg gacccctgag gtcacatgcg tggtggtgga cgtgagccac gaagaccctg    1260
aggtcaagtt caactggtac gtggacggcg tggaggtgca taatgccaag acaaagccgc    1320
gggaggagca gtacaacagc acgtaccgtg tggtcagcgt cctcaccgtc ctgcaccagg    1380
actggctgaa tggcaaggag tacaagtgca aggtctccaa caaagccctc ccagccccca    1440
tcgagaaaac catctccaaa gccaagggc agccccgaga accacaggtg tacaccctgc    1500
ccccatcccg ggatgagctg accaagaacc aggtcagcct gacctgcctg gtcaaaggct    1560
tctatcccag cgacatcgcc gtggagtggg agagcaatgg gcagccggag aacaactaca    1620
agaccacgcc tcccgtgctg gactccgacg gctccttctt cctctatagc aagctcaccg    1680
tggacaagag caggtggcag caggggaacg tcttctcatg ctccgtgatg catgaggctc    1740
tgcacaacca ctacacgcag aagagcctct ccctgtcccc gggtaaatga ctcgag        1796
```

<210> SEQ ID NO 9
<211> LENGTH: 738
<212> TYPE: DNA
<213> ORGANISM: Artificial Sequence
<220> FEATURE:
<223> OTHER INFORMATION: DNA sequence encoding a B7-2.5T4.1 fusion protein

<400> SEQUENCE: 9

```
atgggactga gtaacattct ctttgtgatg gccttcctgc tctctggtgc tgctcctctg    60
aagattcaag cttatttcaa tgagactgca gacctgccat gccaatttgc aaactctcaa   120
aaccaaagcc tgagtgagct agtagtattt tggcaggacc aggaaaactt ggttctgaat   180
gaggtatact taggcaaaga gaaatttgac agtgttcatt ccaagtatat gggccgcaca   240
agttttgatt cggacagttg gaccctgaga cttcacaatc ttcagatcaa ggacaagggc   300
ttgtatcaat gtatcatcca tcacaaaaag cccacaggaa tgattcgcat ccaccagatg   360
aattctgaac tgtcagtgct tgctaacttc agtcaacctg aaatagtacc aatttctaat   420
ataacagaaa atgtgtacat aaatttgacc tgctcatcta tacacggtta cccagaacct   480
aagaagatga gtgttttgct aagaaccaag aattcaacta tcgagtatga tggtattatg   540
cagaaatctc aagataatgt cacagaactg tacgacgttt ccatcagctt gtctgtttca   600
ttccctgatg ttacgagcaa tatgaccatc ttctgtattc tggaaactga caagacgcgg   660 ctttatctt cacctttctc tatagagctt gaggaccctc agcctccccc agaccacatt   720
cctggaggcg ggggatcc                                                 738
```

<210> SEQ ID NO 10
<211> LENGTH: 246
<212> TYPE: PRT
<213> ORGANISM: Artificial Sequence
<220> FEATURE:
<223> OTHER INFORMATION: deduced amino acid sequence for the B7-2.5T4.1
      fusion protein

<400> SEQUENCE: 10

```
Met Gly Leu Ser Asn Ile Leu Phe Val Met Ala Phe Leu Leu Ser Gly
1               5                   10                  15

Ala Ala Pro Leu Lys Ile Gln Ala Tyr Phe Asn Glu Thr Ala Asp Leu
            20                  25                  30

Pro Cys Gln Phe Ala Asn Ser Gln Asn Gln Ser Leu Ser Glu Leu Val
        35                  40                  45

Val Phe Trp Gln Asp Gln Glu Asn Leu Val Leu Asn Glu Val Tyr Leu
    50                  55                  60

Gly Lys Glu Lys Phe Asp Ser Val His Ser Lys Tyr Met Gly Arg Thr
65                  70                  75                  80

Ser Phe Asp Ser Asp Ser Trp Thr Leu Arg Leu His Asn Leu Gln Ile
                85                  90                  95

Lys Asp Lys Gly Leu Tyr Gln Cys Ile Ile His His Lys Lys Pro Thr
            100                 105                 110

Gly Met Ile Arg Ile His Gln Met Asn Ser Glu Leu Ser Val Leu Ala
        115                 120                 125

Asn Phe Ser Gln Pro Glu Ile Val Pro Ile Ser Asn Ile Thr Glu Asn
    130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
        195                 200                 205

Thr Ile Phe Cys Ile Leu Glu Thr Asp Lys Thr Arg Leu Leu Ser Ser
    210                 215                 220
```

Pro Phe Ser Ile Glu Leu Glu Asp Pro Gln Pro Pro Asp His Ile
225                 230                 235                 240

Pro Gly Gly Gly Gly Ser
            245

<210> SEQ ID NO 11
<211> LENGTH: 1518
<212> TYPE: DNA
<213> ORGANISM: Artificial Sequence
<220> FEATURE:
<223> OTHER INFORMATION: B7 link ScFv sequence

<400> SEQUENCE: 11

| | | | | | |
|---|---|---|---|---|---|
| atggcttgca | attgtcagtt | gatgcaggat | acaccactcc | tcaagtttcc | atgtccaagg | 60 |
| ctcattcttc | tctttgtgct | gctgattcgt | ctttcacaag | tgtcttcaga | tgttgatgaa | 120 |
| caactgtcca | gtcagtgaa | agataaggta | ttgctgcctt | gccgttacaa | ctctccgcat | 180 |
| gaagatgagt | ctgaagaccg | aatctactgg | caaaaacatg | acaaagtggt | gctgtctgtc | 240 |
| attgctggga | aactaaaagt | gtggcccgag | tataagaacc | ggactttata | tgacaacact | 300 |
| acctactctc | ttatcatcct | gggcctggtc | ctttcagacc | ggggcacata | cagctgtgtc | 360 |
| gttcaaaaga | aggaaagagg | aacgtatgaa | gttaaacact | ggctttagt | aaagttgtcc | 420 |
| atcaaagctg | acttctctac | ccccaacata | actgagtctg | aaacccatc | tgcagacact | 480 |
| aaaaggatta | cctgctttgc | ttccgggggt | ttcccaaagc | ctcgcttctc | ttggttggaa | 540 |
| aatgaagag | aattacctgg | catcaatacg | acaatttccc | aggatcctga | atctgaattg | 600 |
| tacaccatta | gtagccaact | agatttcaat | acgactcgca | accacaccat | taagtgtctc | 660 |
| attaaatatg | gagatgctca | cgtgtcagag | gacttcacct | gggaaaaacc | cccagaagac | 720 |
| cctcctgata | gcaagcccgg | gggtggtggg | agcggtggtg | gcggcagtgg | cggcggcgga | 780 |
| actagtgagg | tccagcttca | gcagtctgga | cctgacctgg | tgaagcctgg | ggcttcagtg | 840 |
| aagatatcct | gcaaggcttc | tggttactca | ttcactggct | actacatgca | ctgggtgaag | 900 |
| cagagccatg | gaaagagcct | tgagtggatt | ggacgtatta | tcctaacaa | tggtgttact | 960 |
| ctctacaacc | agaaattcaa | ggacaaggcc | atattaactg | tagacaagtc | atccaccaca | 1020 |
| gcctacatgg | agctccgcag | cctgacatct | gaggactctg | cggtctatta | ctgtgcaaga | 1080 |
| tctactatga | ttacgaacta | tgttatggac | tactggggtc | aagtaacttc | agtcaccgtc | 1140 |
| tcttcaggtg | gtggtgggag | cggtggtggc | ggcactggcg | gcggcggatc | tagtattgtg | 1200 |
| atgacccaga | ctcccacatt | cctgcttgtt | tcagcaggag | acagggttac | cataacctgc | 1260 |
| aaggccagtc | agagtgtgag | taatgatgta | gcttggtacc | aacagaagcc | agggcagtct | 1320 |
| cctacactgc | tcatatccta | tacatccagt | cgctacgctg | gagtccctga | tcgcttcatt | 1380 |
| ggcagtggat | atgggacgga | tttcactttc | accatcagca | ctttgcaggc | tgaagacctg | 1440 |
| gcagtttatt | tctgtcagca | agattataat | tctcctccga | cgttcggtgg | aggcaccaag | 1500 |
| ctggaaatca | aacggtaa | | | | | 1518 |

<210> SEQ ID NO 12
<211> LENGTH: 2090
<212> TYPE: DNA
<213> ORGANISM: Artificial Sequence
<220> FEATURE:
<223> OTHER INFORMATION: ScFv-IgE

<400> SEQUENCE: 12

-continued

```
ctcgagccac catgggatgg agctgtatca tcctcttctt ggtagcaaca gctacaggtg      60
tccactccga ggtccagctg cagcagtctg gacctgacct ggtgaagcct ggggcttcag     120
tgaagatatc ctgcaaggct tctggttact cattcactgg ctactacatg cactgggtga     180
agcagagcca tggaaagagc cttgagtgga ttggacgtat taatcctaac aatggtgtta     240
ctctctacaa ccagaaattc aaggacaagg ccatattaac tgtagacaag tcatccacca     300
cagcctacat ggagctccgc agcctgacat ctgaggactc tgcggtctat tactgtgcaa     360
gatctactat gattacgaac tatgttatgg actactgggg tcaagtaact tcagtcaccg     420
tctcttcagg tggtggtggg agcggtggtg gcggcactgg cggcggcgga tctagtattg     480
tgatgaccca gactcccaca ttcctgcttg tttcagcagg agacagggtt accataacct     540
gcaaggccag tcagagtgtg agtaatgatg tagcttggta ccaacagaag ccagggcagt     600
ctcctacact gctcatatcc tatacatcca gtcgctacgc tggagtccct gatcgcttca     660
ttggcagtgg atatgggacg gatttcactt tcaccatcag cactttgcag gctgaagacc     720
tggcagttta tttctgtcag caagattata attctcctcc gacgttcggt ggaggcacca     780
agcttgaaat caaacgggcc tccacacaga gcccatccgt cttcccttg acccgctgct     840
gcaaaaacat tccctccaat gccacctccg tgactctggg ctgcctggcc acgggctact     900
tcccggagcc ggtgatggtg acctgggaca caggctccct caacgggaca actatgacct     960
taccagccac caccctcacg ctctctggtc actatgccac catcagcttg ctgaccgtct    1020
cgggtgcgtg ggccaagcag atgttcacct gccgtgtggc acacactcca tcgtccacag    1080
actgggtcga caacaaaacc ttcagcgtct gctccaggga cttcacccg cccaccgtga    1140
agatcttaca gtcgtcctgc gacggcggcg ggcacttccc cccgaccatc cagctcctgt    1200
gcctcgtctc tgggtacacc ccagggacta tcaacatcac ctggctggag gacgggcagg    1260
tcatggacgt ggacttgtcc accgcctcta ccacgcagga gggtgagctg gcctccacac    1320
aaagcgagct caccctcagc cagaagcact ggctgtcaga ccgcacctac acctgccagg    1380
tcacctatca aggtcacacc tttgaggaca gcaccaagaa gtgtgcagat tccaacccga    1440
gaggggtgag cgcctaccta agccggccca gcccgttcga cctgttcatc cgcaagtcgc    1500
ccacgatcac ctgtctggtg gtggacctgg cacccagcaa ggggaccgtg aacctgacct    1560
ggtcccgggc cagtgggaag cctgtgaacc actccaccag aaaggaggag aagcagcgca    1620
atggcacgtt aaccgtcacg tccacccctgc cggtgggcac ccgagactgg atcgaggggg    1680
agacctacca gtgcagggtg acccacccccc acctgcccag ggccctcatg cggtccacga    1740
ccaagaccag cggcccgcgt gctgcccegg aagtctatgc gtttgcgacg ccggagtggc    1800
cggggagccg ggacaagcgc accctcgcct gcctgatcca gaacttcatg cctgaggaca    1860
tctcggtgca gtggctgcac aacgaggtgc agctcccgga cgcccggcac agcacgacgc    1920
agccccgcaa gaccaagggc tccggcttct tcgtcttcag ccgcctggag gtgaccaggg    1980
ccgaatggga gcagaaagat gagttcatct gccgtgcagt ccatgaggca gcgagcccct    2040
cacagaccgt ccagcgagcg gtgtctgtaa atcccggtaa atgagagctc                2090
```

<210> SEQ ID NO 13
<211> LENGTH: 945
<212> TYPE: DNA
<213> ORGANISM: Artificial Sequence
<220> FEATURE:
<223> OTHER INFORMATION: B7-EGF

<400> SEQUENCE: 13

```
atggcttgca attgtcagtt gatgcaggat acaccactcc tcaagtttcc atgtccaagg      60
ctcattcttc tctttgtgct gctgattcgt ctttcacaag tgtcttcaga tgttgatgaa     120
caactgtcca agtcagtgaa agataaggta ttgctgcctt ccgttacaa  ctctccgcat     180 gaagatgagt ctgaagaccg aatctactgg caaaaacatg acaaagtggt gctgtctgtc     240
attgctggga aactaaaagt gtggcccgag tataagaacc ggactttata tgacaacact     300
acctactctc ttatcatcct gggcctggtc ctttcagacc ggggcacata cagctgtgtc     360
gttcaaaaga aggaaagagg aacgtatgaa gttaaacact tggctttagt aaagttgtcc     420
atcaaagctg acttctctac ccccaacata actgagtctg aaacccatc  tgcagacact     480 aaaaggatta cctgctttgc ttccgggggt ttcccaaagc tcgcttctc  ttggttggaa     540 aatggaagag aattacctgg catcaatacg acaatttccc aggatcctga atctgaattg     600
tacaccatta gtagccaact agatttcaat acgactcgca accacaccat taagtgtctc     660
attaaatatg gagatgctca cgtgtcagag gacttcacct gggaaaaacc cccagaagac     720
cctcctgata gcaagcccgg gggtggtggg agcggtggtg gcggcagtgg cggcggcgga     780
actagtaata gtgactctga atgtcccctg tcccacgatg ggtactgcct ccatgatggt     840
gtgtgcatgt atattgaagc attggacaag tatgcatgca actgtgttgt tggctacatc     900
ggggagcgat gtcagtaccg agacctgaag tggtgggaac tgcgc                    945

<210> SEQ ID NO 14
<211> LENGTH: 1263
<212> TYPE: DNA
<213> ORGANISM: Artificial Sequence
<220> FEATURE:
<223> OTHER INFORMATION: canine 5T4 polypeptide having the amino acid
      sequence

<400> SEQUENCE: 14
atgcctgggg ggtgctcccg ggccccgcc  gccggggacg ggcggttgcg gctggcgcgg      60
ctggcgctgg tgctcctggg ctgggtctcc tcgtcctcgc tcacctcctg gcgcccctcc     120
gccgccgcct ccacgtcgcc gccggcctcc gcggcgtccg cccc gccccc gctgccgggc     180 cagtgccccc agccttgcga gtgctcggag gcggcgcgca cggtcaagtg cgttaaccgc     240
aacctgaccg aggtgcccgc ggacctgccc ccctacgtgc gcaacctctt cctcacgggc     300
aaccagctgg cggtgctgcc ccccggcgcc ttcgcccgcc ggccgccgct ggccgagctg     360
gccgcgctca acctgagcgg cagcagcctg cgggaggtgt gcgccggcgc cttcgagcac     420
ctgcccagcc tgcgccagct cgacctcagc cacaacccgc tgggcaacct cagcgccttc     480
gccttcgcgg gcagcgacgc cagccgctcg ggccccagcc cctggtgga  gctgatgctg     540 aaccacatcg tgccccccga cgaccggcgg cagaaccgga gcttcgaggg catggtggcg     600
gctgccctcc gagcgggccg cgcgcttcgc gggctgcagt gcctggagct ggccggcaac     660
cgcttcctct acttgcctcg cgacgtcctg gcccagctac ccggcctccg gcacctggac     720
ctgcgcaaca actccctggt gagcctcacc tacgtgtcct ccgcaacct  gacgcacttg     780 gagagcctcc acctggagga caacgccctc aaggtccttt acaacgccac cctggcggag     840
ctgcagagcc tgccccacgt ccgggtcttc tggacaaca  ccc ctgggt ctgcgattgt     900 cacatggcag acatggtggc ctggctcaag agacagagg  tggtgccggg caaagccggg     960
ctcacctgtg cattcccgga gaaaatgagg aatcgggccc tcttggaact caacagctcc    1020
cacctggact gtgaccctat cctccctcca tccctgcaga cttcttatgt cttcctaggt    1080
```

```
attgtcttag ccctgatagg cgccatcttc ctactggttt tgtatttgaa ccgcaagggg    1140
ataaagaagt ggatgcataa catcagagat gcctgcaggg atcacatgga agggtatcac    1200
tacagatacg aaatcaatgc agaccccagg ttaacaaacc tcagttccaa ttcggatgtc    1260
tga                                                                  1263
```

<210> SEQ ID NO 15
<211> LENGTH: 420
<212> TYPE: PRT
<213> ORGANISM: Artificial Sequence
<220> FEATURE:
<223> OTHER INFORMATION: canine 5T4 polypeptide having the amino acid
      sequence

<400> SEQUENCE: 15

```
Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Leu Thr Ser Trp Ala Pro Ser Ala Ala Ser Thr Ser Pro Pro
        35                  40                  45

Ala Ser Ala Ala Ser Ala Pro Pro Leu Pro Gly Gln Cys Pro Gln
    50                  55                  60

Pro Cys Glu Cys Ser Glu Ala Ala Arg Thr Val Lys Cys Val Asn Arg
65                  70                  75                  80

Asn Leu Thr Glu Val Pro Ala Asp Leu Pro Pro Tyr Val Arg Asn Leu
                85                  90                  95

Phe Leu Thr Gly Asn Gln Leu Ala Val Leu Pro Pro Gly Ala Phe Ala
            100                 105                 110

Arg Arg Pro Pro Leu Ala Glu Leu Ala Ala Leu Asn Leu Ser Gly Ser
        115                 120                 125

Ser Leu Arg Glu Val Cys Ala Gly Ala Phe Glu His Leu Pro Ser Leu
    130                 135                 140

Arg Gln Leu Asp Leu Ser His Asn Pro Leu Gly Asn Leu Ser Ala Phe
145                 150                 155                 160

Ala Phe Ala Gly Ser Asp Ala Ser Arg Ser Gly Pro Ser Pro Leu Val
                165                 170                 175

Glu Leu Met Leu Asn His Ile Val Pro Pro Asp Asp Arg Arg Gln Asn
            180                 185                 190

Arg Ser Phe Glu Gly Met Val Ala Ala Leu Arg Ala Gly Arg Ala
        195                 200                 205

Leu Arg Gly Leu Gln Cys Leu Glu Leu Ala Gly Asn Arg Phe Leu Tyr
    210                 215                 220

Leu Pro Arg Asp Val Leu Ala Gln Leu Pro Gly Leu Arg His Leu Asp
225                 230                 235                 240

Leu Arg Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Ala Thr Leu Ala Glu Leu Gln Ser Leu Pro His Val Arg
        275                 280                 285

Val Phe Leu Asp Asn Asn Pro Trp Val Cys Asp Cys His Met Ala Asp
    290                 295                 300

Met Val Ala Trp Leu Lys Glu Thr Glu Val Val Pro Gly Lys Ala Gly
305                 310                 315                 320
```

-continued

Leu Thr Cys Ala Phe Pro Glu Lys Met Arg Asn Arg Ala Leu Leu Glu
             325                 330                 335

Leu Asn Ser Ser His Leu Asp Cys Asp Pro Ile Leu Pro Pro Ser Leu
         340                 345                 350

Gln Thr Ser Tyr Val Phe Leu Gly Ile Val Leu Ala Leu Ile Gly Ala
     355                 360                 365

Ile Phe Leu Leu Val Leu Tyr Leu Asn Arg Lys Gly Ile Lys Lys Trp
 370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
             405                 410                 415

Asn Ser Asp Val
         420

<210> SEQ ID NO 16
<211> LENGTH: 47
<212> TYPE: DNA
<213> ORGANISM: Artificial Sequence
<220> FEATURE:
<223> OTHER INFORMATION: oligonucleotide used to construct flexible
      linker to join the ext racellular domain of B7.1 and ScFv

<400> SEQUENCE: 16
ctagttccgc cgccgccact gccgccacca ccgctcccac cacccccc                    47

<210> SEQ ID NO 17
<211> LENGTH: 38
<212> TYPE: DNA
<213> ORGANISM: Artificial Sequence
<220> FEATURE:
<223> OTHER INFORMATION: Forward primer used in PCR reaction to
      introduce 5' EcoR1 and 3' Sma I sites

<400> SEQUENCE: 17
ctcgaattcc accatggctt gcaattgtca gttgatgc                               38

<210> SEQ ID NO 18
<211> LENGTH: 30
<212> TYPE: DNA
<213> ORGANISM: Artificial Sequence
<220> FEATURE:
<223> OTHER INFORMATION: Reverse primer used in PCR reaction to
      introduce 5' EcoR1 and 3' Sma I sites

<400> SEQUENCE: 18
ctccccgggc ttgctatcag gagggtcttc                                        30

<210> SEQ ID NO 19
<211> LENGTH: 29
<212> TYPE: DNA
<213> ORGANISM: Artificial Sequence
<220> FEATURE:
<223> OTHER INFORMATION: Forward primer used to amplify 5T4 specific
      ScFv

<400> SEQUENCE: 19
ctcactagtg aggtccagct tcagcagtc                                         29

<210> SEQ ID NO 20
<211> LENGTH: 44
<212> TYPE: DNA
<213> ORGANISM: Artificial Sequence

```
<220> FEATURE:
<223> OTHER INFORMATION: Reverse primer used to amplify 5T4 specific
      ScFv

<400> SEQUENCE: 20
ctcgcggccg cttaccgttt gatttccagc ttggtgcctc cacc          44

<210> SEQ ID NO 21
<211> LENGTH: 87
<212> TYPE: DNA
<213> ORGANISM: Artificial sequence
<220> FEATURE:
<223> OTHER INFORMATION: complementary single stranded oligonucleotide
      encoding a translation initiation sequence and the human
      immunoglobin kapp a light chain signal peptide

<400> SEQUENCE: 21
ctagactcga gccaccatgg gatggagctg tatcatcctc ttcttggtag caacagctac    60
aggtgtccac tccgaggtcc agctgca                                       87

<210> SEQ ID NO 22
<211> LENGTH: 79
<212> TYPE: DNA
<213> ORGANISM: Artificial Sequence
<220> FEATURE:
<223> OTHER INFORMATION: complementary single stranded oligonucleotide
      encoding a translation initiation sequence and the human
      immunoglobin kapp a light chain signal peptide

<400> SEQUENCE: 22
gctggacctc ggagtggaca cctgtagctg ttgctaccaa gaagaggatg atacagctcc    60
atcccatggt ggctcgagt                                                79

<210> SEQ ID NO 23
<211> LENGTH: 20
<212> TYPE: DNA
<213> ORGANISM: Artificial Sequence
<220> FEATURE:
<223> OTHER INFORMATION: PCR primer used to amplify 5T4 ScFv

<400> SEQUENCE: 23
gtccagctgc agcagtctgg                                               20

<210> SEQ ID NO 24
<211> LENGTH: 22
<212> TYPE: DNA
<213> ORGANISM: Artificial Sequence
<220> FEATURE:
<223> OTHER INFORMATION: PCR primer used to amplify 5T4 ScFv

<400> SEQUENCE: 24
cgtttgattt caagcttggt gc                                            22

<210> SEQ ID NO 25
<211> LENGTH: 40
<212> TYPE: DNA
<213> ORGANISM: Artificial Sequence
<220> FEATURE:
<223> OTHER INFORMATION: PCR primer used to amplify HIgG1 constant
      region

<400> SEQUENCE: 25
gcgcaagctt gaaatcaaac gggcctccac caagggccca                         40

<210> SEQ ID NO 26
```

```
<211> LENGTH: 30
<212> TYPE: DNA
<213> ORGANISM: Artificial Sequence
<220> FEATURE:
<223> OTHER INFORMATION: PCR primer used to amplify HIgG1 constant
      region

<400> SEQUENCE: 26
gcgcctcgag tcatttaccc ggagacaggg                                    30

<210> SEQ ID NO 27
<211> LENGTH: 40
<212> TYPE: DNA
<213> ORGANISM: Artificial Sequence
<220> FEATURE:
<223> OTHER INFORMATION: PCR primer used to amplify fusion construct

<400> SEQUENCE: 27
gcgcaagctt gaaatcaaac gggcctccac acagagccca                         40

<210> SEQ ID NO 28
<211> LENGTH: 31
<212> TYPE: DNA
<213> ORGANISM: Artificial Sequence
<220> FEATURE:
<223> OTHER INFORMATION: PCR primer used to amplify fusion construct

<400> SEQUENCE: 28
gcgcctcgag tcatttaccg ggatttacag a                                  31

<210> SEQ ID NO 29
<211> LENGTH: 29
<212> TYPE: DNA
<213> ORGANISM: Artificial Sequence
<220> FEATURE:
<223> OTHER INFORMATION: PCR primer used to amplify DNA

<400> SEQUENCE: 29
ggactagtaa tagtgactct gaatgtccc                                     29

<210> SEQ ID NO 30
<211> LENGTH: 34
<212> TYPE: DNA
<213> ORGANISM: Artificial Sequence
<220> FEATURE:
<223> OTHER INFORMATION: PCR primer used to amplify DNA

<400> SEQUENCE: 30
attagcggcc gcttagcgca gttcccacca cttc                               34

<210> SEQ ID NO 31
<211> LENGTH: 35
<212> TYPE: DNA
<213> ORGANISM: Artificial Sequence
<220> FEATURE:
<223> OTHER INFORMATION: B7-Sbf primer for B7-5T4 scFv

<400> SEQUENCE: 31
atcgcctgca ggccaccatg gcttgcaatt gtcag                              35

<210> SEQ ID NO 32
<211> LENGTH: 34
<212> TYPE: DNA
<213> ORGANISM: Artificial Sequence
<220> FEATURE:
<223> OTHER INFORMATION: 5T4sc-RI primer for B7-5T4 scFv
```

-continued

```
<400> SEQUENCE: 32
gcgcgaattc ttaccgtttg atttccagct tggt                                  34

<210> SEQ ID NO 33
<211> LENGTH: 34
<212> TYPE: DNA
<213> ORGANISM: Artificial Sequence
<220> FEATURE:
<223> OTHER INFORMATION: L-Sbf primer for L-5T4scFv

<400> SEQUENCE: 33
atcgcctgca ggccaccatg ggatggagct gtat                                  34

<210> SEQ ID NO 34
<211> LENGTH: 34
<212> TYPE: DNA
<213> ORGANISM: Artificial Sequence
<220> FEATURE:
<223> OTHER INFORMATION: 5T4sc-RI primer for L-5T4scFv

<400> SEQUENCE: 34
gcgcgaattc ttaccgtttg atttccagct tggt                                  34

<210> SEQ ID NO 35
<211> LENGTH: 48
<212> TYPE: DNA
<213> ORGANISM: Artificial Sequence
<220> FEATURE:
<223> OTHER INFORMATION: L-Sbf primer used to prepare L-5T4 scFv

<400> SEQUENCE: 35
ctagtaccgg tggtggtggg agcggtggtg gcggcagtgg cggcggcg                   48

<210> SEQ ID NO 36
<211> LENGTH: 15
<212> TYPE: PRT
<213> ORGANISM: Artificial Sequence
<220> FEATURE:
<223> OTHER INFORMATION: 5T4sc-RI primer used to prepare L-5T4 scFv

<400> SEQUENCE: 36

Gly Gly Gly Gly Ser Gly Gly Gly Gly Ser Gly Gly Gly Gly Ser
1               5                   10                  15

<210> SEQ ID NO 37
<211> LENGTH: 76
<212> TYPE: DNA
<213> ORGANISM: Artificial Sequence
<220> FEATURE:
<223> OTHER INFORMATION: Leader sequence in pBS II

<400> SEQUENCE: 37
ctagacctgc aggccaccat gggatggagc tgtatcatcc tcttcttggt agcaacagct      60
acaggtgtac actccc                                                      76
```